US009370551B2

(12) United States Patent
Cong et al.

(10) Patent No.: US 9,370,551 B2
(45) Date of Patent: Jun. 21, 2016

(54) COMPOSITIONS AND METHODS OF TREATING HEAD AND NECK CANCER

(75) Inventors: Le Cong, Cambridge, MA (US); Ann Marie Egloff, Pittsburgh, PA (US); Levi A. Garraway, Newton, MA (US); Jennifer Rubin Grandis, Pittsburgh, PA (US); Eric S. Lander, Cambridge, MA (US); Nicholas Stransky, Boston, MA (US); Aaron D. Tward, Boston, MA (US); Feng Zhang, Cambridge, MA (US)

(73) Assignees: The Broad Institute, Inc., Cambridge, MA (US); Massachusetts Institute of Technology, Cambridge, MA (US); President and Fellows of Harvard College, Cambridge, MA (US); Massachusetts Eye and Ear Infirmary, Boston, MA (US); Dana-Farber Cancer Institute, Inc., Boston, MA (US); University of Pittsburgh-Of The Commonwealth of Higher Education, Pittsburgh, PA (US); Instituto Carlos Slim de la Salud, A.C., Mexico City (MX)

( * ) Notice: Subject to any disclaimer, the term of this patent is extended or adjusted under 35 U.S.C. 154(b) by 540 days.

(21) Appl. No.: 13/557,988

(22) Filed: Jul. 25, 2012

(65) Prior Publication Data

US 2013/0171124 A1 Jul. 4, 2013

Related U.S. Application Data

(60) Provisional application No. 61/512,279, filed on Jul. 27, 2011.

(51) Int. Cl.

| | |
|---|---|
| ***C12N 15/85*** | (2006.01) |
| ***A61K 38/16*** | (2006.01) |
| ***A61K 38/46*** | (2006.01) |
| ***A61K 45/06*** | (2006.01) |
| ***C07K 14/47*** | (2006.01) |
| ***C12N 9/22*** | (2006.01) |
| ***C12N 15/90*** | (2006.01) |
| *A61K 48/00* | (2006.01) |

(52) U.S. Cl.

CPC ............ *A61K 38/164* (2013.01); *A61K 38/465* (2013.01); *A61K 45/06* (2013.01); *C07K 14/4703* (2013.01); *C07K 14/4705* (2013.01); *C12N 9/22* (2013.01); *C12N 15/907* (2013.01); *A61K 48/005* (2013.01); *C07K 2319/00* (2013.01); *C07K 2319/70* (2013.01); *C07K 2319/71* (2013.01); *C07K 2319/80* (2013.01); *C12N 2710/20011* (2013.01); *C12N 2800/22* (2013.01); *C12N 2999/007* (2013.01)

(58) Field of Classification Search

None

See application file for complete search history.

(56) References Cited

U.S. PATENT DOCUMENTS

| | | | | |
|---|---|---|---|---|
| 2005/0064474 | A1 | 3/2005 | Urnov et al. | |
| 2008/0118469 | A1 | 5/2008 | Zhang et al. | |
| 2011/0145940 | A1 | 6/2011 | Voytas et al. | |
| 2011/0301073 | A1 * | 12/2011 | Gregory et al. | 514/1.1 |
| 2012/0192301 | A1 | 7/2012 | Jaenisch et al. | |
| 2012/0270273 | A1 * | 10/2012 | Zhang et al. | 435/91.52 |

FOREIGN PATENT DOCUMENTS

| | | |
|---|---|---|
| WO | WO 2008/120831 | 10/2008 |
| WO | WO 2009/155659 | 12/2009 |

OTHER PUBLICATIONS

Sanjana, et al., A transcription Activator-Like Effector Toolbox for Genome Engineering (2012) Nature Protocols, vol. 7, No. 1 p. 171-192.

Stransky, N., The Mutation Landscape of Head and Neck Squamous Cell Carcinoma (2011) Science, vol. 333, p. 1157-1160.

Zhang, et al., Efficient Construction of Sequence-Specific TAL Effectors for Modulating Mammalian Transcription (2011) Nature Biotechnology, vol. 29, No. 2, p. 149-154.

Keith L. Matheny, et al., Inhibition of Epidermal Growth Factor Receptor Signaling Decreases p63 Expression in Head and Neck Squamous Carcinoma Cells, The Laryngoscope (2003) vol. 113, p. 936-939.

Weg M. Ongekeo, et al., Gleevec Suppresses p63 Expression in Head and Neck Squamous Cell Carcinoma Despite p63 Activation by DNA-Damaging Agents, The Laryngoscope (2006) vol. 116, p. 1390-1396.

Supplementary EP Search Report for EP 12816869.7 dated Feb. 4, 2015.

Abstract: T. Rampias, H-RAS and PIK3CA Mutations and Response to Cetuximab in Head and Neck Squamous Cell Carcinoma (HNSCC) Journal of Clinical Oncology, ASCO Annual Meeting Abstracts Part 1, May 20, 2011.

(Continued)

*Primary Examiner* — Michele K Joike

(74) *Attorney, Agent, or Firm* — Vedder Price, P.C.; Thomas J. Kowalski; Deborah L. Lu

(57) ABSTRACT

The present invention provides methods related to the treatment of head and neck squamous cell carcinoma (HNSCC) and its associated premalignant lesions. In particular, the invention features methods which may specifically target HNSCC-associated genes and alter gene expression to treat or alleviate a symptom of HNSCC, or its related premalignant lesions. These methods may involve decreasing the function of an HNSCC-associated gene with aberrant gain-of-function; or increasing the function of an HNSCC-associated gene with aberrant loss-of-function.

21 Claims, 37 Drawing Sheets

(56) References Cited

OTHER PUBLICATIONS

James W. Rocco, et al., p63 Mediates Survival in Squamous Cell Carcinoma by Suppression of p73-Dependent Apoptosis, Cancer Cell (2006) vol. 9, No. 1, p. 45-56.

X. Yang, et al., Np63 Versatilely Regulates a Broad NF-B Gene Program and Promotes Squamous Epithelial Proliferation, Migration and Inflammation, Cancer Research (2011) vol. 71, No. 10, p. 3688-3700.

G. A. Jeon, et al., Global Gene Expression Profiles of Human Head and Neck Squamous Carcinoma Cell Lines, International Journal of Cancer, John Wiley & Sons, Inc., US (2004) vol. 112, p. 249-258.

EP Application No. 12816869.7 extended EP Search Report.

* cited by examiner

| SEQ ID NO.s | Monomers (RVD removed) | Frequency |
|---|---|---|
| | LTPDQVVAIASGGKQALETVQRLLPVLCQDHG | 754 |
| | LTPEQVVAIASGGKQALETVQRLLPVLCQAHG | 278 |
| | LTPDQVVAIASGGKQALETVQRLLPVLCQAHG | 254 |
| | LTPAQVVAIASGGKQALETVQRLLPVLCQAHG | 147 |
| | LTPAQVVAIASGGKQALETVQRLLPVLCQDHG | 143 |
| | LTPDQVVAIASGGKQALETVQRLLPVLCEQHG | 107 |
| | LTPDQVVAIANGGKQALETVQRLLPVLCQDHG | 72 |
| | LTLDQVVAIASGGKQALETVQRLLPVLCQDHG | 47 |
| | LTPQQVVAIASGGKQALETVQRLLPVLCQAHG | 47 |
| | LTPDQVVAIANGGKQALETVQRLLPVLCQAHG | 40 |
| | LTPNQVVAIASGGKQALETVQRLLPVLCQDHG | 35 |
| | LTLDQVVAIASGGKQALETVQRLLPVLCQAHG | 27 |
| | LTPAQVVAIANGGKQALETVQRLLPVLCQDHG | 20 |
| | LTPEQVVAIASGGKQALETVQALLPVLCQAHG | 19 |
| | LTLDQVVAIASGSKQALETVQRLLPVLCQDHG | 19 |
| | LTQDQVVAIASGGKQALETVQRLLPVLCQDHG | 18 |
| | LSPDQVVAIASGGKQALETVQRLLPVLCQDHG | 13 |
| | LTPDQVVAIANGGKQALETLQRLLPVLCQDHG | 13 |
| | LTPDQVVAIASGGKQALETLQRLLPVLCQDHG | 11 |
| | LTPDQVVAIASGGKQALETVQRLLPVLRQAHG | 11 |
| | LTPDQVVAIASGGNQALETVQRLLPVLCQAHG | 11 |
| | LTPDQVVAIASGGKQALATVQRLLPVLCQAHG | 10 |
| | LTPAQVVAIANGGKQALETVQRLLPVLCQAHG | 9 |
| | LTLAQVVAIASGGKQALETVQRLLPVLCQAHG | 9 |
| | LTPEQVVAIACGGKQALETVQRLLPVLCQAHG | 9 |
| | LTPAQVVAIASGGKQALETVQQLLPVLCEQHG | 9 |
| | LTPQQVVAIASGGRPALETVQRLLPVLCQAHG | 9 |
| | LTPDQVVAIASGSKQALETVQRLLPVLCQDHG | 8 |
| | LTPNQVVAIASGGKQALETVQRLLPVLCQAHG | 8 |
| | LTPDQVVAIASGGKQALGTVQRLLPVLCQDHG | 8 |
| | LTLAQVVAIASGGKQALETVQRLLPVLCQDHG | 8 |
| | LTPAQAVAIASGGKQALETVQRLLPVLCQDHG | 7 |
| | LTPAQVVAIASGGNQALETVQRLLPVLCQDHG | 7 |
| | LTPDQVVAIASGGKQALETLQRLLPVLCQAHG | 7 |
| | LTPDQVVAIANGGKQALETLQRLLPVLCQAHG | 7 |
| | LTPDQVVTIASGGKQALETVQRLLPVLCQDHG | 7 |
| | LTPAQVVAIANGGKQALETVRRLLPVLCQDHG | 7 |
| | LTPDQVVAIASGGNQALETVQRLLPVLCQDHG | 6 |
| | LTPDQVVAIASGGKQALETVQRLLPVLCQTHG | 6 |
| | LPPDQVVAIASGGKQALETVQRLLPVLCQDHG | 6 |

FIG. 15B

| SEQ ID NO.s | Monomers (RVD removed) | Frequency |
|---|---|---|
| | LTSDQVVAIASGGKQALETVQRLLPVLCQDHG | 6 |
| | LTPAQVVAIASGGKQALETVQRLLPVLCEQHG | 6 |
| | LIPAQVVAIASGGKQALETVQRLLPVLCQDHG | 5 |
| | LTPAQVVAIASGGKQALETMQRLLPVLCQAHG | 5 |
| | LTRDQVVAIASGGKQALETVQRLLPVLCQDHG | 5 |
| | LTPDQVVATASGGKQALETVQRLLPVLCQDHG | 5 |
| | LIPDQVVAIANGGKQALETVQRLLPVLCQAHG | 5 |
| | LTPDQVVAIASGGKQALETVQRLLPVLCQNHG | 5 |
| | LTLDQVVAIASGGKKALETVQRLLPVLCQDHG | 4 |
| | LTPDQLVAIANGGKQALETVQRLLPVLCQDHG | 4 |
| | LTPDQVVAIASGGKQALETVQRLLPVLCQGHG | 4 |
| | LTPDQVVAIASGGKQALETVQRLLPVLCQEHG | 4 |
| | LTLDKVVAIASGGKQALETVQRLLPVLCQDHG | 4 |
| | LTPAQVVAIASGSKQALETVQRLLPVLCQAHG | 4 |
| | LTPDKVVAIASGGKQALETVQRLLPVLCQAHG | 4 |
| | LTQDQVVAIASGGKQALETVQRLLPVLYQDHG | 4 |
| | LTPAQVVAIVSGGKQALETVQRLLPVLCQAHG | 4 |
| | LTPDKVVAIANGGKQALETVQRLLPVLCQDHG | 4 |
| | LTQDQVVAIASGGKQALETVQRLLPVLCQAHG | 4 |
| | LTPDQVMAIANGGKQALETVQRLLPVLCQDHG | 4 |
| | LTTDQVVAIASGGKQALETVQRLLPVLCQAHG | 4 |
| | LTPDQVVAIASGSKQALETVQRLLPVLCQAHG | 3 |
| | LTPDQVVAIANGGKQALETVQRLLLVLCQAHG | 3 |
| | LTQEQVVAIASGGKQALETVQRLLPVLCQAHG | 3 |
| | LTPDQVVTIANGGKQALETVQRLLPVLCQAHG | 3 |
| | LSPAQVVAIASGGKQALETVQRLLPVLCHDHG | 3 |
| | LTPDQVVAIASGGKQALEMVQRLLPVLCQAHG | 3 |
| | LIPDQVVAIASGGKQALETVQRLLPVLCQDHG | 3 |
| | LTPVQVVAIASGGKQALETVQRLLPVLCQDHG | 3 |
| | LTPDQVVAIASGGKQALKTVQRLLPVLCQDHG | 3 |
| | LTPDQVVAIASGGKQALETMQRLLPVLCQAHG | 3 |
| | LTPAQVVAIASGGKQALETVQRLFPVLCQDHG | 3 |
| | LTPAQVVAIASGGKQALETVQQLLPVLCQAHG | 3 |
| | LTPAQVVALASGGKQALETVQRLLPVLCQDHG | 3 |
| | LTPDQVVAIASGGRPALETVQRLLPVLCEQHG | 3 |
| | LTPDQVVAIASGGKQALATVQRLLPVLCQDHG | 3 |
| | LTQVQVVAIASGGKQALETVQRLLPVLCQAHG | 3 |
| | LTPDQVVAIARGGKQALETVQRLLPVLCQAHG | 3 |
| | LPPDQVVAIASGGKQALETVQRLLPVLCQAHG | 3 |
| | LTLDQVVAIASGSKQALETVQRLLPVLCQAHG | 3 |

FIG. 15C

| SEQ ID NO.s | Monomers (RVD removed) | Frequency |
|---|---|---|
| | LSPDQVVAIANGGKQALETLQRLLPVLCQTHA | 3 |
| | LNPDQVVAIASGGKQALETVQRLLPVLCQDHG | 3 |
| | LTPDQVMAIASGGKQALETVQRLLPVLCQDHG | 3 |
| | LTPAQVVAIASGGKQALETVRRLLPVLCQAHG | 3 |
| | LTPDQVVAIASGGKQTLETVQRLLPVLCQDHG | 3 |
| | LTPDQVMTIASGGKQALETVQRLLPVLCQDHG | 3 |
| | LTPAQVVTIASGGKQALETVQRLLPVLCQDHG | 3 |
| | LTPAQVVAIASGGKQALETVQRLLPVLCRAHG | 3 |
| | LSPDQVVAIASGGKQALETVQRLLPVLCQAHG | 3 |
| | LTPDQVVGIASGGKQALETVQRLLPVLCQDHG | 2 |
| | LTPDQVVAIASGGKQALETVQRLLPVLCQANG | 2 |
| | LTPAQVVAIASGGKQALETVQRLLPVLCQTHG | 2 |
| | LTPDQVVAIASGGKQALEMVQRLLPVLCQDHG | 2 |
| | LTPDQVVAIASGGKQALETMQRLLPVLCQDHG | 2 |
| | LTPDQVVAIANGGKQALATVQRLLPVLCQDHG | 2 |
| | LTPDQVVTIASGGKQALETVQRLLPVLCQAHG | 2 |
| | LTPDQVVAIASGGKQALETVQRLLTVLCQDHG | 2 |
| | MTPDQVVAIASGGKQALETVQRLLPVLCQDHG | 2 |
| | LAPDQVVAVASGGKQALETVQRLLPVLCQDHG | 2 |
| | LTPAQVVAIASGGKQALKTVQQLLPVLCEQHG | 2 |
| | LTPDQVVAIARGGKQALETVQRLLPVLCQDHG | 2 |
| | LTPDQVVAIASGGKQALETVQQLLPVLCQAHG | 2 |
| | LTPDQVLAIASGGKQALETLQRLLPVLCQDHG | 2 |
| | LTPEQVVAIARGGKQALETVQRLLPVLCQAHG | 2 |
| | LTPAQVVAIASGGKQALETMQRLLPVLCRAHG | 2 |
| | LTPDQVVAIANGGKQALEMVQRLLPVLCQDHG | 2 |
| | LTTDQVVTIASGGKQALETVQRLLPVLCQDHG | 2 |
| | LTPTQVMAIANGGKQALETVQRLLPVLCQDHG | 2 |
| | LTPQQVVAIASGGKQALETVQALLPVLCQAHG | 2 |
| | LTPDQVVAIASGGKQALETVQRLLPMLCQDHG | 2 |
| | LTSAQVVAIANGGKQALETVQRLLPVLCQDHG | 2 |
| | LTPDQVVAIASGGKQALETVQQLLPVLCQDHG | 2 |
| | LTPDQVVAIANGGKQALATVQRLLPVLCQAHG | 2 |
| | LTPAQVVAIASGGKQALETVQRLLPMLCQAHG | 2 |
| | LTLDQVVAIASGGKQALETVQRLLPVLCQARG | 2 |
| | LTPAQVVAIASGGKQALETLQRLLPVLCQDHG | 2 |
| | LTPDQVVAIANGGKQALETVQRLLPVLCQNHG | 2 |
| | LTPDQVVTIASGGKQALEMVQRLLPVLCQDHG | 2 |
| | LTPDQVVAIASGGKQALERVQRLLPVLCEQHG | 1 |
| | LTPEQVVAIACGGKQALETVQALLPVLRQAHG | 1 |

FIG. 15 D

| SEQ ID NO.s | Monomers (RVD removed) | Frequency |
|---|---|---|
| | LTPDQVVAIASGGKQALETVQRLLPVLCRDHG | 1 |
| | LTPEQVVAIASGGKQALETVQRLLPMLCQAHG | 1 |
| | LTPEQVVAIACGGKQALETVQRLLPVLRHAHG | 1 |
| | LTPDQVVAIASGGKQALETVQRLLPVLCQHHG | 1 |
| | LIPDQVVAIASGGKQALETVQRLLPVLCQHHG | 1 |
| | LTRAQVVAIASGGKQALETVQRLLPVLCEQHG | 1 |
| | LTPDQVVAIANGGKQAVGTVQRLLPVLCQAHG | 1 |
| | LTLDQVVAIASGGKQALETVQRLLPVLCEQHG | 1 |
| | LTPAQVVAIASGGKQALETVQRLLPMLCQDHG | 1 |
| | LTPDQVVAIASGSKQALETMQRLLPVLCQDHG | 1 |
| | LTPDQVVAIASGGKQALETVQRLLPVLCKQHG | 1 |
| | LTLDQVVAIASGGKQALETVQRLLPVLCQTHG | 1 |
| | LTPDQVVAIASGGKQALEAVQRLLPVLCQDHG | 1 |
| | LTPAQVVTIASGGKQALETVQRLLPVLCEQHG | 1 |
| | LTPAQVMAIASGGKQALETVQRLLPVLCQDHG | 1 |
| | LTREQVVAIASGGKQALETVQRLLPVLRQAHG | 1 |
| | LTLAQVVAIANGGKQALETVQRLLPVLCQAHG | 1 |
| | LTLEQVVAIASGGKQALETVQRLLPVLCQAHG | 1 |
| | LTPQQVVAIASGGKQALETVQRLLPVLCEQHG | 1 |
| | LSPDQVVAIANGGKQALETVQRLLPVLCQDHG | 1 |
| | LTPDQVVAIANGGKQALETVQRLLPVLCQHHG | 1 |
| | LTPEQVVAIASGGKQALETVQALLPVLRQAHG | 1 |
| | LSQDQVVAIASGGKQALETVQRLLPVLCQDHG | 1 |
| | LPPEQVVAIASGGKQALETVQRLLPVLCQAHG | 1 |
| | LTPDQVVAIASGGKQALEAVQRLLPVLCQAHG | 1 |
| | LTPDQVVAIANGGKQALETVQRLLPVLCQEHG | 1 |
| | LTLDQVAAIASGGKQALETVQRLLPVLCQAHG | 1 |
| | LTPDQVVAIASGGKQALETVQRVLPVLCQDHG | 1 |
| | LIPAQVVAIASGGKQALETVQRLLPVLCQAHG | 1 |
| | LTPAQVVAIASGGKQALETVQRLLPVLRQAHG | 1 |
| | LTPAQVVAIASGSKQALETVQRLLPVLCQTHG | 1 |
| | LTPQQVVAIASGGKQALETVQRLLPVLCQDHG | 1 |
| | LTPDQVVAIANGGKQAVETVQRLLPVLCQAHG | 1 |
| | LSPDQVVTIASGGKQALETLQRLLPVLCQDHG | 1 |
| | LTPVQVVAIASGGKQALETVQRLLPVLCQAHG | 1 |
| | LTLDQVVAIASGSKQALETVQRLLPVLCQTHG | 1 |
| | LTPAQVVAIACGGKQALETVRRLLPVLCQAHG | 1 |
| | LTPAQVVAIASGSKQALETVQRLFPVLCQAHG | 1 |
| | LPPAQVVAIASGGKQALETVQRLLPVLCQAHG | 1 |
| | LTPDQVVAIASGGKQALETVQRLLPVLFQEHG | 1 |

FIG. 15E

| SEQ ID NO.s | Monomers (RVD removed) | Frequency |
| --- | --- | --- |
| | LTPAKVVAIASGGKQALETVQRLLPVLCQDHG | 1 |
| | LTPVQVVAIASGGKQALATVQRLLPVLCQDHG | 1 |
| | LTPDQVVAIASGGKQALETVQRLLPGLCQDHG | 1 |
| | LTLAQVVAIANGGKQALETVQRLLPVLCQDHG | 1 |
| | LTPAQVVAIASGGKQALETVQRLLTVLCQDHG | 1 |
| | LPPAQVVAIASGGKQALETVQRLLPVLCQDHG | 1 |
| | LTPAQAVAIASGGKQALETVQRLLPVLCQAHG | 1 |
| | LTPAQVVAIVSGGKQALETVQRLLPVLCQTHG | 1 |
| | LTPDQVVAVAGGGKQALETVQRLLPVLCQDHG | 1 |
| | LTPDQVVAIASGGKQALGTVQRLLPVLCQAHG | 1 |
| | LPPAQVVAIASGGKQALETVQRLLPVLCEAHG | 1 |
| | LTTDQVVAIASGGKQALETVQRLLPVLCQDHG | 1 |
| | LTPDQVVAIANGGKQALETVQRLVPVLCQDHG | 1 |
| | LTPDQVVAIASGGKQALETVQRLLPVLCQTHA | 1 |
| | LTLAQVVAIASGGKQALETVQRLLPVLCQTHG | 1 |
| | LTPNQLVAIANGGKQALETVQRLLPVLCQDHG | 1 |
| | LSPAQVVAIASGSKQALETVQRLLPVLCQDHG | 1 |
| | LTPDQVVAIASGGKQALETVQRVLPVLCQAHG | 1 |
| | LTPDQVMAIANGGKQALETVQRLLPVLCQAHG | 1 |
| | LTPEQVVAIASGGRQALETVQRLLPVLCQAHG | 1 |
| | LTPAQVVAIASGGKQALETVQWLLPVLCQAHG | 1 |
| | LTPDKVVAIASGGKQALETVQRLLPVLCQDHG | 1 |
| | LTPAQVMAIANGGKQALETVQRLLPVLCQDHG | 1 |
| | LTQDQVVAIASGGKQALETVQRLLPVLCQANG | 1 |
| | LTPAQVVAIASGGKPALETVQRLLPVLCEQHG | 1 |
| | LTPDQVVAIASSGKQALETMQRLLPVLCQDHG | 1 |
| | LTPDQVVAIASGSKQALETVQRLLPVLRQDHG | 1 |
| | LTPYQVVAIASGSKQALETVQRLLPVLCQDHG | 1 |
| | LTPYQVVAIASGGKQALETVQRLLPVLCQAHG | 1 |
| | LTLDQVVAIASGGKQALETVQRLLPVLCQEHG | 1 |
| | LTLEQVVAIASGGKQALETVQRLLLVLCQAHG | 1 |
| | LTPDQVVAIASGGKQALETVRRLLQVLCQDHG | 1 |
| | LTPDQVVAIASGGKQALETVQRLLPVLRQDHG | 1 |
| | LTPDQVVSIANGGKQALETVQRLLPVLCQAHG | 1 |
| | LTPDQVVAIANGGKQALETVQRLLPVLCQTHG | 1 |
| | LTPDQVVAIASGGKQALETVKRLLPVLCQAHG | 1 |
| | LTTDQVVAIANGGKQALETVQRLLPVLCQDHG | 1 |
| | LIPQQVVAIASGGKQALETVQRLLPVLCQDHG | 1 |
| | LTLTQVVAIASGGKQALETVQRLLPVLCQAHG | 1 |
| | LTPTQVVAIASGGKQALETVQRLLPVLCQDHG | 1 |

FIG. 15F

| SEQ ID NO.s | Monomers (RVD removed) | Frequency |
|---|---|---|
| | LTPTQVMAIANGGKQALETVQRLLPVLCQAHG | 1 |
| | LTPDQVVAVASGGKQALETVQRLLPVLCQAHG | 1 |
| | LTPAQVVAIASGSKQALETVQRLLPVLCQDHG | 1 |
| | LTPGQVVAIASGGKRALETVQRLLPVLCQDHG | 1 |
| | LTPDQVVVIASGGKQALETVQRLLPVLCQAHG | 1 |
| | LPPDQVVAIASGSKQALETVQRLLPVLCQDHG | 1 |
| | LTPDQVVTIANGSKQALETVQRLLPVLCQAHG | 1 |
| | LTPAQVVAIASGGKQALETVQRLLQVLCQDHG | 1 |
| | LTPDHVVAIASGGKQALETVQRLLPVLCQDHG | 1 |
| | LTPDQVVAIASGGKQALETVQRLLQVLCQDHG | 1 |
| | LTPDQVVAIASGGRQALETVQRLLPVLCEQHG | 1 |
| | LHPGQVVAIASGGKQALETVQRLLPVLCQAHG | 1 |
| | LTLDQVVSIASGGKQALETVQRLLPVLCQDHG | 1 |
| | LTPDQVVAIASGGKQALETVQRLLPALCQDHG | 1 |
| | LTPDQVVAIASGGKPALETVQRLLPVLCEQHG | 1 |
| | LTPAQVVAIASGGKQALKTVQRLLPVLCQAHG | 1 |
| | LTPDQVVAIASGGKRALETVQRLLPVLCQAHG | 1 |
| | LNPDQVVAIASGGKQALETVQRLLPVLCQAHG | 1 |
| | LTPDQVVAIASGGKQALETVKRLLPVLCQDHG | 1 |
| | LTLDQVVAIANGGKQALETVQRLLPVLCQAHG | 1 |
| | LTPAQVVAIASGGKQALETVQRLLPVLCRDHG | 1 |
| | LTPAQVLAIASGGKQALETVQRLLTVLCQDHG | 1 |
| | LTPAQVVAIASGGKQALETMQRLLPVLCQDHG | 1 |
| | LTPDQVVAIASGGKQALETVQRLLPGLCQAHG | 1 |
| | LTREQVVAIASGGKQALETVQALLPVLRQAHG | 1 |
| | LTPAQVVAIASGGKQALETVQRLLPVLCQVHG | 1 |
| | LTPNQVVAIASGGKQALETVQRLLLVLCQDHG | 1 |
| | LTPDQVMAIASGGKQALETVQRLLPVLCQAHG | 1 |
| | LTREQVVAIASGGKQALETVQRLLPVLCQDHG | |
| | LSTAQVVAIASGGKQALEGIGEQLLKLRTAPYG | |
| | LSTAQVVAVASGGKPALEAVRAQLLALRAAPYG | |

FIG. 21

| Characteristic | Whole Exome Sequenced Tumors (n=92) | | Tumors in Final Analysis (n=74) | | P (Final Analysis Included vs. Excluded) |
|---|---|---|---|---|---|
| Age, years | | | | | |
| Median (range) | 59 (33 - 80) | | 58 (33 - 77) | | 0.137‡ |
| Sex, N (%) | | | | | |
| Men | 69 | 75.0% | 55 | 74.3% | 0.513§ |
| Women | 23 | 25.0% | 19 | 25.7% | |
| Cigarette Smoker, N % | | | | | |
| Never | 15 | 16.3% | 13 | 17.6% | 0.415§ |
| Former | 24 | 26.1% | 17 | 23.0% | |
| Active | 53 | 57.6% | 44 | 59.5% | |
| Tobacco* and Alcohol Use, N % | | | | | |
| Never Tobacco, Never Drinker | 5 | 5.4% | 5 | 6.8% | 0.902§ |
| Never Tobacco, Ever Drinker | 5 | 5.4% | 4 | 5.4% | |
| Ever Tobacco, Never Drinker | 13 | 14.1% | 10 | 13.5% | |
| Ever Tobacco, Ever Drinker | 68 | 73.9% | 54 | 73.0% | |
| Ever Tobacco, Unknown Drinker | 1 | 1.1% | 1 | 1.4% | |
| Tumor Type, N % | | | | | |
| Primary | 85 | 92.4% | 70 | 94.6% | 0.133§ |
| Recurrent | 7 | 7.6% | 4 | 5.4% | |
| Prior RT or CRT†, N % | | | | | |
| No | 83 | 90.2% | 68 | 91.9% | 0.371§ |
| Yes | 9 | 9.8% | 6 | 8.1% | |
| Clinical Disease Stage, N % | | | | | |
| I-II | 7 | 7.6% | 6 | 8.1% | 0.339§ |
| III | 17 | 18.5% | 13 | 17.6% | |
| IV | 61 | 66.3% | 51 | 68.9% | |
| Recurrent | 7 | 7.6% | 4 | 5.4% | |
| Tumor Grade, N % | | | | | |
| Well Differentiated | 2 | 2.2% | 2 | 2.7% | 0.777§ |
| Moderately Differentiated | 62 | 67.4% | 48 | 64.9% | |
| Poorly Differentiated | 27 | 29.3% | 23 | 31.1% | |
| Unknown | 1 | 1.1% | 1 | 1.4% | |
| Cancer Site, N % | | | | | |
| Oral cavity | 51 | 55.4% | 38 | 51.4% | 0.055§ |
| Oropharynx | 15 | 16.3% | 11 | 14.9% | |
| Hypopharynx | 9 | 9.8% | 8 | 10.8% | |
| Sinonasal | 2 | 2.2% | 2 | 2.7% | |
| Larynx | 15 | 16.3% | 15 | 20.3% | |
| Tumor HPV Status¶ | | | | | |
| Positive | 13 | 14.1% | 11 | 14.9% | 1.0§ |
| Negative | 79 | 85.9% | 63 | 85.1% | |
| HPV-Positive Cancer Site¶, N % | (n=13) | | (n=11) | | |
| Oral cavity | 2 | 15.4% | 2 | 18.2% | 1.0§ |
| Oropharynx | 8 | 61.5% | 7 | 63.6% | |
| Hypopharynx | 2 | 15.4% | 1 | 9.1% | |
| Sinonasal | 1 | 7.7% | 1 | 9.1% | |
| Larynx | 0 | 0.0% | 0 | 0.0% | |
| HPV-Negative Cancer Site¶, N % | (n=79) | | (n=63) | | |
| Oral cavity | 49 | 62.0% | 36 | 57.1% | 0.030§ |
| Oropharynx | 7 | 8.9% | 4 | 6.3% | |
| Hypopharynx | 7 | 8.9% | 7 | 11.1% | |
| Sinonasal | 1 | 1.3% | 1 | 1.6% | |
| Larynx | 15 | 19.0% | 15 | 23.8% | |

*Tobacco defined as cigarette, cigar, pipe, or chewing tobacco use

† Within 10 years prior to analyzed tumor event

‡Rank sum test

§Fisher's exact test

¶HPV tumor status defined by HPV-16 PCR or HPV ISH if insufficient DNA for PCR analysis

FIG. 22A

| rank | gene | description | N | n | npat | nsite | nsil | *CpG->T | Tp*Cp (A/C/T) ->(T/G) | *CpG-> (G/A) | (A/G/T) p*G->T | (A/C/G) p*Cp(A/C/T) ->(T/G) | A->mut | indel+null | p | q |
|---|---|---|---|---|---|---|---|---|---|---|---|---|---|---|---|---|
| 1 | TP53 | tumor protein p53 | 90636 | 49 | 46 | 44 | 1 | 6 | 2 | 2 | 2 | 8 | 6 | 23 | <1.00e-11 | <9.43e-08 |
| 2 | CDKN2A | cyclin-dependent kinase inhibitor 2A (melanoma, p16, inhibits CDK4) | 52520 | 9 | 9 | 9 | 0 | 0 | 0 | 1 | 1 | 2 | 0 | 5 | <1.00e-11 | <9.43e-08 |
| 3 | PRDM9 | PR domain containing 9 | 200800 | 9 | 9 | 9 | 2 | 1 | 0 | 0 | 3 | 1 | 3 | 1 | 1.50E-08 | 0.000094 |
| 4 | CASP8 | caspase 8, apoptosis-related cysteine peptidase | 129651 | 6 | 6 | 5 | 0 | 0 | 0 | 0 | 0 | 0 | 1 | 5 | 8.01E-08 | 0.00038 |
| 5 | FAT1 | | 1019417 | 11 | 9 | 11 | 0 | 2 | 0 | 0 | 0 | 0 | 0 | 9 | 1.53E-07 | 0.00058 |
| 6 | CSMD3 | CUB and Sushi multiple domains 3 | 844688 | 13 | 12 | 13 | 5 | 2 | 2 | 1 | 4 | 3 | 0 | 1 | 2.78E-07 | 0.00088 |
| 7 | COL22A1 | collagen, type XXII, alpha 1 | 336851 | 10 | 9 | 10 | 3 | 0 | 2 | 1 | 3 | 2 | 0 | 2 | 3.40E-07 | 0.00092 |
| 8 | NOTCH1 | Notch homolog 1, translocation-associated (Drosophila) | 399201 | 10 | 10 | 10 | 1 | 3 | 0 | 0 | 0 | 2 | 0 | 5 | 4.32E-07 | 0.001 |
| 9 | PTEN | phosphatase and tensin homolog (mutated in multiple advanced cancers 1) | 85211 | 5 | 5 | 5 | 0 | 1 | 0 | 0 | 1 | 1 | 0 | 2 | 1.03E-06 | 0.0022 |
| 10 | SYNE1 | spectrin repeat containing, nuclear envelope 1 | 1988656 | 23 | 15 | 23 | 3 | 2 | 5 | 1 | 4 | 1 | 6 | 4 | 3.02E-06 | 0.0054 |
| 11 | HRAS | v-Ha-ras Harvey rat sarcoma viral oncogene homolog | 45365 | 4 | 4 | 3 | 0 | 0 | 0 | 0 | 2 | 2 | 0 | 0 | 3.21E-06 | 0.0054 |
| 12 | RIMS2 | regulating synaptic membrane exocytosis 2 | 317199 | 9 | 8 | 9 | 1 | 2 | 2 | 0 | 2 | 1 | 2 | 0 | 3.41E-06 | 0.0054 |
| 13 | USH2A | Usher syndrome 2A (autosomal recessive, mild) | 1172874 | 15 | 11 | 15 | 2 | 0 | 3 | 1 | 1 | 4 | 5 | 1 | 7.60E-06 | 0.011 |
| 14 | C19orf26 | chromosome 19 open reading frame 26 | 59860 | 4 | 2 | 4 | 0 | 0 | 3 | 0 | 0 | 1 | 0 | 0 | 0.000016 | 0.022 |
| 15 | MAGEC1 | melanoma antigen family C, 1 | 253360 | 6 | 4 | 6 | 1 | 0 | 0 | 1 | 1 | 2 | 1 | 1 | 0.000021 | 0.026 |
| 16 | CLSTN2 | calsyntenin 2 | 204299 | 6 | 6 | 6 | 2 | 1 | 0 | 1 | 0 | 1 | 2 | 1 | 0.000031 | 0.037 |
| 17 | KCTD8 | potassium channel tetramerisation domain containing 8 | 76929 | 4 | 4 | 4 | 0 | 0 | 1 | 2 | 1 | 0 | 0 | 0 | 0.000037 | 0.042 |
| 18 | THSD7A | thrombospondin, type I, domain containing 7A | 360780 | 7 | 7 | 7 | 4 | 2 | 0 | 1 | 1 | 2 | 0 | 1 | 0.000042 | 0.044 |
| 19 | PIK3CA | phosphoinositide-3-kinase, catalytic, alpha polypeptide | 242191 | 6 | 6 | 5 | 0 | 0 | 2 | 1 | 0 | 0 | 3 | 0 | 0.000045 | 0.045 |
| 20 | OR4C15 | olfactory receptor, family 4, subfamily C, member 15 | 82293 | 4 | 4 | 4 | 1 | 1 | 1 | 0 | 1 | 0 | 1 | 0 | 0.000052 | 0.049 |
| 21 | ALLC | allantoicase | 85678 | 4 | 3 | 4 | 0 | 0 | 0 | 1 | 1 | 0 | 1 | 1 | 0.000057 | 0.051 |
| 22 | PRB4 | proline-rich protein BstNI subfamily 4 | 55944 | 3 | 3 | 3 | 0 | 0 | 0 | 1 | 1 | 0 | 0 | 1 | 0.000061 | 0.051 |
| 23 | CDH10 | cadherin 10, type 2 (T2-cadherin) | 177817 | 5 | 5 | 5 | 3 | 1 | 0 | 0 | 3 | 0 | 1 | 0 | 0.000062 | 0.051 |
| 24 | GRM8 | glutamate receptor, metabotropic 8 | 205394 | 5 | 5 | 5 | 1 | 1 | 0 | 1 | 2 | 0 | 0 | 1 | 0.000087 | 0.065 |
| 25 | NETO2 | neuropilin (NRP) and tolloid (TLL)-like 2 | 116624 | 4 | 4 | 4 | 0 | 1 | 0 | 0 | 0 | 2 | 0 | 1 | 0.000087 | 0.065 |
| 26 | VN1R4 | vomeronasal 1 receptor 4 | 66125 | 3 | 3 | 3 | 0 | 0 | 0 | 1 | 0 | 0 | 2 | 0 | 0.0001 | 0.072 |
| 27 | OR5L2 | olfactory receptor, family 5, subfamily L, member 2 | 69526 | 3 | 2 | 3 | 0 | 0 | 0 | 1 | 0 | 1 | 0 | 1 | 0.0001 | 0.073 |
| 28 | PPP1R9A | protein phosphatase 1, regulatory (inhibitor) subunit 9A | 295497 | 6 | 6 | 6 | 2 | 0 | 2 | 1 | 1 | 0 | 0 | 2 | 0.00011 | 0.073 |
| 29 | MAFA | v-maf musculoaponeurotic fibrosarcoma oncogene homolog A (avian) | 17034 | 2 | 2 | 1 | 0 | 0 | 0 | 0 | 0 | 0 | 0 | 2 | 0.00013 | 0.082 |
| 30 | LRFN5 | leucine rich repeat and fibronectin type III domain containing 5 | 160748 | 5 | 5 | 5 | 4 | 0 | 1 | 0 | 2 | 0 | 2 | 0 | 0.00013 | 0.082 |
| 31 | MED1 | mediator complex subunit 1 | 355333 | 7 | 4 | 7 | 0 | 0 | 4 | 0 | 2 | 1 | 0 | 0 | 0.00013 | 0.082 |
| 32 | ADCY8 | adenylate cyclase 8 (brain) | 260795 | 6 | 6 | 6 | 0 | 2 | 0 | 1 | 1 | 1 | 0 | 1 | 0.00015 | 0.087 |
| 33 | ZFHX4 | zinc finger homeobox 4 | 726687 | 10 | 9 | 10 | 3 | 0 | 3 | 0 | 1 | 1 | 5 | 0 | 0.00016 | 0.089 |
| 34 | MLL2 | myeloid/lymphoid or mixed-lineage leukemia 2 | 1016105 | 9 | 8 | 9 | 0 | 2 | 0 | 0 | 1 | 0 | 0 | 6 | 0.00016 | 0.089 |
| 35 | SI | sucrase-isomaltase (alpha-glucosidase) | 410994 | 7 | 6 | 7 | 4 | 1 | 1 | 0 | 3 | 0 | 2 | 0 | 0.00016 | 0.089 |
| 36 | ZNF804B | zinc finger protein 804B | 300421 | 6 | 6 | 5 | 2 | 0 | 2 | 0 | 2 | 0 | 0 | 2 | 0.00017 | 0.09 |
| 37 | LILRB1 | leukocyte immunoglobulin-like receptor, subfamily B (with TM and ITIM domains), member 1 | 141971 | 5 | 5 | 5 | 0 | 1 | 1 | 0 | 1 | 0 | 2 | 0 | 0.00018 | 0.09 |

FIG. 22B

| rank | gene | description | N | n | npat | nsite | nsil | *CpG->T | Tp*Cp (A/C/T) ->(T/G) | *CpG-> (G/A) | (A/G/T) p*G->T | (A/C/G) p*Cp(A/C/T) ->(T/G) | A->mut | indel+null | p | q |
|---|---|---|---|---|---|---|---|---|---|---|---|---|---|---|---|---|
| 38 | PKHD1L1 | polycystic kidney and hepatic disease 1 (autosomal recessive)-like 1 | 884500 | 11 | 6 | 11 | 2 | 0 | 1 | 0 | 2 | 1 | 5 | 2 | 0.00019 | 0.096 |
| 39 | CNTNAP2 | contactin associated protein-like 2 | 292333 | 6 | 6 | 6 | 0 | 1 | 0 | 0 | 3 | 1 | 1 | 0 | 0.00021 | 0.1 |
| 40 | SLITRK3 | SLIT and NTRK-like family, member 3 | 217238 | 5 | 5 | 5 | 1 | 2 | 0 | 0 | 0 | 1 | 1 | 1 | 0.00022 | 0.11 |
| 41 | C7orf23 | chromosome 7 open reading frame 23 | 27487 | 2 | 2 | 2 | 0 | 0 | 0 | 1 | 0 | 0 | 0 | 1 | 0.00023 | 0.11 |
| 42 | NUDT14 | nudix (nucleoside diphosphate linked moiety X)-type motif 14 | 38278 | 3 | 3 | 3 | 0 | 1 | 1 | 1 | 0 | 0 | 0 | 0 | 0.00023 | 0.11 |
| 43 | WIPF2 | WAS/WASL interacting protein family, member 2 | 99093 | 4 | 2 | 4 | 0 | 0 | 3 | 0 | 1 | 0 | 0 | 0 | 0.00025 | 0.11 |
| 44 | RUFY1 | RUN and FYVE domain containing 1 | 136877 | 4 | 4 | 4 | 0 | 1 | 0 | 1 | 0 | 1 | 1 | 0 | 0.00025 | 0.11 |
| 45 | TP63 | tumor protein p63 | 167168 | 5 | 5 | 5 | 0 | 2 | 1 | 0 | 0 | 1 | 0 | 1 | 0.00031 | 0.13 |
| 46 | MAGEC2 | melanoma antigen family C, 2 | 83183 | 3 | 3 | 3 | 0 | 0 | 0 | 1 | 0 | 0 | 1 | 1 | 0.00034 | 0.14 |
| 47 | NSD1 | nuclear receptor binding SET domain protein 1 | 598944 | 7 | 7 | 7 | 0 | 1 | 0 | 0 | 1 | 1 | 0 | 4 | 0.00035 | 0.14 |
| 48 | NUDT11 | nudix (nucleoside diphosphate linked moiety X)-type motif 11 | 28229 | 2 | 2 | 1 | 0 | 0 | 0 | 0 | 0 | 0 | 0 | 2 | 0.00035 | 0.14 |
| 49 | C1QL2 | complement component 1, q subcomponent-like 2 | 35528 | 3 | 3 | 3 | 0 | 1 | 0 | 0 | 1 | 0 | 1 | 0 | 0.00035 | 0.14 |
| 50 | SLC2A13 | solute carrier family 2 (facilitated glucose transporter), member 13 | 114636 | 4 | 4 | 4 | 0 | 1 | 2 | 0 | 1 | 0 | 0 | 0 | 0.00037 | 0.14 |
| 51 | NRK | Nik related kinase | 279668 | 5 | 5 | 5 | 0 | 2 | 0 | 0 | 2 | 0 | 1 | 0 | 0.00038 | 0.14 |
| 52 | FAAH2 | fatty acid amide hydrolase 2 | 115923 | 3 | 3 | 3 | 0 | 0 | 0 | 1 | 0 | 2 | 0 | 0 | 0.00039 | 0.14 |
| 53 | OR8H2 | olfactory receptor, family 8, subfamily H, member 2 | 69634 | 3 | 3 | 3 | 2 | 0 | 0 | 0 | 2 | 0 | 1 | 0 | 0.0004 | 0.14 |
| 54 | FAM135B | family with sequence similarity 135, member B | 317079 | 6 | 6 | 6 | 1 | 0 | 1 | 0 | 0 | 2 | 3 | 0 | 0.00041 | 0.14 |
| 55 | ABI3 | ABI gene family, member 3 | 52319 | 3 | 3 | 3 | 0 | 2 | 0 | 0 | 0 | 0 | 0 | 1 | 0.00042 | 0.14 |
| 56 | NFE2L2 | nuclear factor (erythroid-derived 2)-like 2 | 132201 | 4 | 4 | 3 | 0 | 0 | 3 | 0 | 0 | 1 | 0 | 0 | 0.00047 | 0.16 |
| 57 | IRF6 | interferon regulatory factor 6 | 105948 | 4 | 4 | 4 | 0 | 0 | 1 | 0 | 1 | 0 | 1 | 1 | 0.00049 | 0.16 |
| 58 | PCDH15 | protocadherin 15 | 551642 | 7 | 5 | 7 | 2 | 3 | 1 | 0 | 2 | 0 | 1 | 0 | 0.0005 | 0.16 |
| 59 | CDH12 | cadherin 12, type 2 (N-cadherin 2) | 179746 | 4 | 4 | 4 | 1 | 0 | 0 | 0 | 3 | 0 | 1 | 0 | 0.00054 | 0.17 |
| 60 | ZNF572 | zinc finger protein 572 | 118191 | 3 | 2 | 3 | 0 | 0 | 0 | 0 | 0 | 0 | 0 | 3 | 0.00056 | 0.17 |
| 61 | DDX3X | DEAD (Asp-Glu-Ala-Asp) box polypeptide 3, X-linked | 147437 | 4 | 3 | 4 | 0 | 0 | 1 | 0 | 0 | 1 | 0 | 2 | 0.00057 | 0.18 |
| 62 | PKP4 | plakophilin 4 | 267773 | 5 | 5 | 5 | 0 | 0 | 0 | 1 | 2 | 0 | 1 | 1 | 0.00058 | 0.18 |
| 63 | GPR174 | G protein-coupled receptor 174 | 73582 | 3 | 3 | 3 | 0 | 0 | 1 | 0 | 0 | 0 | 0 | 2 | 0.00059 | 0.18 |
| 64 | ADAMTS12 | ADAM metallopeptidase with thrombospondin type 1 motif, 12 | 361095 | 6 | 5 | 6 | 2 | 3 | 1 | 0 | 0 | 1 | 1 | 0 | 0.00066 | 0.19 |
| 65 | OR8K1 | olfactory receptor, family 8, subfamily K, member 1 | 71080 | 3 | 3 | 3 | 0 | 1 | 1 | 0 | 0 | 0 | 1 | 0 | 0.00066 | 0.19 |
| 66 | MEF2C | myocyte enhancer factor 2C | 106572 | 4 | 4 | 4 | 1 | 1 | 2 | 0 | 0 | 0 | 1 | 0 | 0.0007 | 0.2 |
| 67 | H3F3C | | 30439 | 2 | 2 | 2 | 0 | 0 | 0 | 0 | 0 | 0 | 2 | 0 | 0.00072 | 0.2 |
| 68 | ZNF823 | zinc finger protein 823 | 135759 | 4 | 4 | 4 | 0 | 0 | 2 | 0 | 1 | 1 | 0 | 0 | 0.00072 | 0.2 |
| 69 | LRRTM1 | leucine rich repeat transmembrane neuronal 1 | 107691 | 4 | 4 | 4 | 0 | 1 | 0 | 0 | 1 | 1 | 0 | 1 | 0.00074 | 0.2 |
| 70 | NAV3 | neuron navigator 3 | 535135 | 8 | 8 | 8 | 1 | 1 | 1 | 0 | 1 | 1 | 3 | 1 | 0.00084 | 0.22 |
| 71 | PROKR2 | prokineticin receptor 2 | 85920 | 3 | 3 | 3 | 1 | 0 | 0 | 1 | 1 | 0 | 1 | 0 | 0.00087 | 0.22 |
| 72 | KCNA6 | potassium voltage-gated channel, shaker-related subfamily, member 6 | 112736 | 4 | 4 | 4 | 1 | 1 | 1 | 1 | 0 | 0 | 0 | 1 | 0.00087 | 0.22 |
| 73 | STYK1 | serine/threonine/tyrosine kinase 1 | 96355 | 3 | 3 | 3 | 0 | 1 | 0 | 0 | 2 | 0 | 0 | 0 | 0.00087 | 0.22 |
| 74 | ANO4 | | 211459 | 5 | 5 | 5 | 0 | 0 | 2 | 0 | 1 | 1 | 1 | 0 | 0.00089 | 0.22 |
| 75 | COL1A2 | collagen, type I, alpha 2 | 299548 | 5 | 4 | 5 | 3 | 0 | 0 | 1 | 0 | 1 | 2 | 1 | 0.00089 | 0.22 |
| 76 | HIST1H4H | histone cluster 1, H4h | 23384 | 2 | 2 | 2 | 1 | 0 | 0 | 1 | 1 | 0 | 0 | 0 | 0.00091 | 0.23 |

FIG. 23

| Gene networks (Physiological system development and function) | B-H q-value | Genes |
|---|---|---|
| Hair and Skin Development and Function | 3.83E-04-5.69E-03 | CDKN2A, IRF6, TP53, COL1A2, TP63, HRAS, NOTCH1, PTEN |
| Organ Development | 3.83E-04-1.42E-02 | IRF6, TP53, CDKN2A, COL1A2, TP63, MED1, HRAS, MEF2C, CNTNAP2, CASP8, NOTCH1, PTEN |
| Organ Morphology | 3.83E-04-1.42E-02 | TP53, COL1A2, TP63, PTEN |
| Tumor Morphology | 5.05E-04-1.42E-02 | CDKN2A, TP53, HRAS, NFE2L2, NOTCH1, PTEN |
| Organismal Development | 5.58E-04-1.42E-02 | TP53, CDKN2A, NSD1, PIK3CA, TP63, MED1, PCDH15, HRAS, MLL2, PTEN, IRF6, COL1A2, MEF2C, CASP8, NFE2L2, NOTCH1 |
| Connective Tissue Development and Function | 1.42E-03-1.42E-02 | TP53, CDKN2A, TP63, DDX3X, HRAS, MEF2C, CASP8, NOTCH1, PTEN |
| Hepatic System Development and Function | 1.42E-03-1.42E-03 | TP53, MED1, HRAS, CASP8, NFE2L2 |
| Embryonic Development | 1.99E-03-1.42E-02 | CDKN2A, IRF6, TP53, NSD1, PIK3CA, TP63, MED1, HRAS, MEF2C, CASP8, NOTCH1, PTEN |
| Nervous System Development and Function | 1.99E-03-1.03E-02 | TP53, CDKN2A, HRAS, ADCY8, NOTCH1, PTEN |
| Renal and Urological System Development and Function | 1.99E-03-1.99E-03 | TP53, HRAS |
| Tissue Morphology | 2.55E-03-1.42E-02 | TP53, CDKN2A, TP63, MED1, HRAS, CASP8, NFE2L2, NOTCH1, PTEN |
| Respiratory System Development and Function | 2.75E-03-1.42E-02 | TP53, CDKN2A, HRAS, NOTCH1, NFE2L2, PTEN |
| Reproductive System Development and Function | 3.5E-03-9.3E-03 | HRAS, NOTCH1, PTEN |
| Endocrine System Development and Function | 3.5E-03-3.5E-03 | MED1, MAFA, CASP8, PTEN |
| Organismal Survival | 3.63E-03-1.42E-02 | CDKN2A, TP53, TP63, MED1, HRAS, CASP8, NFE2L2, NOTCH1, PTEN |
| Skeletal and Muscular System Development and Function | 3.63E-03-1.42E-02 | CDKN2A, IRF6, TP53, TP63, MED1, MEF2C, CASP8, NOTCH1, PTEN |
| Hematological System Development and Function | 3.84E-03-1.42E-02 | TP53, CDKN2A, TP63, MED1, HIST1H4C (includes others), HRAS, MEF2C, CASP8, NOTCH1, NFE2L2, PTEN |
| Hematopoiesis | 3.84E-03-1.42E-02 | TP53, CDKN2A, MED1, HIST1H4C (includes others), HRAS, MEF2C, CASP8, NOTCH1, NFE2L2, PTEN |
| Tissue Development | 4.08E-03-1.42E-02 | CDKN2A, IRF6, TP53, TP63, MED1, HRAS, MEF2C, NOTCH1, PTEN |
| Lymphoid Tissue Structure and Development | 1.03E-02-1.42E-02 | TP53, CDKN2A, TP63, MED1, CASP8, PTEN |
| Cardiovascular System Development and Function | 1.05E-02-1.42E-02 | TP53, COL1A2, CDKN2A, MED1, HRAS, MEF2C, CASP8, NOTCH1, PTEN |
| Cell-mediated Immune Response | 1.42E-02-1.42E-02 | TP53, CDKN2A, CASP8, NFE2L2, PTEN |
| Visual System Development and Function | 1.42E-02-1.42E-02 | USH2A, PCDH15 |
| Digestive System Development and Function | 1.42E-02-1.42E-02 | TP53 |

SEQUENCE LISTING

```
<160> NUMBER OF SEQ ID NOS: 273

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Thr Leu Asp
1


<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Thr Leu Ala
1


<210> SEQ ID NO 3
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 3

Leu Thr Gln Val
1


<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Gln His Gly
1


<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Asp His Gly
1


<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Thr Pro Asp
1


<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Gln Ala Leu Glu
1               5


<210> SEQ ID NO 8
<211> LENGTH: 4
<212> TYPE: PRT
<213> ORGANISM: Homo sapiens

<400> SEQUENCE: 8

Asp Glu Ala Asp
1


<210> SEQ ID NO 9
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Arg Ala Leu Glu
1               5


<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Thr Pro Glu
1


<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Gly Lys Gln Ala Leu Glu
1               5


<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid; This region may encompass 1-2
      residues

<400> SEQUENCE: 12

Leu Thr Pro Ala Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Asp
            20                  25                  30

His Gly


<210> SEQ ID NO 13
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Any amino acid; This region may encompass 1-2
      residues

<400> SEQUENCE: 13
```

Leu Thr Pro Ala Gln Val Val Ala Ile Ala Ser Xaa Gly Gly Lys Gln
1 5 10 15

Ala Leu Glu Thr Val Gln Arg Leu Leu Pro Val Leu Cys Gln Asp His
20 25 30

Gly

<210> SEQ ID NO 14
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (12)..(13)
<223> OTHER INFORMATION: Any amino acid; This region may encompass 1-2 residues

<400> SEQUENCE: 14

Leu Thr Pro Asp Gln Val Val Ala Ile Ala Asn Xaa Xaa Gly Gly Lys
1 5 10 15

Gln Ala Leu Ala Thr Val Gln Arg Leu Leu Pro Val Leu Cys Gln Asp
20 25 30

His Gly

<210> SEQ ID NO 15
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (12)..(13)
<223> OTHER INFORMATION: Any amino acid; This region may encompass 1-2 residues

<400> SEQUENCE: 15

Leu Thr Pro Asp Gln Val Val Ala Ile Ala Asn Xaa Xaa Gly Gly Lys
1 5 10 15

Gln Ala Leu Glu Thr Leu Gln Arg Leu Leu Pro Val Leu Cys Gln Asp
20 25 30

His Gly

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (12)..(13)
<223> OTHER INFORMATION: Any amino acid; This region may encompass 1-2 residues

<400> SEQUENCE: 16

Leu Thr Pro Asp Gln Val Val Ala Ile Ala Asn Xaa Xaa Gly Gly Lys
1 5 10 15

Gln Ala Leu Glu Thr Val Gln Arg Leu Leu Pro Val Leu Cys Gln Asp
20 25 30

His Gly

<210> SEQ ID NO 17
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (12)..(13)
<223> OTHER INFORMATION: Any amino acid; This region may encompass 1-2
residues

<400> SEQUENCE: 17

```
Leu Thr Pro Asp Gln Val Val Ala Ile Ala Ser Xaa Xaa Gly Gly Lys
1               5                   10                  15

Gln Ala Leu Ala Thr Val Gln Arg Leu Leu Pro Val Leu Cys Gln Asp
            20                  25                  30

His Gly
```

<210> SEQ ID NO 18
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (12)..(13)
<223> OTHER INFORMATION: Any amino acid; This region may encompass 1-2
residues

<400> SEQUENCE: 18

```
Leu Thr Pro Asp Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Asp
            20                  25                  30

His Gly
```

<210> SEQ ID NO 19
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (12)..(13)
<223> OTHER INFORMATION: Any amino acid; This region may encompass 1-2
residues

<400> SEQUENCE: 19

```
Leu Thr Pro Asp Gln Val Val Ala Ile Ala Ser Xaa Xaa Gly Gly Lys
1               5                   10                  15

Gln Ala Leu Glu Thr Val Gln Arg Val Leu Pro Val Leu Cys Gln Asp
            20                  25                  30

His Gly
```

<210> SEQ ID NO 20
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (12)..(13)
<223> OTHER INFORMATION: Any amino acid; This region may encompass 1-2 residues

<400> SEQUENCE: 20

```
Leu Thr Pro Glu Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly
```

<210> SEQ ID NO 21
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (12)..(13)
<223> OTHER INFORMATION: Any amino acid; This region may encompass 1-2 residues

<400> SEQUENCE: 21

```
Leu Thr Pro Tyr Gln Val Val Ala Ile Ala Ser Xaa Xaa Gly Ser Lys
1               5                   10                  15

Gln Ala Leu Glu Thr Val Gln Arg Leu Leu Pro Val Leu Cys Gln Asp
            20                  25                  30

His Gly
```

<210> SEQ ID NO 22
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (12)..(13)
<223> OTHER INFORMATION: Any amino acid; This region may encompass 1-2 residues

<400> SEQUENCE: 22

```
Leu Thr Arg Glu Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Asp
            20                  25                  30

His Gly
```

<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (12)..(13)
<223> OTHER INFORMATION: Any amino acid; This region may encompass 1-2

-continued residues

<400> SEQUENCE: 23

```
Leu Ser Thr Ala Gln Val Val Ala Ile Ala Ser Xaa Xaa Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35
```

<210> SEQ ID NO 24
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (12)..(13)
<223> OTHER INFORMATION: Any amino acid; This region may encompass 1-2 residues

<400> SEQUENCE: 24

```
Leu Ser Thr Ala Gln Val Val Ala Val Ala Ser Xaa Xaa Gly Gly Lys
1               5                   10                  15

Pro Ala Leu Glu Ala Val Arg Ala Gln Leu Leu Ala Leu Arg Ala Ala
            20                  25                  30

Pro Tyr Gly
        35
```

<210> SEQ ID NO 25
<211> LENGTH: 288
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Arg Ala Ala Gln Pro
    130                 135                 140

Ser Asp Ala Ser Pro Ala Ala Gln Val Asp Leu Arg Thr Leu Gly Tyr
145                 150                 155                 160
```

-continued

Ser Gln Gln Gln Gln Glu Lys Ile Lys Pro Lys Val Arg Ser Thr Val
165 170 175

Ala Gln His His Glu Ala Leu Val Gly His Gly Phe Thr His Ala His
180 185 190

Ile Val Ala Leu Ser Gln His Pro Ala Ala Leu Gly Thr Val Ala Val
195 200 205

Lys Tyr Gln Asp Met Ile Ala Ala Leu Pro Glu Ala Thr His Glu Ala
210 215 220

Ile Val Gly Val Gly Lys Gln Trp Ser Gly Ala Arg Ala Leu Glu Ala
225 230 235 240

Leu Leu Thr Val Ala Gly Glu Leu Arg Gly Pro Pro Leu Gln Leu Asp
245 250 255

Thr Gly Gln Leu Leu Lys Ile Ala Lys Arg Gly Gly Val Thr Ala Val
260 265 270

Glu Ala Val His Ala Trp Arg Asn Ala Leu Thr Gly Ala Pro Leu Asn
275 280 285

<210> SEQ ID NO 26
<211> LENGTH: 183
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 26

Arg Pro Ala Leu Glu Ser Ile Val Ala Gln Leu Ser Arg Pro Asp Pro
1 5 10 15

Ala Leu Ala Ala Leu Thr Asn Asp His Leu Val Ala Leu Ala Cys Leu
20 25 30

Gly Gly Arg Pro Ala Leu Asp Ala Val Lys Lys Gly Leu Pro His Ala
35 40 45

Pro Ala Leu Ile Lys Arg Thr Asn Arg Arg Ile Pro Glu Arg Thr Ser
50 55 60

His Arg Val Ala Asp His Ala Gln Val Val Arg Val Leu Gly Phe Phe
65 70 75 80

Gln Cys His Ser His Pro Ala Gln Ala Phe Asp Asp Ala Met Thr Gln
85 90 95

Phe Gly Met Ser Arg His Gly Leu Leu Gln Leu Phe Arg Arg Val Gly
100 105 110

Val Thr Glu Leu Glu Ala Arg Ser Gly Thr Leu Pro Pro Ala Ser Gln
115 120 125

Arg Trp Asp Arg Ile Leu Gln Ala Ser Gly Met Lys Arg Ala Lys Pro
130 135 140

Ser Pro Thr Ser Thr Gln Thr Pro Asp Gln Ala Ser Leu His Ala Phe
145 150 155 160

Ala Asp Ser Leu Glu Arg Asp Leu Asp Ala Pro Ser Pro Met His Glu
165 170 175

Gly Asp Gln Thr Arg Ala Ser
180

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
agctcagagg aggaggatga a 21

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ggttacaata ttgtaatggg ctc 23

<210> SEQ ID NO 29
<211> LENGTH: 9
<212> TYPE: DNA
<213> ORGANISM: Artificial Sequence
<220> FEATURE:
<223> OTHER INFORMATION: Description of Artificial Sequence: Synthetic probe

<400> SEQUENCE: 29 ccagctgga 9

<210> SEQ ID NO 30
<211> LENGTH: 13
<212> TYPE: DNA
<213> ORGANISM: Artificial Sequence
<220> FEATURE:
<223> OTHER INFORMATION: Description of Artificial Sequence: Synthetic probe

<400> SEQUENCE: 30
caagcagaac cgg 13

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
gcctgcagtt tgaaatcagt g 21

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
cgggacgggc tttagcta 18

<210> SEQ ID NO 33
<211> LENGTH: 9
<212> TYPE: DNA
<213> ORGANISM: Artificial Sequence
<220> FEATURE:
<223> OTHER INFORMATION: Description of Artificial Sequence: Synthetic probe

<400> SEQUENCE: 33 tggaagcta 9

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic probe

<400> SEQUENCE: 34
atgggaagcc cagtacc 17

<210> SEQ ID NO 35
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
tttattccct gacc 14

<210> SEQ ID NO 36
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

Leu Thr Pro Glu Gln Val Val Ala Ile Ala Ser Asn Gly Gly Gly Lys
1 5 10 15

Gln Ala Leu Glu Thr Val Gln Arg Leu Leu Pro Val Leu Cys Gln Ala
20 25 30

His Gly

<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Leu Thr Pro Asp Gln Val Val Ala Ile Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 38
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

Leu Thr Pro Glu Gln Val Val Ala Ile Ala Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

Leu Thr Pro Asp Gln Val Val Ala Ile Ala Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

Leu Thr Pro Ala Gln Val Val Ala Ile Ala Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

Leu Thr Pro Ala Gln Val Val Ala Ile Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Leu Thr Pro Asp Gln Val Val Ala Ile Ala Ser Gly Gly Lys Gln Ala
1 5 10 15

Leu Glu Thr Val Gln Arg Leu Leu Pro Val Leu Cys Glu Gln His Gly
20 25 30

<210> SEQ ID NO 43
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

Leu Thr Pro Asp Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Leu Thr Pro Gln Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

Leu Thr Pro Asp Gln Val Val Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

Leu Thr Pro Asn Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

```
<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30


<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Leu Thr Pro Ala Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30


<210> SEQ ID NO 50
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Leu Thr Pro Glu Gln Val Val Ala Ile Ala Ser Gly Gly Lys Gln Ala
1               5                   10                  15

Leu Glu Thr Val Gln Ala Leu Leu Pro Val Leu Cys Gln Ala His Gly
            20                  25                  30


<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Leu Thr Leu Asp Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
            20                  25                  30


<210> SEQ ID NO 52
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Leu Thr Gln Asp Gln Val Val Ala Ile Ala Ser Gly Gly Lys Gln Ala
```

1 5 10 15

Leu Glu Thr Val Gln Arg Leu Leu Pro Val Leu Cys Gln Asp His Gly
20 25 30

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

Leu Ser Pro Asp Gln Val Val Ala Ile Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 54
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

Leu Thr Pro Asp Gln Val Val Ala Ile Ala Asn Gly Gly Lys Gln Ala
1 5 10 15

Leu Glu Thr Leu Gln Arg Leu Leu Pro Val Leu Cys Gln Asp His Gly
20 25 30

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

Leu Thr Pro Asp Gln Val Val Ala Ile Ala Ser Gly Gly Lys Gln Ala
1 5 10 15

Leu Glu Thr Leu Gln Arg Leu Leu Pro Val Leu Cys Gln Asp His Gly
20 25 30

<210> SEQ ID NO 56
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

Leu Thr Pro Asp Gln Val Val Ala Ile Ala Ser Gly Gly Lys Gln Ala
1 5 10 15

Leu Glu Thr Val Gln Arg Leu Leu Pro Val Leu Arg Gln Ala His Gly
20 25 30

<210> SEQ ID NO 57
<211> LENGTH: 32
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 57

Leu Thr Pro Asp Gln Val Val Ala Ile Ala Ser Gly Gly Asn Gln Ala
1               5                   10                  15

Leu Glu Thr Val Gln Arg Leu Leu Pro Val Leu Cys Gln Ala His Gly
            20                  25                  30


<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Leu Thr Pro Asp Gln Val Val Ala Ile Ala Ser Gly Gly Lys Gln Ala
1               5                   10                  15

Leu Ala Thr Val Gln Arg Leu Leu Pro Val Leu Cys Gln Ala His Gly
            20                  25                  30


<210> SEQ ID NO 59
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Leu Thr Pro Ala Gln Val Val Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30


<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Leu Thr Leu Ala Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30


<210> SEQ ID NO 61
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Leu Thr Pro Glu Gln Val Val Ala Ile Ala Cys Gly Gly Lys Gln Ala
1               5                   10                  15

Leu Glu Thr Val Gln Arg Leu Leu Pro Val Leu Cys Gln Ala His Gly
            20                  25                  30
```

-continued

<210> SEQ ID NO 62
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

```
Leu Thr Pro Ala Gln Val Val Ala Ile Ala Ser Gly Gly Lys Gln Ala
1               5                   10                  15

Leu Glu Thr Val Gln Gln Leu Leu Pro Val Leu Cys Glu Gln His Gly
            20                  25                  30
```

<210> SEQ ID NO 63
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

```
Leu Thr Pro Gln Gln Val Val Ala Ile Ala Ser Gly Gly Arg Pro Ala
1               5                   10                  15

Leu Glu Thr Val Gln Arg Leu Leu Pro Val Leu Cys Gln Ala His Gly
            20                  25                  30
```

<210> SEQ ID NO 64
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

```
Leu Thr Pro Asp Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
            20                  25                  30
```

<210> SEQ ID NO 65
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

```
Leu Thr Pro Asn Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30
```

<210> SEQ ID NO 66
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Leu Thr Pro Asp Gln Val Val Ala Ile Ala Ser Gly Gly Lys Gln Ala
1               5                   10                  15

Leu Gly Thr Val Gln Arg Leu Leu Pro Val Leu Cys Gln Asp His Gly
            20                  25                  30


<210> SEQ ID NO 67
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Leu Thr Leu Ala Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30


<210> SEQ ID NO 68
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Leu Thr Pro Ala Gln Ala Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30


<210> SEQ ID NO 69
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Leu Thr Pro Ala Gln Val Val Ala Ile Ala Ser Gly Gly Asn Gln Ala
1               5                   10                  15

Leu Glu Thr Val Gln Arg Leu Leu Pro Val Leu Cys Gln Asp His Gly
            20                  25                  30


<210> SEQ ID NO 70
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Leu Thr Pro Asp Gln Val Val Ala Ile Ala Ser Gly Gly Lys Gln Ala
1               5                   10                  15

Leu Glu Thr Leu Gln Arg Leu Leu Pro Val Leu Cys Gln Ala His Gly
            20                  25                  30


<210> SEQ ID NO 71
<211> LENGTH: 32
<212> TYPE: PRT
<213> ORGANISM: Artificial Sequence
```

<220> FEATURE:
<223> OTHER INFORMATION: Description of Artificial Sequence: Synthetic
polypeptide

<400> SEQUENCE: 71

```
Leu Thr Pro Asp Gln Val Val Ala Ile Ala Asn Gly Gly Lys Gln Ala
1               5                   10                  15

Leu Glu Thr Leu Gln Arg Leu Leu Pro Val Leu Cys Gln Ala His Gly
            20                  25                  30
```

<210> SEQ ID NO 72
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 72

```
Leu Thr Pro Asp Gln Val Val Thr Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 73
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 73

```
Leu Thr Pro Ala Gln Val Val Ala Ile Ala Asn Gly Gly Lys Gln Ala
1               5                   10                  15

Leu Glu Thr Val Arg Arg Leu Leu Pro Val Leu Cys Gln Asp His Gly
            20                  25                  30
```

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 74

```
Leu Thr Pro Asp Gln Val Val Ala Ile Ala Ser Gly Gly Asn Gln Ala
1               5                   10                  15

Leu Glu Thr Val Gln Arg Leu Leu Pro Val Leu Cys Gln Asp His Gly
            20                  25                  30
```

<210> SEQ ID NO 75
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 75

```
Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Thr His Gly
            20                  25                  30
```

<210> SEQ ID NO 76
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 76

```
Leu Pro Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 77
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 77

```
Leu Thr Ser Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 78
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 78

```
Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Glu Gln His Gly
            20                  25                  30
```

<210> SEQ ID NO 79
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 79

```
Leu Ile Pro Ala Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 80
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 80

```
Leu Thr Pro Ala Gln Val Val Ala Ile Ala Ser Gly Gly Lys Gln Ala
1               5                   10                  15

Leu Glu Thr Met Gln Arg Leu Leu Pro Val Leu Cys Gln Ala His Gly
            20                  25                  30


<210> SEQ ID NO 81
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Leu Thr Arg Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30


<210> SEQ ID NO 82
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Leu Thr Pro Asp Gln Val Val Ala Thr Ala Ser Gly Gly Lys Gln Ala
1               5                   10                  15

Leu Glu Thr Val Gln Arg Leu Leu Pro Val Leu Cys Gln Asp His Gly
            20                  25                  30


<210> SEQ ID NO 83
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Leu Ile Pro Asp Gln Val Val Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30


<210> SEQ ID NO 84
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asn His Gly
            20                  25                  30


<210> SEQ ID NO 85
<211> LENGTH: 32
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 85

```
Leu Thr Leu Asp Gln Val Val Ala Ile Ala Ser Gly Gly Lys Lys Ala
1               5                   10                  15

Leu Glu Thr Val Gln Arg Leu Leu Pro Val Leu Cys Gln Asp His Gly
            20                  25                  30
```

<210> SEQ ID NO 86
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 86

```
Leu Thr Pro Asp Gln Leu Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 87
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 87

```
Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Gly His Gly
            20                  25                  30
```

<210> SEQ ID NO 88
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 88

```
Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Glu His Gly
            20                  25                  30
```

<210> SEQ ID NO 89
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 89

```
Leu Thr Leu Asp Lys Val Val Ala Ile Ala Ser Gly Gly Lys Gln Ala
1               5                   10                  15

Leu Glu Thr Val Gln Arg Leu Leu Pro Val Leu Cys Gln Asp His Gly
```

20 25 30

<210> SEQ ID NO 90
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

Leu Thr Pro Ala Gln Val Val Ala Ile Ala Ser Gly Ser Lys Gln Ala
1 5 10 15

Leu Glu Thr Val Gln Arg Leu Leu Pro Val Leu Cys Gln Ala His Gly
20 25 30

<210> SEQ ID NO 91
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

Leu Thr Pro Asp Lys Val Val Ala Ile Ala Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 92
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

Leu Thr Gln Asp Gln Val Val Ala Ile Ala Ser Gly Gly Lys Gln Ala
1 5 10 15

Leu Glu Thr Val Gln Arg Leu Leu Pro Val Leu Tyr Gln Asp His Gly
20 25 30

<210> SEQ ID NO 93
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Leu Thr Pro Ala Gln Val Val Ala Ile Val Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 94
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide -continued

<400> SEQUENCE: 94

```
Leu Thr Pro Asp Lys Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 95
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

```
Leu Thr Gln Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30
```

<210> SEQ ID NO 96
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

```
Leu Thr Pro Asp Gln Val Met Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 97
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

```
Leu Thr Thr Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30
```

<210> SEQ ID NO 98
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

```
Leu Thr Pro Asp Gln Val Val Ala Ile Ala Ser Gly Ser Lys Gln Ala
1               5                   10                  15

Leu Glu Thr Val Gln Arg Leu Leu Pro Val Leu Cys Gln Ala His Gly
            20                  25                  30
```

<210> SEQ ID NO 99
<211> LENGTH: 32

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

Leu Thr Pro Asp Gln Val Val Ala Ile Ala Asn Gly Gly Lys Gln Ala
1 5 10 15

Leu Glu Thr Val Gln Arg Leu Leu Leu Val Leu Cys Gln Ala His Gly
20 25 30

<210> SEQ ID NO 100
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

Leu Thr Gln Glu Gln Val Val Ala Ile Ala Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 101
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

Leu Thr Pro Asp Gln Val Val Thr Ile Ala Asn Gly Gly Lys Gln Ala
1 5 10 15

Leu Glu Thr Val Gln Arg Leu Leu Pro Val Leu Cys Gln Ala His Gly
20 25 30

<210> SEQ ID NO 102
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

Leu Ser Pro Ala Gln Val Val Ala Ile Ala Ser Gly Gly Lys Gln Ala
1 5 10 15

Leu Glu Thr Val Gln Arg Leu Leu Pro Val Leu Cys His Asp His Gly
20 25 30

<210> SEQ ID NO 103
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

Leu Thr Pro Asp Gln Val Val Ala Ile Ala Ser Gly Gly Lys Gln Ala
1 5 10 15

```
Leu Glu Met Val Gln Arg Leu Leu Pro Val Leu Cys Gln Ala His Gly
            20                  25                  30


<210> SEQ ID NO 104
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Leu Ile Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30


<210> SEQ ID NO 105
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Leu Thr Pro Val Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30


<210> SEQ ID NO 106
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Leu Thr Pro Asp Gln Val Val Ala Ile Ala Ser Gly Gly Lys Gln Ala
1               5                   10                  15

Leu Lys Thr Val Gln Arg Leu Leu Pro Val Leu Cys Gln Asp His Gly
            20                  25                  30


<210> SEQ ID NO 107
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Leu Thr Pro Asp Gln Val Val Ala Ile Ala Ser Gly Gly Lys Gln Ala
1               5                   10                  15

Leu Glu Thr Met Gln Arg Leu Leu Pro Val Leu Cys Gln Ala His Gly
            20                  25                  30


<210> SEQ ID NO 108
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 108

Leu Thr Pro Ala Gln Val Val Ala Ile Ala Ser Gly Gly Lys Gln Ala
1 5 10 15

Leu Glu Thr Val Gln Arg Leu Phe Pro Val Leu Cys Gln Asp His Gly
20 25 30

<210> SEQ ID NO 109
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Leu Thr Pro Ala Gln Val Val Ala Ile Ala Ser Gly Gly Lys Gln Ala
1 5 10 15

Leu Glu Thr Val Gln Gln Leu Leu Pro Val Leu Cys Gln Ala His Gly
20 25 30

<210> SEQ ID NO 110
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

Leu Thr Pro Ala Gln Val Val Ala Leu Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 111
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

Leu Thr Pro Asp Gln Val Val Ala Ile Ala Ser Gly Gly Arg Pro Ala
1 5 10 15

Leu Glu Thr Val Gln Arg Leu Leu Pro Val Leu Cys Glu Gln His Gly
20 25 30

<210> SEQ ID NO 112
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

Leu Thr Pro Asp Gln Val Val Ala Ile Ala Ser Gly Gly Lys Gln Ala
1 5 10 15

Leu Ala Thr Val Gln Arg Leu Leu Pro Val Leu Cys Gln Asp His Gly
20 25 30

<210> SEQ ID NO 113

<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

Leu Thr Gln Val Gln Val Val Ala Ile Ala Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 114
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

Leu Thr Pro Asp Gln Val Val Ala Ile Ala Arg Gly Gly Lys Gln Ala
1 5 10 15

Leu Glu Thr Val Gln Arg Leu Leu Pro Val Leu Cys Gln Ala His Gly
20 25 30

<210> SEQ ID NO 115
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

Leu Pro Pro Asp Gln Val Val Ala Ile Ala Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 116
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 116

Leu Thr Leu Asp Gln Val Val Ala Ile Ala Ser Gly Ser Lys Gln Ala
1 5 10 15

Leu Glu Thr Val Gln Arg Leu Leu Pro Val Leu Cys Gln Ala His Gly
20 25 30

<210> SEQ ID NO 117
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

Leu Ser Pro Asp Gln Val Val Ala Ile Ala Asn Gly Gly Lys Gln Ala
1 5 10 15

Leu Glu Thr Leu Gln Arg Leu Leu Pro Val Leu Cys Gln Thr His Ala
20 25 30

<210> SEQ ID NO 118
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 118

Leu Asn Pro Asp Gln Val Val Ala Ile Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 119
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 119

Leu Thr Pro Asp Gln Val Met Ala Ile Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 120
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

Leu Thr Pro Ala Gln Val Val Ala Ile Ala Ser Gly Gly Lys Gln Ala
1 5 10 15

Leu Glu Thr Val Arg Arg Leu Leu Pro Val Leu Cys Gln Ala His Gly
20 25 30

<210> SEQ ID NO 121
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

Leu Thr Pro Asp Gln Val Val Ala Ile Ala Ser Gly Gly Lys Gln Thr
1 5 10 15

Leu Glu Thr Val Gln Arg Leu Leu Pro Val Leu Cys Gln Asp His Gly
20 25 30

<210> SEQ ID NO 122
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

Leu Thr Pro Asp Gln Val Met Thr Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 123
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Leu Thr Pro Ala Gln Val Val Thr Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 124
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Arg Ala His Gly
            20                  25                  30

<210> SEQ ID NO 125
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Leu Ser Pro Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 126
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Leu Thr Pro Asp Gln Val Val Gly Ile Ala Ser Gly Gly Lys Gln Ala
1               5                   10                  15

Leu Glu Thr Val Gln Arg Leu Leu Pro Val Leu Cys Gln Asp His Gly
            20                  25                  30

-continued

<210> SEQ ID NO 127
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 127

Leu Thr Pro Asp Gln Val Val Ala Ile Ala Ser Gly Gly Lys Gln Ala
1 5 10 15

Leu Glu Thr Val Gln Arg Leu Leu Pro Val Leu Cys Gln Ala Asn Gly
20 25 30

<210> SEQ ID NO 128
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 128

Leu Thr Pro Ala Gln Val Val Ala Ile Ala Ser Gly Gly Lys Gln Ala
1 5 10 15

Leu Glu Thr Val Gln Arg Leu Leu Pro Val Leu Cys Gln Thr His Gly
20 25 30

<210> SEQ ID NO 129
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 129

Leu Thr Pro Asp Gln Val Val Ala Ile Ala Ser Gly Gly Lys Gln Ala
1 5 10 15

Leu Glu Met Val Gln Arg Leu Leu Pro Val Leu Cys Gln Asp His Gly
20 25 30

<210> SEQ ID NO 130
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 130

Leu Thr Pro Asp Gln Val Val Ala Ile Ala Ser Gly Gly Lys Gln Ala
1 5 10 15

Leu Glu Thr Met Gln Arg Leu Leu Pro Val Leu Cys Gln Asp His Gly
20 25 30

<210> SEQ ID NO 131
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 131

Leu Thr Pro Asp Gln Val Val Ala Ile Ala Asn Gly Gly Lys Gln Ala 1 5 10 15

Leu Ala Thr Val Gln Arg Leu Leu Pro Val Leu Cys Gln Asp His Gly
20 25 30

<210> SEQ ID NO 132
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 132

Leu Thr Pro Asp Gln Val Val Thr Ile Ala Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 133
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

Leu Thr Pro Asp Gln Val Val Ala Ile Ala Ser Gly Gly Lys Gln Ala
1 5 10 15

Leu Glu Thr Val Gln Arg Leu Leu Thr Val Leu Cys Gln Asp His Gly
20 25 30

<210> SEQ ID NO 134
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

Met Thr Pro Asp Gln Val Val Ala Ile Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 135
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 135

Leu Ala Pro Asp Gln Val Val Ala Val Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 136
<211> LENGTH: 32
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 136

Leu Thr Pro Ala Gln Val Val Ala Ile Ala Ser Gly Gly Lys Gln Ala
1               5                   10                  15

Leu Lys Thr Val Gln Gln Leu Leu Pro Val Leu Cys Glu Gln His Gly
            20                  25                  30


<210> SEQ ID NO 137
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Leu Thr Pro Asp Gln Val Val Ala Ile Ala Arg Gly Gly Lys Gln Ala
1               5                   10                  15

Leu Glu Thr Val Gln Arg Leu Leu Pro Val Leu Cys Gln Asp His Gly
            20                  25                  30


<210> SEQ ID NO 138
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Leu Thr Pro Asp Gln Val Val Ala Ile Ala Ser Gly Gly Lys Gln Ala
1               5                   10                  15

Leu Glu Thr Val Gln Gln Leu Leu Pro Val Leu Cys Gln Ala His Gly
            20                  25                  30


<210> SEQ ID NO 139
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Leu Thr Pro Asp Gln Val Leu Ala Ile Ala Ser Gly Gly Lys Gln Ala
1               5                   10                  15

Leu Glu Thr Leu Gln Arg Leu Leu Pro Val Leu Cys Gln Asp His Gly
            20                  25                  30


<210> SEQ ID NO 140
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Leu Thr Pro Glu Gln Val Val Ala Ile Ala Arg Gly Gly Lys Gln Ala
1               5                   10                  15

Leu Glu Thr Val Gln Arg Leu Leu Pro Val Leu Cys Gln Ala His Gly
            20                  25                  30
```

<210> SEQ ID NO 141
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 141

```
Leu Thr Pro Ala Gln Val Val Ala Ile Ala Ser Gly Gly Lys Gln Ala
1               5                   10                  15

Leu Glu Thr Met Gln Arg Leu Leu Pro Val Leu Cys Arg Ala His Gly
            20                  25                  30
```

<210> SEQ ID NO 142
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 142

```
Leu Thr Pro Asp Gln Val Val Ala Ile Ala Asn Gly Gly Lys Gln Ala
1               5                   10                  15

Leu Glu Met Val Gln Arg Leu Leu Pro Val Leu Cys Gln Asp His Gly
            20                  25                  30
```

<210> SEQ ID NO 143
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 143

```
Leu Thr Thr Asp Gln Val Val Thr Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 144
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 144

```
Leu Thr Pro Thr Gln Val Met Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 145
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 145

```
Leu Thr Pro Gln Gln Val Val Ala Ile Ala Ser Gly Gly Lys Gln Ala
1               5                   10                  15

Leu Glu Thr Val Gln Ala Leu Leu Pro Val Leu Cys Gln Ala His Gly
            20                  25                  30


<210> SEQ ID NO 146
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Leu Thr Pro Asp Gln Val Val Ala Ile Ala Ser Gly Gly Lys Gln Ala
1               5                   10                  15

Leu Glu Thr Val Gln Arg Leu Leu Pro Met Leu Cys Gln Asp His Gly
            20                  25                  30


<210> SEQ ID NO 147
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Leu Thr Ser Ala Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30


<210> SEQ ID NO 148
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Leu Thr Pro Asp Gln Val Val Ala Ile Ala Ser Gly Gly Lys Gln Ala
1               5                   10                  15

Leu Glu Thr Val Gln Gln Leu Leu Pro Val Leu Cys Gln Asp His Gly
            20                  25                  30


<210> SEQ ID NO 149
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Leu Thr Pro Asp Gln Val Val Ala Ile Ala Asn Gly Gly Lys Gln Ala
1               5                   10                  15

Leu Ala Thr Val Gln Arg Leu Leu Pro Val Leu Cys Gln Ala His Gly
            20                  25                  30


<210> SEQ ID NO 150
<211> LENGTH: 32
<212> TYPE: PRT
<213> ORGANISM: Artificial Sequence
```

<220> FEATURE:
<223> OTHER INFORMATION: Description of Artificial Sequence: Synthetic polypeptide

<400> SEQUENCE: 150

```
Leu Thr Pro Ala Gln Val Val Ala Ile Ala Ser Gly Gly Lys Gln Ala
1               5                   10                  15

Leu Glu Thr Val Gln Arg Leu Leu Pro Met Leu Cys Gln Ala His Gly
            20                  25                  30
```

<210> SEQ ID NO 151
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 151

```
Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Gln Ala Arg Gly
            20                  25                  30
```

<210> SEQ ID NO 152
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 152

```
Leu Thr Pro Ala Gln Val Val Ala Ile Ala Ser Gly Gly Lys Gln Ala
1               5                   10                  15

Leu Glu Thr Leu Gln Arg Leu Leu Pro Val Leu Cys Gln Asp His Gly
            20                  25                  30
```

<210> SEQ ID NO 153
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 153

```
Leu Thr Pro Asp Gln Val Val Ala Ile Ala Asn Gly Gly Lys Gln Ala
1               5                   10                  15

Leu Glu Thr Val Gln Arg Leu Leu Pro Val Leu Cys Gln Asn His Gly
            20                  25                  30
```

<210> SEQ ID NO 154
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 154

```
Leu Thr Pro Asp Gln Val Val Thr Ile Ala Ser Gly Gly Lys Gln Ala
1               5                   10                  15

Leu Glu Met Val Gln Arg Leu Leu Pro Val Leu Cys Gln Asp His Gly
            20                  25                  30
```

<210> SEQ ID NO 155
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 155

```
Leu Thr Pro Asp Gln Val Val Ala Ile Ala Ser Gly Gly Lys Gln Ala
1               5                   10                  15

Leu Glu Arg Val Gln Arg Leu Leu Pro Val Leu Cys Glu Gln His Gly
            20                  25                  30
```

<210> SEQ ID NO 156
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 156

```
Leu Thr Pro Glu Gln Val Val Ala Ile Ala Cys Gly Gly Lys Gln Ala
1               5                   10                  15

Leu Glu Thr Val Gln Ala Leu Leu Pro Val Leu Arg Gln Ala His Gly
            20                  25                  30
```

<210> SEQ ID NO 157
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 157

```
Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Arg Asp His Gly
            20                  25                  30
```

<210> SEQ ID NO 158
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 158

```
Leu Thr Pro Glu Gln Val Val Ala Ile Ala Ser Gly Gly Lys Gln Ala
1               5                   10                  15

Leu Glu Thr Val Gln Arg Leu Leu Pro Met Leu Cys Gln Ala His Gly
            20                  25                  30
```

<210> SEQ ID NO 159
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 159

```
Leu Thr Pro Glu Gln Val Val Ala Ile Ala Cys Gly Gly Lys Gln Ala
1               5                   10                  15

Leu Glu Thr Val Gln Arg Leu Leu Pro Val Leu Arg His Ala His Gly
            20                  25                  30


<210> SEQ ID NO 160
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln His His Gly
            20                  25                  30


<210> SEQ ID NO 161
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Leu Ile Pro Asp Gln Val Val Ala Ile Ala Ser Gly Gly Lys Gln Ala
1               5                   10                  15

Leu Glu Thr Val Gln Arg Leu Leu Pro Val Leu Cys Gln His His Gly
            20                  25                  30


<210> SEQ ID NO 162
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Leu Thr Arg Ala Gln Val Val Ala Ile Ala Ser Gly Gly Lys Gln Ala
1               5                   10                  15

Leu Glu Thr Val Gln Arg Leu Leu Pro Val Leu Cys Glu Gln His Gly
            20                  25                  30


<210> SEQ ID NO 163
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Leu Thr Pro Asp Gln Val Val Ala Ile Ala Asn Gly Gly Lys Gln Ala
1               5                   10                  15

Val Gly Thr Val Gln Arg Leu Leu Pro Val Leu Cys Gln Ala His Gly
            20                  25                  30


<210> SEQ ID NO 164
<211> LENGTH: 32
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 164

```
Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Glu Gln His Gly
            20                  25                  30
```

<210> SEQ ID NO 165
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 165

```
Leu Thr Pro Ala Gln Val Val Ala Ile Ala Ser Gly Gly Lys Gln Ala
1               5                   10                  15

Leu Glu Thr Val Gln Arg Leu Leu Pro Met Leu Cys Gln Asp His Gly
            20                  25                  30
```

<210> SEQ ID NO 166
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 166

```
Leu Thr Pro Asp Gln Val Val Ala Ile Ala Ser Gly Ser Lys Gln Ala
1               5                   10                  15

Leu Glu Thr Met Gln Arg Leu Leu Pro Val Leu Cys Gln Asp His Gly
            20                  25                  30
```

<210> SEQ ID NO 167
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 167

```
Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Lys Gln His Gly
            20                  25                  30
```

<210> SEQ ID NO 168
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 168

```
Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Gln Thr His Gly
```

20 25 30

<210> SEQ ID NO 169
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 169

Leu Thr Pro Asp Gln Val Val Ala Ile Ala Ser Gly Gly Lys Gln Ala
1 5 10 15

Leu Glu Ala Val Gln Arg Leu Leu Pro Val Leu Cys Gln Asp His Gly
20 25 30

<210> SEQ ID NO 170
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 170

Leu Thr Pro Ala Gln Val Val Thr Ile Ala Ser Gly Gly Lys Gln Ala
1 5 10 15

Leu Glu Thr Val Gln Arg Leu Leu Pro Val Leu Cys Glu Gln His Gly
20 25 30

<210> SEQ ID NO 171
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 171

Leu Thr Pro Ala Gln Val Met Ala Ile Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 172
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

Leu Thr Arg Glu Gln Val Val Ala Ile Ala Ser Gly Gly Lys Gln Ala
1 5 10 15

Leu Glu Thr Val Gln Arg Leu Leu Pro Val Leu Arg Gln Ala His Gly
20 25 30

<210> SEQ ID NO 173
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 173

Leu Thr Leu Ala Gln Val Val Ala Ile Ala Asn Gly Gly Lys Gln Ala
1 5 10 15

Leu Glu Thr Val Gln Arg Leu Leu Pro Val Leu Cys Gln Ala His Gly
20 25 30

<210> SEQ ID NO 174
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 174

Leu Thr Leu Glu Gln Val Val Ala Ile Ala Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 175
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 175

Leu Thr Pro Gln Gln Val Val Ala Ile Ala Ser Gly Gly Lys Gln Ala
1 5 10 15

Leu Glu Thr Val Gln Arg Leu Leu Pro Val Leu Cys Glu Gln His Gly
20 25 30

<210> SEQ ID NO 176
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 176

Leu Ser Pro Asp Gln Val Val Ala Ile Ala Asn Gly Gly Lys Gln Ala
1 5 10 15

Leu Glu Thr Val Gln Arg Leu Leu Pro Val Leu Cys Gln Asp His Gly
20 25 30

<210> SEQ ID NO 177
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 177

Leu Thr Pro Asp Gln Val Val Ala Ile Ala Asn Gly Gly Lys Gln Ala
1 5 10 15

Leu Glu Thr Val Gln Arg Leu Leu Pro Val Leu Cys Gln His His Gly
20 25 30

<210> SEQ ID NO 178
<211> LENGTH: 32

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 178

Leu Thr Pro Glu Gln Val Val Ala Ile Ala Ser Gly Gly Lys Gln Ala
1 5 10 15

Leu Glu Thr Val Gln Ala Leu Leu Pro Val Leu Arg Gln Ala His Gly
20 25 30

<210> SEQ ID NO 179
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 179

Leu Ser Gln Asp Gln Val Val Ala Ile Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 180
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

Leu Pro Pro Glu Gln Val Val Ala Ile Ala Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 181
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 181

Leu Thr Pro Asp Gln Val Val Ala Ile Ala Ser Gly Gly Lys Gln Ala
1 5 10 15

Leu Glu Ala Val Gln Arg Leu Leu Pro Val Leu Cys Gln Ala His Gly
20 25 30

<210> SEQ ID NO 182
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

Leu Thr Pro Asp Gln Val Val Ala Ile Ala Asn Gly Gly Lys Gln Ala
1 5 10 15

-continued

```
Leu Glu Thr Val Gln Arg Leu Leu Pro Val Leu Cys Gln Glu His Gly
            20                  25                  30


<210> SEQ ID NO 183
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Leu Thr Leu Asp Gln Val Ala Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30


<210> SEQ ID NO 184
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Leu Thr Pro Asp Gln Val Val Ala Ile Ala Ser Gly Gly Lys Gln Ala
1               5                   10                  15

Leu Glu Thr Val Gln Arg Val Leu Pro Val Leu Cys Gln Asp His Gly
            20                  25                  30


<210> SEQ ID NO 185
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Leu Ile Pro Ala Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30


<210> SEQ ID NO 186
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Arg Gln Ala His Gly
            20                  25                  30


<210> SEQ ID NO 187
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 187

Leu Thr Pro Ala Gln Val Val Ala Ile Ala Ser Gly Ser Lys Gln Ala
1 5 10 15

Leu Glu Thr Val Gln Arg Leu Leu Pro Val Leu Cys Gln Thr His Gly
20 25 30

<210> SEQ ID NO 188
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 188

Leu Thr Pro Gln Gln Val Val Ala Ile Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 189
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 189

Leu Thr Pro Asp Gln Val Val Ala Ile Ala Asn Gly Gly Lys Gln Ala
1 5 10 15

Val Glu Thr Val Gln Arg Leu Leu Pro Val Leu Cys Gln Ala His Gly
20 25 30

<210> SEQ ID NO 190
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 190

Leu Ser Pro Asp Gln Val Val Thr Ile Ala Ser Gly Gly Lys Gln Ala
1 5 10 15

Leu Glu Thr Leu Gln Arg Leu Leu Pro Val Leu Cys Gln Asp His Gly
20 25 30

<210> SEQ ID NO 191
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 191

Leu Thr Pro Val Gln Val Val Ala Ile Ala Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 192

<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 192

Leu Thr Leu Asp Gln Val Val Ala Ile Ala Ser Gly Ser Lys Gln Ala
1 5 10 15

Leu Glu Thr Val Gln Arg Leu Leu Pro Val Leu Cys Gln Thr His Gly
20 25 30

<210> SEQ ID NO 193
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 193

Leu Thr Pro Ala Gln Val Val Ala Ile Ala Cys Gly Gly Lys Gln Ala
1 5 10 15

Leu Glu Thr Val Arg Arg Leu Leu Pro Val Leu Cys Gln Ala His Gly
20 25 30

<210> SEQ ID NO 194
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 194

Leu Thr Pro Ala Gln Val Val Ala Ile Ala Ser Gly Ser Lys Gln Ala
1 5 10 15

Leu Glu Thr Val Gln Arg Leu Phe Pro Val Leu Cys Gln Ala His Gly
20 25 30

<210> SEQ ID NO 195
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 195

Leu Pro Pro Ala Gln Val Val Ala Ile Ala Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 196
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 196

Leu Thr Pro Asp Gln Val Val Ala Ile Ala Ser Gly Gly Lys Gln Ala
1 5 10 15

Leu Glu Thr Val Gln Arg Leu Leu Pro Val Leu Phe Gln Glu His Gly
20 25 30

<210> SEQ ID NO 197
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 197

Leu Thr Pro Ala Lys Val Val Ala Ile Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 198
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 198

Leu Thr Pro Val Gln Val Val Ala Ile Ala Ser Gly Gly Lys Gln Ala
1 5 10 15

Leu Ala Thr Val Gln Arg Leu Leu Pro Val Leu Cys Gln Asp His Gly
20 25 30

<210> SEQ ID NO 199
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 199

Leu Thr Pro Asp Gln Val Val Ala Ile Ala Ser Gly Gly Lys Gln Ala
1 5 10 15

Leu Glu Thr Val Gln Arg Leu Leu Pro Gly Leu Cys Gln Asp His Gly
20 25 30

<210> SEQ ID NO 200
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 200

Leu Thr Leu Ala Gln Val Val Ala Ile Ala Asn Gly Gly Lys Gln Ala
1 5 10 15

Leu Glu Thr Val Gln Arg Leu Leu Pro Val Leu Cys Gln Asp His Gly
20 25 30

<210> SEQ ID NO 201
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 201

Leu Thr Pro Ala Gln Val Val Ala Ile Ala Ser Gly Gly Lys Gln Ala
1 5 10 15

Leu Glu Thr Val Gln Arg Leu Leu Thr Val Leu Cys Gln Asp His Gly
20 25 30

<210> SEQ ID NO 202
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 202

Leu Pro Pro Ala Gln Val Val Ala Ile Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 203
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 203

Leu Thr Pro Ala Gln Ala Val Ala Ile Ala Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 204
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 204

Leu Thr Pro Ala Gln Val Val Ala Ile Val Ser Gly Gly Lys Gln Ala
1 5 10 15

Leu Glu Thr Val Gln Arg Leu Leu Pro Val Leu Cys Gln Thr His Gly
20 25 30

<210> SEQ ID NO 205
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 205

Leu Thr Pro Asp Gln Val Val Ala Val Ala Gly Gly Gly Lys Gln Ala
1 5 10 15

Leu Glu Thr Val Gln Arg Leu Leu Pro Val Leu Cys Gln Asp His Gly
20 25 30

<210> SEQ ID NO 206
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 206

Leu Thr Pro Asp Gln Val Val Ala Ile Ala Ser Gly Gly Lys Gln Ala
1 5 10 15

Leu Gly Thr Val Gln Arg Leu Leu Pro Val Leu Cys Gln Ala His Gly
20 25 30

<210> SEQ ID NO 207
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 207

Leu Pro Pro Ala Gln Val Val Ala Ile Ala Ser Gly Gly Lys Gln Ala
1 5 10 15

Leu Glu Thr Val Gln Arg Leu Leu Pro Val Leu Cys Glu Ala His Gly
20 25 30

<210> SEQ ID NO 208
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 208

Leu Thr Thr Asp Gln Val Val Ala Ile Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 209
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 209

Leu Thr Pro Asp Gln Val Val Ala Ile Ala Asn Gly Gly Lys Gln Ala
1 5 10 15

Leu Glu Thr Val Gln Arg Leu Val Pro Val Leu Cys Gln Asp His Gly
20 25 30

<210> SEQ ID NO 210
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 210

Leu Thr Pro Asp Gln Val Val Ala Ile Ala Ser Gly Gly Lys Gln Ala 1 5 10 15

Leu Glu Thr Val Gln Arg Leu Leu Pro Val Leu Cys Gln Thr His Ala
20 25 30

<210> SEQ ID NO 211
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 211

Leu Thr Leu Ala Gln Val Val Ala Ile Ala Ser Gly Gly Lys Gln Ala
1 5 10 15

Leu Glu Thr Val Gln Arg Leu Leu Pro Val Leu Cys Gln Thr His Gly
20 25 30

<210> SEQ ID NO 212
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 212

Leu Thr Pro Asn Gln Leu Val Ala Ile Ala Asn Gly Gly Lys Gln Ala
1 5 10 15

Leu Glu Thr Val Gln Arg Leu Leu Pro Val Leu Cys Gln Asp His Gly
20 25 30

<210> SEQ ID NO 213
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 213

Leu Ser Pro Ala Gln Val Val Ala Ile Ala Ser Gly Ser Lys Gln Ala
1 5 10 15

Leu Glu Thr Val Gln Arg Leu Leu Pro Val Leu Cys Gln Asp His Gly
20 25 30

<210> SEQ ID NO 214
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 214

Leu Thr Pro Asp Gln Val Val Ala Ile Ala Ser Gly Gly Lys Gln Ala
1 5 10 15

Leu Glu Thr Val Gln Arg Val Leu Pro Val Leu Cys Gln Ala His Gly
20 25 30

<210> SEQ ID NO 215
<211> LENGTH: 32
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 215

Leu Thr Pro Asp Gln Val Met Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 216
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Leu Thr Pro Glu Gln Val Val Ala Ile Ala Ser Gly Gly Arg Gln Ala
1               5                   10                  15

Leu Glu Thr Val Gln Arg Leu Leu Pro Val Leu Cys Gln Ala His Gly
            20                  25                  30

<210> SEQ ID NO 217
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Leu Thr Pro Ala Gln Val Val Ala Ile Ala Ser Gly Gly Lys Gln Ala
1               5                   10                  15

Leu Glu Thr Val Gln Trp Leu Leu Pro Val Leu Cys Gln Ala His Gly
            20                  25                  30

<210> SEQ ID NO 218
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Leu Thr Pro Asp Lys Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 219
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Leu Thr Pro Ala Gln Val Met Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 220
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 220

Leu Thr Gln Asp Gln Val Val Ala Ile Ala Ser Gly Gly Lys Gln Ala
1 5 10 15

Leu Glu Thr Val Gln Arg Leu Leu Pro Val Leu Cys Gln Ala Asn Gly
20 25 30

<210> SEQ ID NO 221
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 221

Leu Thr Pro Ala Gln Val Val Ala Ile Ala Ser Gly Gly Lys Pro Ala
1 5 10 15

Leu Glu Thr Val Gln Arg Leu Leu Pro Val Leu Cys Glu Gln His Gly
20 25 30

<210> SEQ ID NO 222
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 222

Leu Thr Pro Asp Gln Val Val Ala Ile Ala Ser Ser Gly Lys Gln Ala
1 5 10 15

Leu Glu Thr Met Gln Arg Leu Leu Pro Val Leu Cys Gln Asp His Gly
20 25 30

<210> SEQ ID NO 223
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 223

Leu Thr Pro Asp Gln Val Val Ala Ile Ala Ser Gly Ser Lys Gln Ala
1 5 10 15

Leu Glu Thr Val Gln Arg Leu Leu Pro Val Leu Arg Gln Asp His Gly
20 25 30

<210> SEQ ID NO 224
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 224

-continued

```
Leu Thr Pro Tyr Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
            20                  25                  30


<210> SEQ ID NO 225
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Leu Thr Pro Tyr Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30


<210> SEQ ID NO 226
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Gln Glu His Gly
            20                  25                  30


<210> SEQ ID NO 227
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Leu Thr Leu Glu Gln Val Val Ala Ile Ala Ser Gly Gly Lys Gln Ala
1               5                   10                  15

Leu Glu Thr Val Gln Arg Leu Leu Leu Val Leu Cys Gln Ala His Gly
            20                  25                  30


<210> SEQ ID NO 228
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Leu Thr Pro Asp Gln Val Val Ala Ile Ala Ser Gly Gly Lys Gln Ala
1               5                   10                  15

Leu Glu Thr Val Arg Arg Leu Leu Gln Val Leu Cys Gln Asp His Gly
            20                  25                  30


<210> SEQ ID NO 229
<211> LENGTH: 32
<212> TYPE: PRT
<213> ORGANISM: Artificial Sequence
```

<220> FEATURE:
<223> OTHER INFORMATION: Description of Artificial Sequence: Synthetic
polypeptide

<400> SEQUENCE: 229

Leu Thr Pro Asp Gln Val Val Ala Ile Ala Ser Gly Gly Lys Gln Ala
1 5 10 15

Leu Glu Thr Val Gln Arg Leu Leu Pro Val Leu Arg Gln Asp His Gly
20 25 30

<210> SEQ ID NO 230
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 230

Leu Thr Pro Asp Gln Val Val Ser Ile Ala Asn Gly Gly Lys Gln Ala
1 5 10 15

Leu Glu Thr Val Gln Arg Leu Leu Pro Val Leu Cys Gln Ala His Gly
20 25 30

<210> SEQ ID NO 231
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 231

Leu Thr Pro Asp Gln Val Val Ala Ile Ala Asn Gly Gly Lys Gln Ala
1 5 10 15

Leu Glu Thr Val Gln Arg Leu Leu Pro Val Leu Cys Gln Thr His Gly
20 25 30

<210> SEQ ID NO 232
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 232

Leu Thr Pro Asp Gln Val Val Ala Ile Ala Ser Gly Gly Lys Gln Ala
1 5 10 15

Leu Glu Thr Val Lys Arg Leu Leu Pro Val Leu Cys Gln Ala His Gly
20 25 30

<210> SEQ ID NO 233
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 233

Leu Thr Thr Asp Gln Val Val Ala Ile Ala Asn Gly Gly Lys Gln Ala
1 5 10 15

Leu Glu Thr Val Gln Arg Leu Leu Pro Val Leu Cys Gln Asp His Gly
20 25 30

<210> SEQ ID NO 234
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 234

```
Leu Ile Pro Gln Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 235
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 235

```
Leu Thr Leu Thr Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30
```

<210> SEQ ID NO 236
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 236

```
Leu Thr Pro Thr Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 237
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 237

```
Leu Thr Pro Thr Gln Val Met Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30
```

<210> SEQ ID NO 238
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 238

```
Leu Thr Pro Asp Gln Val Val Ala Val Ala Ser Gly Gly Lys Gln Ala
1               5                   10                  15

Leu Glu Thr Val Gln Arg Leu Leu Pro Val Leu Cys Gln Ala His Gly
            20                  25                  30


<210> SEQ ID NO 239
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Leu Thr Pro Ala Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
            20                  25                  30


<210> SEQ ID NO 240
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Leu Thr Pro Gly Gln Val Val Ala Ile Ala Ser Gly Gly Lys Arg Ala
1               5                   10                  15

Leu Glu Thr Val Gln Arg Leu Leu Pro Val Leu Cys Gln Asp His Gly
            20                  25                  30


<210> SEQ ID NO 241
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Leu Thr Pro Asp Gln Val Val Val Ile Ala Ser Gly Gly Lys Gln Ala
1               5                   10                  15

Leu Glu Thr Val Gln Arg Leu Leu Pro Val Leu Cys Gln Ala His Gly
            20                  25                  30


<210> SEQ ID NO 242
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Leu Pro Pro Asp Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
            20                  25                  30


<210> SEQ ID NO 243
<211> LENGTH: 32
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 243

Leu Thr Pro Asp Gln Val Val Thr Ile Ala Asn Gly Ser Lys Gln Ala
1 5 10 15

Leu Glu Thr Val Gln Arg Leu Leu Pro Val Leu Cys Gln Ala His Gly
20 25 30

<210> SEQ ID NO 244
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 244

Leu Thr Pro Ala Gln Val Val Ala Ile Ala Ser Gly Gly Lys Gln Ala
1 5 10 15

Leu Glu Thr Val Gln Arg Leu Leu Gln Val Leu Cys Gln Asp His Gly
20 25 30

<210> SEQ ID NO 245
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 245

Leu Thr Pro Asp His Val Val Ala Ile Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 246
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 246

Leu Thr Pro Asp Gln Val Val Ala Ile Ala Ser Gly Gly Lys Gln Ala
1 5 10 15

Leu Glu Thr Val Gln Arg Leu Leu Gln Val Leu Cys Gln Asp His Gly
20 25 30

<210> SEQ ID NO 247
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 247

Leu Thr Pro Asp Gln Val Val Ala Ile Ala Ser Gly Gly Arg Gln Ala
1 5 10 15

Leu Glu Thr Val Gln Arg Leu Leu Pro Val Leu Cys Glu Gln His Gly 20 25 30

<210> SEQ ID NO 248
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 248

Leu His Pro Gly Gln Val Val Ala Ile Ala Ser Gly Gly Lys Gln Ala
1 5 10 15

Leu Glu Thr Val Gln Arg Leu Leu Pro Val Leu Cys Gln Ala His Gly
20 25 30

<210> SEQ ID NO 249
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 249

Leu Thr Leu Asp Gln Val Val Ser Ile Ala Ser Gly Gly Lys Gln Ala
1 5 10 15

Leu Glu Thr Val Gln Arg Leu Leu Pro Val Leu Cys Gln Asp His Gly
20 25 30

<210> SEQ ID NO 250
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 250

Leu Thr Pro Asp Gln Val Val Ala Ile Ala Ser Gly Gly Lys Gln Ala
1 5 10 15

Leu Glu Thr Val Gln Arg Leu Leu Pro Ala Leu Cys Gln Asp His Gly
20 25 30

<210> SEQ ID NO 251
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 251

Leu Thr Pro Asp Gln Val Val Ala Ile Ala Ser Gly Gly Lys Pro Ala
1 5 10 15

Leu Glu Thr Val Gln Arg Leu Leu Pro Val Leu Cys Glu Gln His Gly
20 25 30

<210> SEQ ID NO 252
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 252

Leu Thr Pro Ala Gln Val Val Ala Ile Ala Ser Gly Gly Lys Gln Ala
1               5                   10                  15

Leu Lys Thr Val Gln Arg Leu Leu Pro Val Leu Cys Gln Ala His Gly
            20                  25                  30

<210> SEQ ID NO 253
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 253

Leu Thr Pro Asp Gln Val Val Ala Ile Ala Ser Gly Gly Lys Arg Ala
1               5                   10                  15

Leu Glu Thr Val Gln Arg Leu Leu Pro Val Leu Cys Gln Ala His Gly
            20                  25                  30

<210> SEQ ID NO 254
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 254

Leu Asn Pro Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 255
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 255

Leu Thr Pro Asp Gln Val Val Ala Ile Ala Ser Gly Gly Lys Gln Ala
1               5                   10                  15

Leu Glu Thr Val Lys Arg Leu Leu Pro Val Leu Cys Gln Asp His Gly
            20                  25                  30

<210> SEQ ID NO 256
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 256

Leu Thr Leu Asp Gln Val Val Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 257
<211> LENGTH: 32

-continued

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 257

Leu Thr Pro Ala Gln Val Val Ala Ile Ala Ser Gly Gly Lys Gln Ala
1 5 10 15

Leu Glu Thr Val Gln Arg Leu Leu Pro Val Leu Cys Arg Asp His Gly
20 25 30

<210> SEQ ID NO 258
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 258

Leu Thr Pro Ala Gln Val Leu Ala Ile Ala Ser Gly Gly Lys Gln Ala
1 5 10 15

Leu Glu Thr Val Gln Arg Leu Leu Thr Val Leu Cys Gln Asp His Gly
20 25 30

<210> SEQ ID NO 259
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 259

Leu Thr Pro Ala Gln Val Val Ala Ile Ala Ser Gly Gly Lys Gln Ala
1 5 10 15

Leu Glu Thr Met Gln Arg Leu Leu Pro Val Leu Cys Gln Asp His Gly
20 25 30

<210> SEQ ID NO 260
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 260

Leu Thr Pro Asp Gln Val Val Ala Ile Ala Ser Gly Gly Lys Gln Ala
1 5 10 15

Leu Glu Thr Val Gln Arg Leu Leu Pro Gly Leu Cys Gln Ala His Gly
20 25 30

<210> SEQ ID NO 261
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 261

Leu Thr Arg Glu Gln Val Val Ala Ile Ala Ser Gly Gly Lys Gln Ala
1 5 10 15

```
Leu Glu Thr Val Gln Ala Leu Leu Pro Val Leu Arg Gln Ala His Gly
            20                  25                  30


<210> SEQ ID NO 262
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Gln Val His Gly
            20                  25                  30


<210> SEQ ID NO 263
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Leu Thr Pro Asn Gln Val Val Ala Ile Ala Ser Gly Gly Lys Gln Ala
1               5                   10                  15

Leu Glu Thr Val Gln Arg Leu Leu Leu Val Leu Cys Gln Asp His Gly
            20                  25                  30


<210> SEQ ID NO 264
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Leu Thr Pro Asp Gln Val Met Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30


<210> SEQ ID NO 265
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Leu Thr Arg Glu Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30


<210> SEQ ID NO 266
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 266

Leu Ser Thr Ala Gln Val Val Ala Ile Ala Ser Gly Gly Lys Gln Ala
1               5                   10                  15

Leu Glu Gly Ile Gly Glu Gln Leu Leu Lys Leu Arg Thr Ala Pro Tyr
            20                  25                  30

Gly

<210> SEQ ID NO 267
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Leu Ser Thr Ala Gln Val Val Ala Val Ala Ser Gly Gly Lys Pro Ala
1               5                   10                  15

Leu Glu Ala Val Arg Ala Gln Leu Leu Ala Leu Arg Ala Ala Pro Tyr
            20                  25                  30

Gly

<210> SEQ ID NO 268
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Leu Thr Gln Val Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 269
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Leu Thr Pro Asp Gln Val Val Ala Ile Ala Ser Asn Gly Lys Gln Ala
1               5                   10                  15

Leu Glu Thr Val Gln Arg Leu Leu Pro Val Leu Cys Gln Asp His Gly
            20                  25                  30

<210> SEQ ID NO 270
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Leu Thr Pro Asp Gln Val Val Ala Ile Ala Ser Gly Gly Lys Arg Ala
1               5                   10                  15

Leu Glu Thr Val Gln Arg Leu Leu Pro Val Leu Cys Gln Asp His Gly

-continued

```
            20                    25                    30


<210> SEQ ID NO 271
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271

tttattccct gaca                                                    14


<210> SEQ ID NO 272
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272

tcggcccctg ccggccca                                                18


<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273

tgcctgccct ccaggctcct                                              20
```

COMPOSITIONS AND METHODS OF TREATING HEAD AND NECK CANCER

RELATED APPLICATIONS AND INCORPORATION BY REFERENCE

This application claims priority to U.S. provisional patent application Ser. No. 61/512,279 filed Jul. 27, 2011.

SEQUENCE LISTING

The instant application contains a Sequence Listing which has been submitted in ASCII format via EFS-Web and is hereby incorporated by reference in its entirety. Said ASCII copy, created on Aug. 21, 2012, is named 447999204.txt and is 116,563 bytes in size.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Citation or identification of any document in this application is not an admission that such document is available as prior art to the present invention.

FEDERAL FUNDING LEGEND

This invention was made with government support under R01NS073124 awarded by the National Institutes of Health, and P50CA097190 awarded by the National Institutes of Health. The Government has certain rights in the invention.

FIELD OF THE INVENTION

The present invention generally relates to the treatment of cancer. More specifically the invention relates to the identification of mutations in genes associated with head and neck squamous cell carcinoma (HNSCC) and methods of treatment based on altering function or expression of these genes or altering the function or expression of particular genomic loci associated with these genes. The methods of treatment may also include surgery, radiation or the administration of chemotherapeutic agents, alone or in combination with other agents or compounds.

BACKGROUND OF THE INVENTION

Head and neck squamous cell carcinoma (HNSCC) is the sixth most common non-skin cancer in the world, with an incidence of ~600,000 cases per year and mortality rate of ~50%. The major risk factors for HNSCC are tobacco use, alcohol consumption, and infection with human papilloma virus (HPV). Despite advances in knowledge of its epidemiology and pathogenesis, the survival rates for many types of HNSCC have improved little over the past forty years. The overall 5-year survival rate of HNSCC patients is only about 50%, and this number has not changed in more than three decades.

Tobacco, alcohol consumption and viral agents are the major risk factors for development of HNSCC. These risk factors, together with genetic susceptibility, result in the accumulation of multiple genetic and epigenetic alterations in a multistep process of cancer development (Kim and Califano, *Int J Cancer* 112:545-53, 2004). However, the underlying cellular and molecular mechanisms that contribute to the initiation and progression from normal epithelia to invasive squamous cell carcinoma have not been clearly delineated (Mao et al., *Cancer Cell* 5:311-6, 2004). A better understanding of molecular carcinogenesis of HNSCC would be valuable in its early detection, prognostication and development of new strategies for prevention and treatment.

As such, a deeper understanding of HNSCC pathogenesis is needed to promote the development of improved therapeutic approaches. There is still a need for methods of treating HNSCC more effectively.

SUMMARY OF THE INVENTION

The invention particularly relates to the identification of mutations in genes associated with HNSCC and methods of treatment based on the diagnostic information provided by these mutations. More specifically the invention relates to methods of treatment which may alleviate a symptom of HNSCC, or its related premalignant lesions. Aspects of the invention relate to the diagnostic information about these mutations in HNSCC-associated genes being used as a guide to choose therapy such as surgery, radiation or administration of a chemotherapeutic agent.

Methods of the invention may include administering to a subject in need thereof, a non-naturally occurring or engineered composition or compound that may have a compound that may decrease the function of an HNSCC-associated gene with aberrant gain-of-function; or a compound that may increase the function of an HNSCC-associated gene with aberrant loss-of-function. Even more specifically, the engineered composition or compound may include a chemotherapeutic agent being administered along with immunomodulatory agents or symptom relieving agents. More specifically the invention may also relate to methods of altering expression of genomic locus of interest associated with a HNSCC-associated gene by administering a non-naturally occurring or engineered composition that may comprise transcriptional activator like effector (TALE) polypeptides that may have one or more effector domains and that specifically target genes that have gain-of-function or loss-of-function in head and neck cancer and its associated pre-malignant lesions.

The invention features methods of treating or alleviating a symptom of HNSCC, or its related premalignant lesions, by administering to a subject in need thereof a non-naturally occurring or engineered composition or compound that may comprise a compound that may decrease or alter the function of an HNSCC-associated gene in such a way to counteract an aberrant gain-of-function in that or associated genes; or a compound that may increase or alter the function of an HNSCC-associated gene in such a way to counteract an aberrant loss-of-function in that or associated genes.

The HNSCC-associated gene may be selected from FIG. 22A-B. With regards to HNSCC-associated genes, mention is made of Stransky et al., "The Mutational Landscape of Head and Neck Squamous Cell Carcinoma", *Science*, Vol 333, 26 Aug. 2011, the contents of which are incorporated by reference herein in their entirety. HNSCC-associated genes may include but are not limited to TP63, CCND1, CCNE1, MYC, YAP1, HRAS, PIK3CA, PIK3CG, NOTCH1, NOTCH 2, NOTCH 3, IRF6, CDKN2A, TP53, CASP8, PTEN, FAT1, RIPK4, EZH1, EZH2, MED1, MLL2, CDH1, FBXW7, PCLO, RIMS2, RB1, NSD1, EP300 and NFE2L2. Exemplary aberrant gain-of-function HNSCC genes may include TP63, CCND1, CCNE1, MYC, YAP1, HRAS, PIK3CA, PIK3CG or NFE2L2. Exemplary aberrant loss-of-function HNSCC genes may include NOTCH1, NOTCH 2, NOTCH 3, IRF6, CDKN2A, TP53, CASP8, PTEN, FAT1, RIPK4, EZH1, EZH2, MED1, MLL2, CDH1, FBXW7, PCLO, RIMS2, RB1, NSD1 or EP300.

The premalignant lesions of HNSCC may include for example, dysplasia, hyperplasia, leukoplakia, erythroplakia, or hairy tongue.

The invention also relates to methods of altering gene expression of a genomic locus of interest in a mammalian cell, wherein the method may comprise contacting the genomic locus with a non-naturally occurring or engineered composition or compound. The genomic locus of interest may be the locus of any HNSCC-associated gene. Preferably, the non-naturally occurring or engineered composition or compound may include a deoxyribonucleic acid (DNA) binding polypeptide which may comprise at least five or more TALE monomers and at least one or more half-monomers. The polypeptide may further comprise an effector domain. For example the composition or compound may include a TALE transcription factor which may have at least one or more activator or repressor domains or a TALE nuclease which may have at least one or more nuclease domains. With regards to TALE polypeptides, their uses and mode of targeting, mention is made of U.S. application Ser. No. 13/554,922, the contents of which is incorporated herein in its entirety. Further mention is also made of Cong et al., "Comprehensive interrogation of natural TALE DNA-binding modules and transcriptional repressor domains", *Nature Communications* Volume: 3, Article number: 968, the contents of which is also incorporated herein in its entirety.

The invention also relates to methods of inhibiting cell growth of a head and neck squamous cell carcinoma or its related premalignant lesions, wherein the method may comprise administering a therapeutically effective amount of the non-naturally occurring or engineered composition or compound.

Optionally, the method may further include administering a chemotherapeutic agent. In a further preferred embodiment the method may also further comprise the administration of an immunomodulatory agent or a symptom relieving agent.

The non-naturally occurring or engineered composition or compound of the invention may be administered into or near the tumor. Alternatively, the composition or compound may be administered systemically. Aspects of the invention may also include methods of identifying an agent for inhibiting cell growth of HNSCC or its related premalignant lesions, comprising administering the agent to a cell culture expressing a HNSCC-associated gene selected from FIG. 22A-B and determining if the agent decreases the function of the HNSCC-associated gene with aberrant gain-of-function or increases the function of the HNSCC-associated gene with aberrant loss-of-function.

In preferred embodiments of the invention, the genes with aberrant gain-of-function may be TP63, CCND1, CCNE1, MYC, YAP1, HRAS, PIK3CA, PIK3CG or NFE2L2.

In preferred embodiments of the invention, the genes with aberrant loss-of-function may be NOTCH1, NOTCH 2, NOTCH 3, IRF6, CDKN2A, TP53, CASP8, PTEN, FAT1, RIPK4, EZH1, EZH2, MED1, MLL2, CDH1, FBXW7, PCLO, RIMS2, RB1, NSD1 or EP300.

In other advantageous embodiments, the methods of the invention may also include the administration of an agent, wherein the agent may be an antibody, an antisense compound, a small interfering nucleic acid (e.g., siRNA used in RNA interference), a polynucleotide, a polypeptide, a protein or a small molecule.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 15A-F shows a table listing monomer sequences (excluding the RVDs at positions 12 and 13) and the frequency with which monomers having a particular sequence occur. Figures disclose SEQ ID NOS 37-267, respectively, in order of appearance.

n=3. *** p<0.001, Student's t test.

Figure 20:
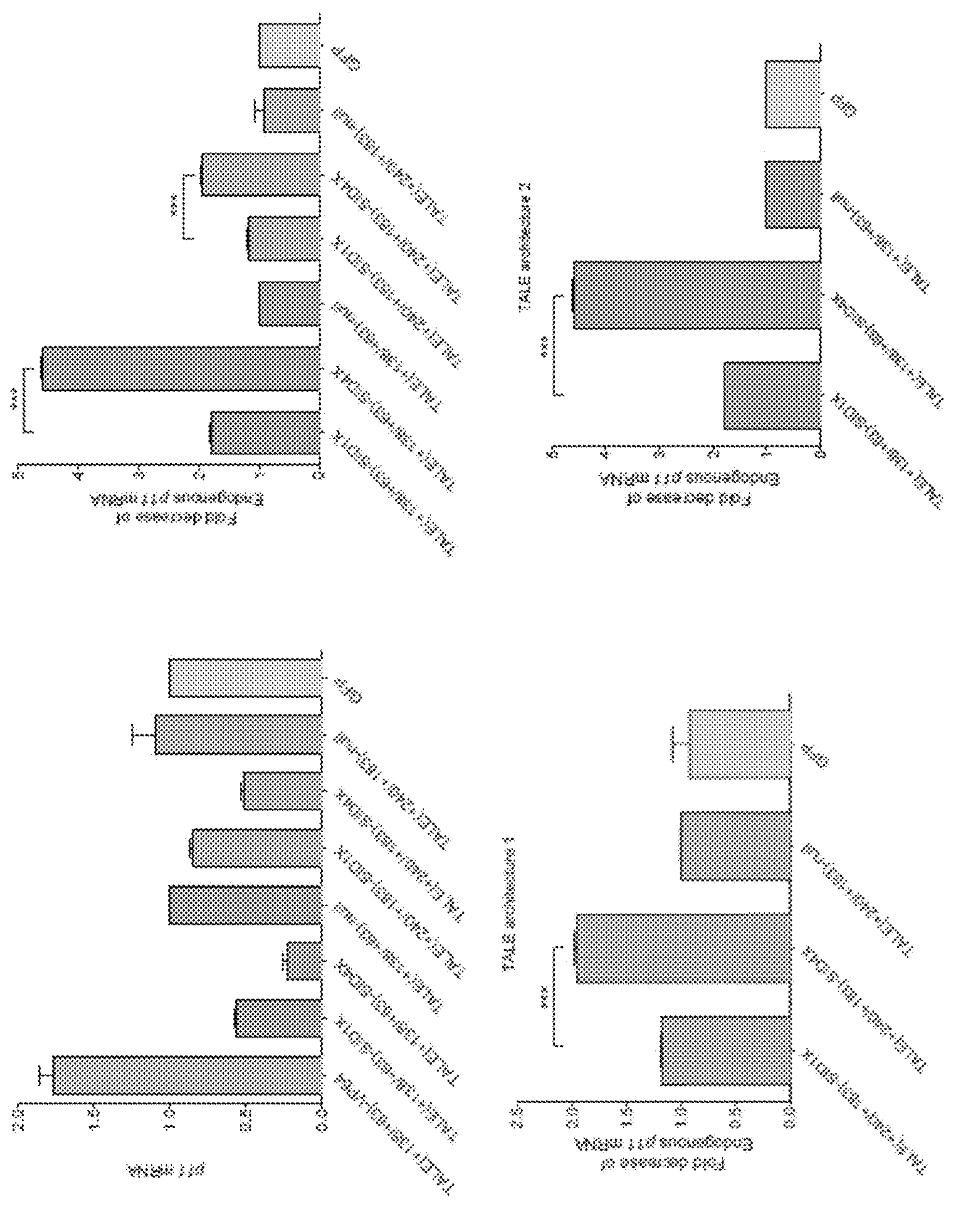

FIG. 20 shows a comparison of two different types of TALE architecture.

FIG. 21 shows Patient and Tumor Characteristics

FIG. 22A-B shows significantly mutated HNSCC genes. The list of genes is ranked by q value and is representative of 74 tumor/normal pairs. N=number of sequenced bases in the gene listed, across samples. n=number of non-synonymous mutations in the gene listed. npat=number of tumors harboring at least one non-synonymous mutation in the gene listed. nsil=number of silent mutations in the gene listed. The genes with higher ratios of synonymous to non-synonymous mutations are more likely to be passengers. All other classes refer to non-synonymous mutations in the categories listed. *CpG→T=C mutated to T (transitions) in CpG dinucleotides. Tp*Cp(A/C/T)→(T/G)=Cs following a T and not followed by a G. *CpG→(G/A)=Cs mutated to G/A (transversions) in CpG dinucleotides. (A/G/T)p*G→T=number of Gs no following a C and mutated to a T. (A/C/G)p*Cp(A/C/T)→(T/G)=Cs not following a T and not followed by a G, mutated to T or G. A→mut=As or Ts mutated. indel+null=nonsense, frameshift, or splice-site mutations. A, C, T, G refer to the nucleotides with A: adenine, C: cytosine, G: guanine, and T: thymine. p=p-value for the observed amount of non-synonymous mutations in the gene listed, given the size of the gene, the number of sequenced bases, and background mutation rates for each of the different mutation categories. Q=q-value for the observed amount of non-synonymous mutations in the gene listed, calculated by the Benjamini-Hochberg procedure. Figure discloses SEQ ID NO: 8.

FIG. 23 shows the functional networks enriched in mutated HNSCC genes.

DETAILED DESCRIPTION OF THE INVENTION

This invention is based, in part, upon the discovery of mutations associated with head and neck squamous cell carcinoma (HNSCC). Specifically, statistically significant mutations were found in 105 genes, and are described in FIG. 22A-B and these genes including the mutations identified are collectively referred to herein as, inter alia, "HNSCC-associated genes". The mutations either result in an aberrant gain-of-function or loss-of-function of these HNSCC-associated genes.

Accordingly, the invention provides methods of treating or alleviating a symptom of HNSCC by administering to a cancer patient a non-naturally occurring or engineered composition or compound that may maintain gene expression levels by restoring gene expression to an HNSCC associated gene with loss-of-function due to mutation in that gene or with loss-of-function as a consequence of mutation in another gene that causes loss-of-function of that HNSCC associated gene, or abrogating the aberrant gain of function of an HNSCC associated gene as a consequence of mutation in that gene or another gene that causes aberrant gain-of-function in the HNSCC associated gene. Abrogating the aberrant gain-of-function of an HNSCC gene is achieved by targeting the gene or another related gene that results in the gain-of-function of an HNSCC gene using a TALE nuclease or a TALE that has a transcriptional repressor activity. Similarly, an HNSCC associated gene with loss-of-function can have function restored using a TALE that has transcriptional activator activity targeted to that HNSCC gene, or a related gene, the alteration in function which results in loss-of-function of that HNSCC gene.

Figure 1:
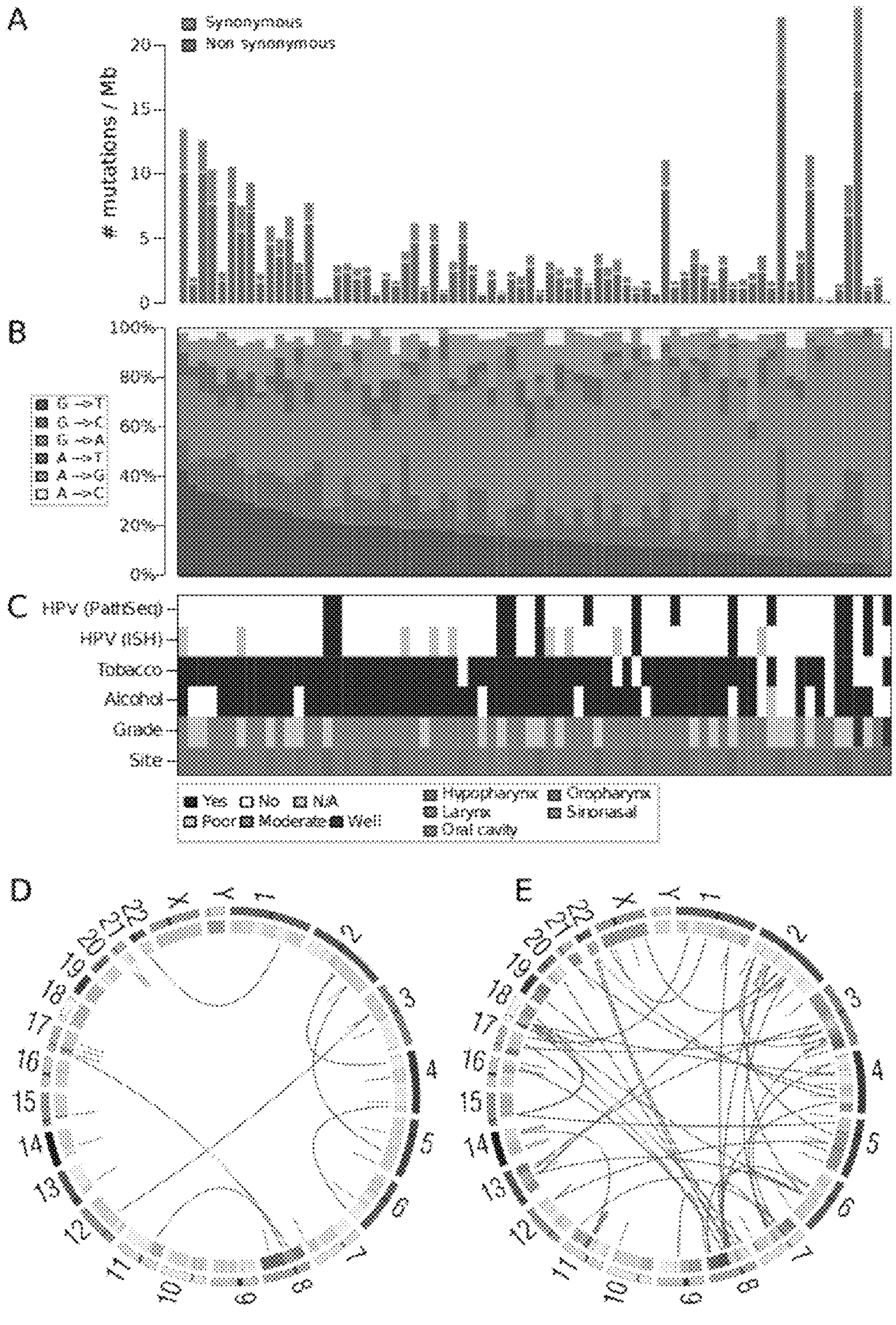
FIG. 1 shows the mutation rates, base substitution frequencies, and rearrangements in head and neck cancers. A. Rate of synonymous and non-synonymous mutations, expressed in mutations per megabase of covered target sequence. Non-synonymous mutation rates range from 0.31 to 16.8 mutations per megabase (mean=3.2). B. Breakdown of individual base substitution rates for the same samples as panel A. The samples were ordered by the rate of G-T transversions, which are indicative of smoking-induced mutations. C. Matrix representation of key clinical parameters for the samples described in panels A and B: cancer zone, histological grading, alcohol and tobacco consumption. The first row indicates tumors where at least one sequencing read unambiguously matching the human papillomavirus genome has been found. D. Circos plots derived from whole genome sequencing of an oropharyngeal tumor (left) and a hypopharyngeal tumor (right). Purple lines represent high confidence interchromosomal rearrangements. Green lines represent high confidence intrachromosomal rearrangements.

Solution-phase hybrid capture and whole exome sequencing on paired DNA samples (tumors and matched whole blood) from 92 HNSCC patients was performed. Most anatomic sites were represented (oral cavity, oropharynx, hypopharynx, larynx, and sinonasal cavity; FIGS. 1C and 21). Of these patients, 89% and 79% reported a history of tobacco and alcohol use, respectively (FIG. 21). Initially, 14% of all tumors and 53% of oropharyngeal tumors were found positive for HPV based on HPV-16 PCR/in situ hybridization (FIG. 1 and FIG. 21). Tumor copy-number analysis using SNP arrays (FIG. 4) replicated previous findings of frequent CCND1 amplifications, CDKN2A deletions, and rarer MYC, EGFR, ERBB2, or CCNE1 amplifications (4), indicating that the collection is genetically representative of HNSCC.

Figure 5:
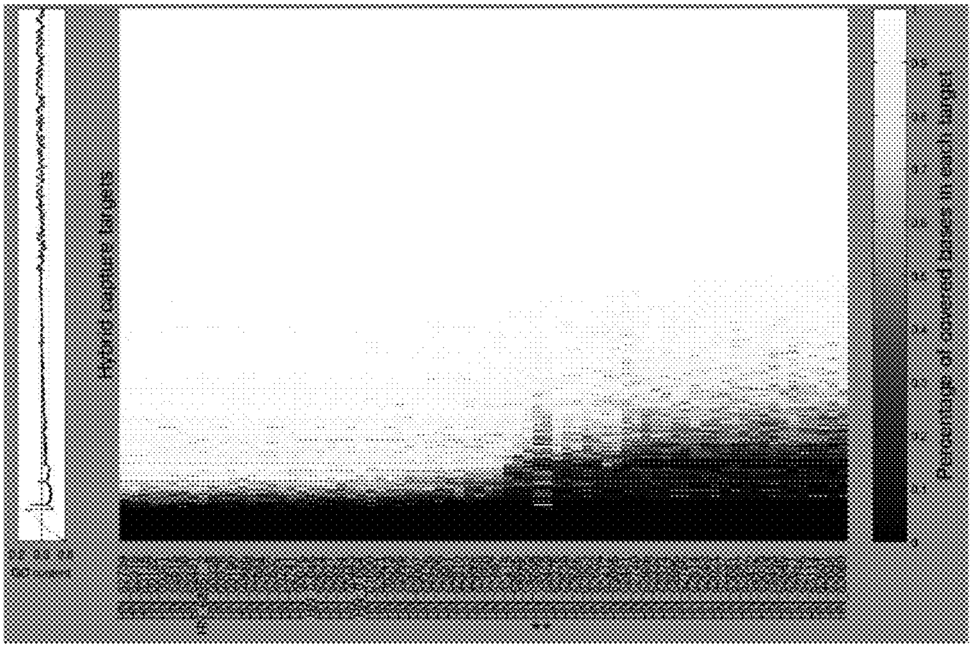
FIG. 5 shows the distribution of target coverage in sequencing data. Left: X-axis shows GC content, calculated as the number of G or C nucleotides/total nucleotides. Each row represents a single hybrid capture target. Middle: each column represents a single sample; each row represents a single hybrid capture target. Right: percentage of covered bases in each hybrid capture target (with at least 14 reads in the tumor and 8 reads in the normal). White indicates 100% of bases in the target with sufficient coverage, black indicates 0% of bases sufficient coverage. Lower levels of coverage were observed at G/C rich genomic loci. Asterisk (*) indicates samples that were also analyzed by whole genome sequencing.
Figure 6:
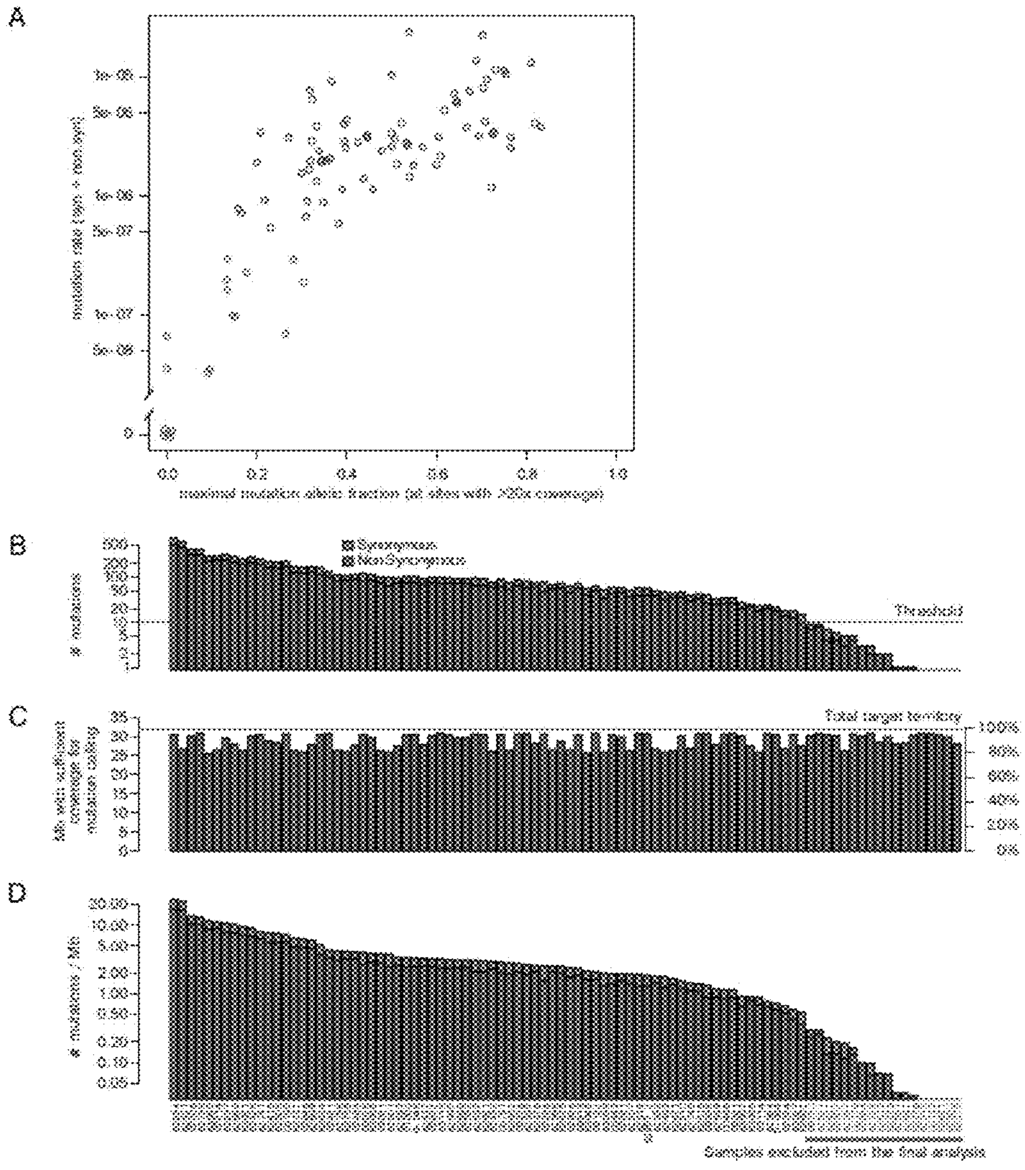
FIG. 6 shows the distribution of maximal allelic fraction and mutation rates in 92 tumor/normal pairs. A. For each sample, the maximal allelic fraction across all mutations at sites with more than 20 reads was calculated and plotted against the mutation rate for the same sample. A positive correlation was observed for these values (r=0.74, p<1e-15, Pearson Correlation). A threshold of 10 mutations per sample (~4e-7 mutations/Mb) was designated as the criteria for exclusion; this corresponds to a an allelic fraction of <20%, and thus a high level of stromal admixture. The 18 samples that fell in that category are shown (red). B. Total number of mutations called per tumor/normal pair. Blue bars represent the number of non-synonymous mutations, green bars represent the number of synonymous mutations. Each bar represents one tumor/normal pair. Tumors with less than 10 mutations (threshold designated as above) were excluded from the final significance analysis. C. Total genomic territory (Mb=megabases) of hybrid capture targets (genes) with adequate coverage for mutation calling. Each bar represents the size of target territory covered for each tumor/normal pair. D. Mutation rate per tumor/normal pair is shown. Excluded tumors/normal pairs are shown (red).

Applicants achieved 150-fold mean sequence coverage of targeted exonic regions, with 87% of loci covered at >20-fold (FIG. 5). Applicants excluded from further analysis 18 tumors in which initial analysis revealed extensive stromal admixture (FIG. 7), leaving 74 samples for analysis. Applicants also performed whole genome sequencing (31-fold mean coverage) on an oropharyngeal tumor and a hypopharyngeal tumor.

On average, 130 coding mutations per tumor were identified, 25% of which were synonymous (FIG. 1A). Applicants queried 321 of these mutations by mass spectrometric genotyping and validated 288 (89.7%). However, the validation rate increased to 95.7% for mutations whose allelic fraction was >20% of total DNA, suggesting that the sensitivity of mass spectrometric genotyping may be reduced in the setting of increased stromal admixture.

Figure 8:
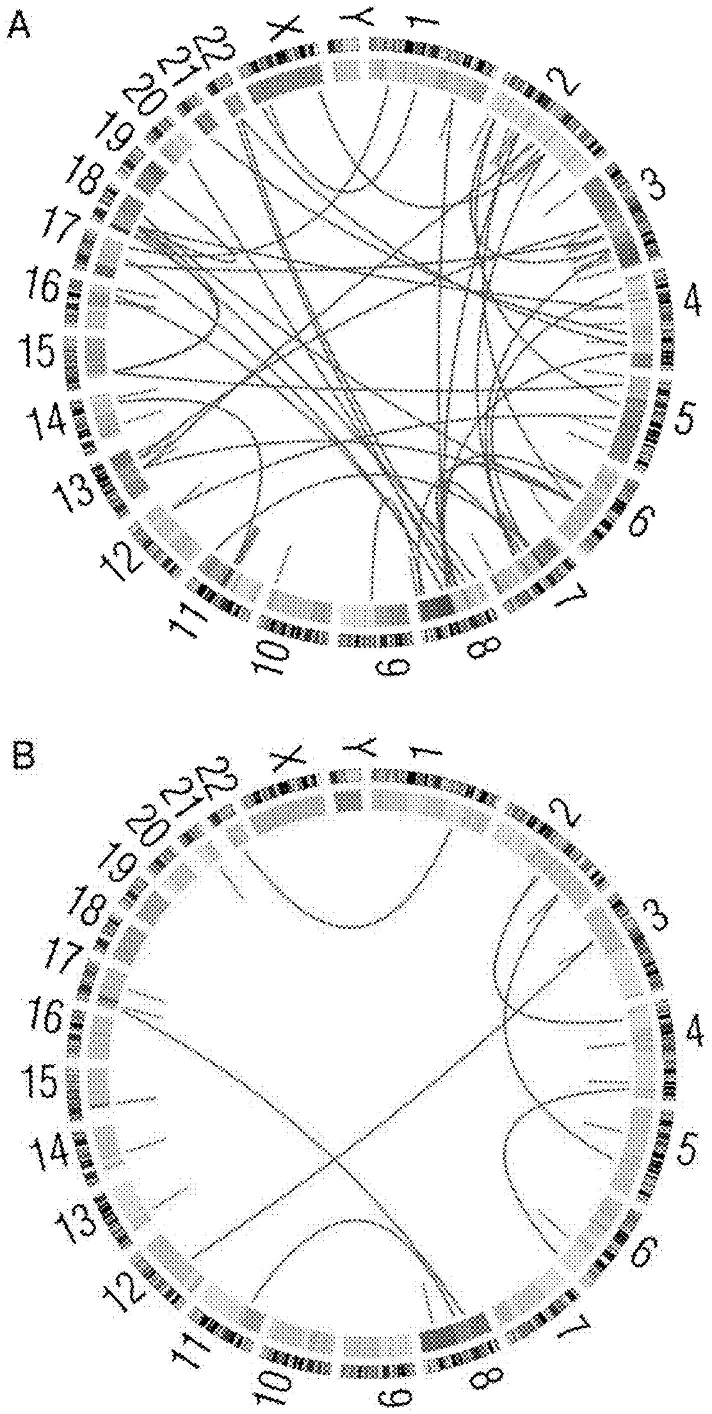
FIG. 8 shows Circos plots derived from whole genome sequencing. An oropharyngeal tumor (62699, A) and a hypopharyngeal tumor (62469, B) are shown. Purple lines represent interchromosomal rearrangements. Green lines represent intrachromosomal rearrangements. Each chromosome is delineated by the appropriate letter or number outside of the plot, as well as the corresponding segments of the concentric circles. The segments of the outer circle represent the normal banding pattern of each chromosome, with blue indicating the centromere. The segments of the inner circle represent copy number changes of each chromosome, inferred from SNP array data. Red indicates copy number gain, blue indicates copy number loss, and the intensity of the color correlates with the magnitude of gain or loss.

The overall HNSCC mutation rate was comparable to other smoking-related malignancies such as small cell lung cancer and lung adenocarcinoma (5, 6). The mutation rate of HPV-positive tumors was approximately half of that found in HPV-negative HNSCC (mean of 2.28 mutations/Mb compared with 4.83 mutations/Mb; p=0.004, rank sum test), consistent with epidemiologic studies suggestive of biological differences between HPV-positive and HPV-negative disease. The two tumors that underwent whole-genome sequencing harbored 19 (HN_62469) and 111 (HN_62699) "high-confidence" somatic rearrangements, respectively (FIG. 8).

Although base mutation rates varied widely (0.59-24 mutations/Mb; FIG. 1A), the average rate of guanosine-to-thymidine (G→T) transversions at non-CpG sites (12%+/−6%) was characteristic of tobacco exposure (FIG. 1B). Among patients who reported a smoking history, tumors with the highest fraction of G→T transversions showed a tendency toward increased overall mutation rates (p=0.02, Spearman rank correlation) (FIG. 1B-C). Thus, the G→T transversion frequency may represent a robust readout of "functional" tobacco exposure. Applicants observed differences in mutation rates and G→T transversion frequencies by tumor site even when restricting the analysis to HPV-negative tumors. In particular, HPV-negative laryngeal cancers exhibited higher mutation rates and G→T transversion frequencies compared to HPV-negative cancers found in the oral cavity, oropharynx, hypoharynx, or sinonasal cavity ($p=0.008$ and $p<0.0001$, respectively, rank sum tests; FIGS. 1A-C and 10).

Notwithstanding the overall apparent correlation between G→T transversions and mutation rates, several "outlier" tumors showed elevated mutation rates despite a low fraction of G→T transversions. Some of these tumors contained mutations in one or more DNA repair genes. Strikingly, both HNSCC tumors with the highest mutation rates occurred in non-smokers (FIG. 1). These results raise the possibility that some HNSCC tumors may contain genetic alterations that promote elevated mutation rates apart from the effects of tobacco (SOM).

Figure 9:
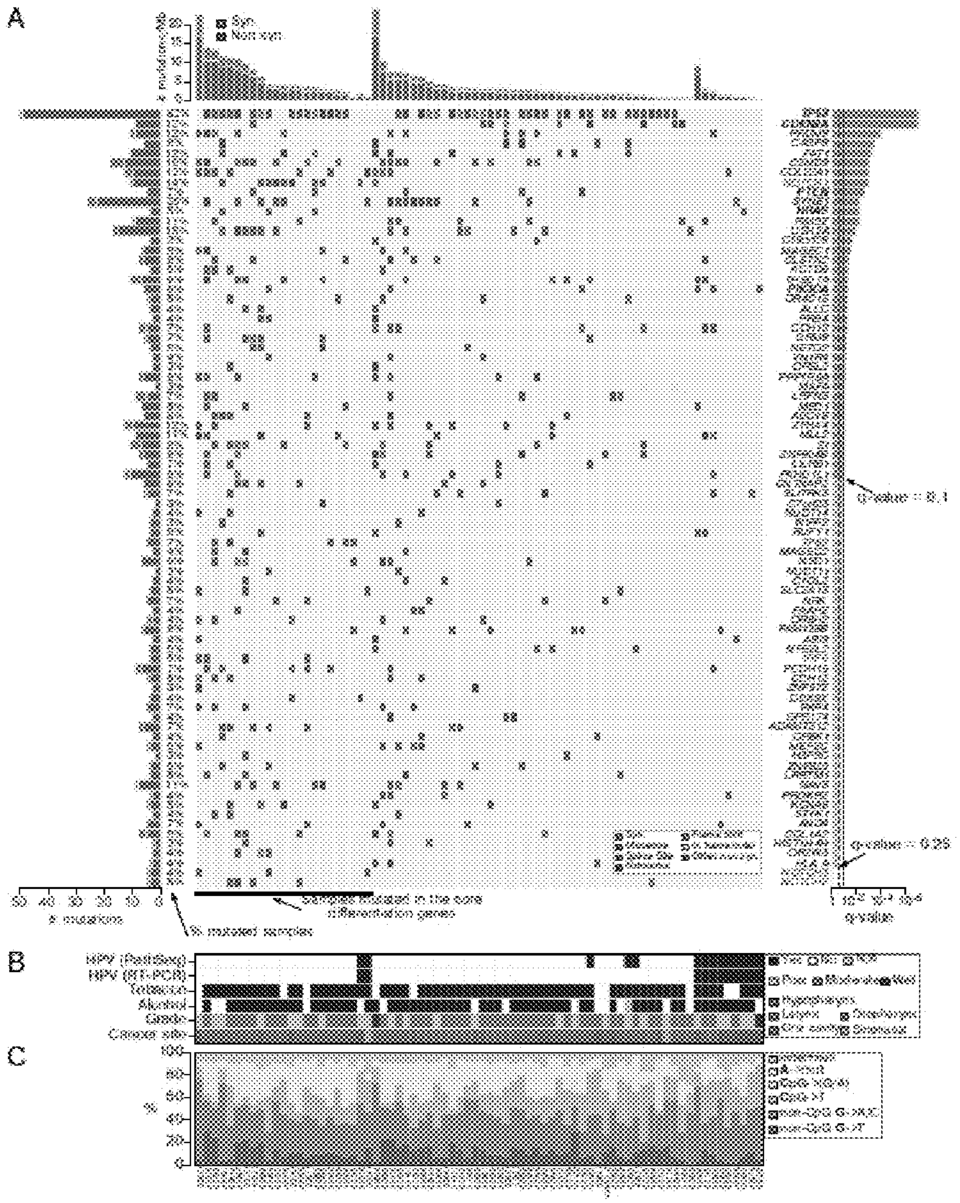
FIG. 9 shows the mutational and clinical characteristics of the final HNSCC data set. A. Distribution of mutations (q<0.25) across samples. In the bar graphs, green represents synonymous mutations, blue represents non-synonymous mutations. The genes with higher ratios of synonymous to non-synonymous mutations are more likely to be passengers. Top: Mutation rate. Each bar represents one tumor/normal pair. Left: Each bar represents total number of mutations in each gene in the final analysis set. Percentages listed represent the percentage of tumor/normal pairs that harbor at least one mutation in the gene listed. Middle: Details of the samples harboring mutations among the most highly significant genes (q<0.1) as well as mutations among slightly less significant genes (q<0.25). Each row represents one gene; each column represents one tumor/normal pair. The color in each cell represents the most disruptive mutation present in that sample. Note that some tumor/normal pairs harbor more than one mutation in a given gene. Right: List of genes sorted by q-value. Genes listed in red represent the genes involved in squamous differentiation with high confidence. The red line represents q=0.1 and denotes the genes with the highest confidence, also marked by a darker shade in the barplot on the right. B. Mutational characteristics of the HNSCC collection. Presence of a squamous differentiation defect is defined as the presence of a mutation in at least one of NOTCH1, NOTCH2, NOTCH3, TP63, or IRF6. HPV status as determined by either sequencing (PathSeq) or real-time PCR(RT-PCR) is also depicted. "Tobacco" represents any history of tobacco use including cigarettes, cigars, or chewing tobacco. "Grade" corresponds to well, moderate, or poorly differentiated histology. "Cancer site" represents anatomic location as defined by American Joint Committee on Cancer (AJCC) criteria. C. Distribution of mutations by nucleotide change.
Figure 10:
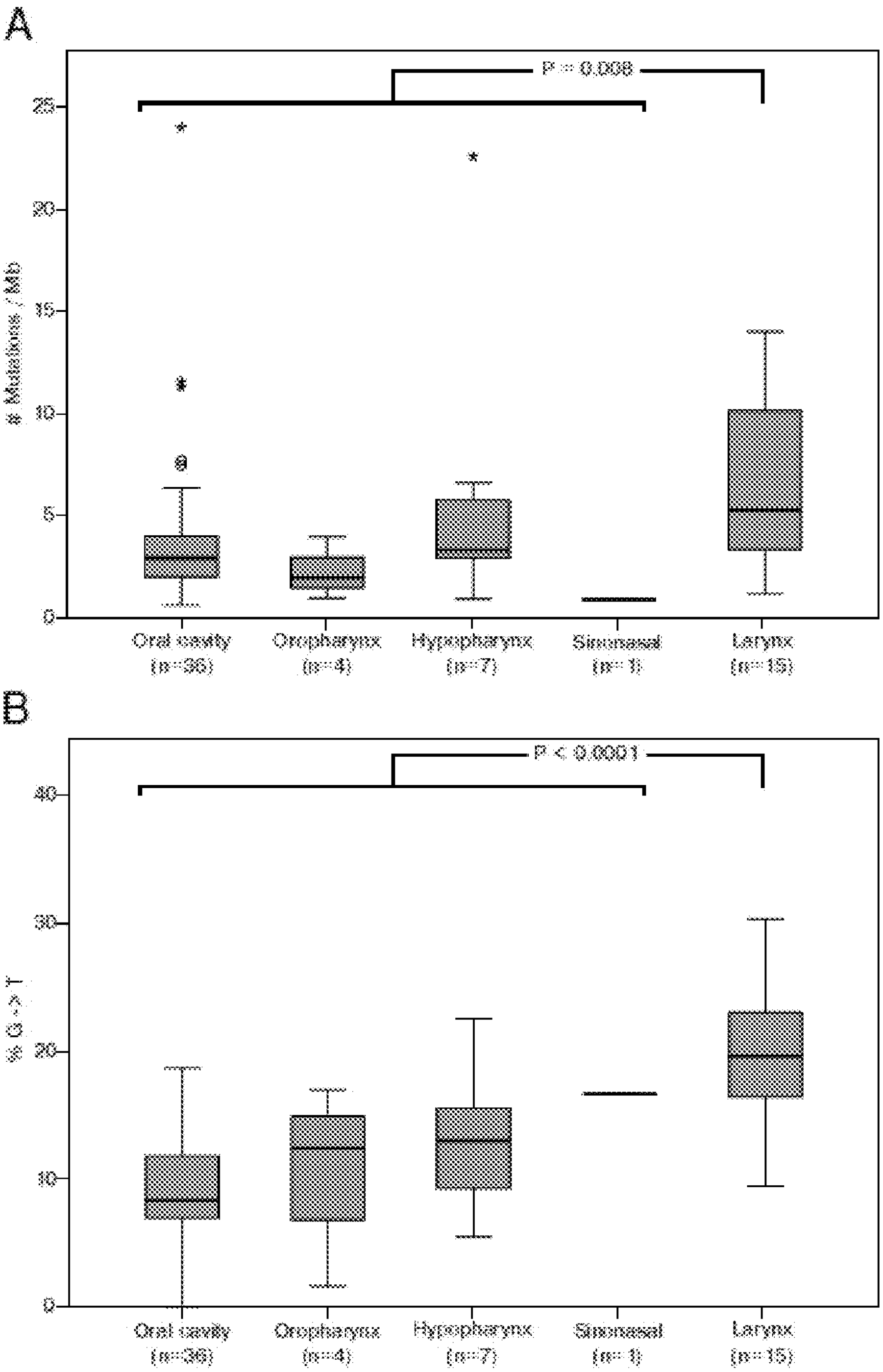
FIG. 10 shows tumor anatomic site and mutation rate. Overall mutation rates and percent of G to T transversions were higher in HPV-negative laryngeal tumors compared to all other sites. A. Among HPV-negative tumors, total mutation rates (synonymous and non-synonymous) were higher in laryngeal tumors compared to other sites (rank sum test P provided). Mutation rates did not differ between HPV-negative tumors from the oral cavity, oropharynx, hypopharynx and sinonasal cavity (p=0.207; Kruskal Wallis test). B. G to T transversions were significantly higher in HPV-negative laryngeal tumors compared to other sites (rank sum test P provided), while G to T transversion rates did not differ among the tumor sites other than the larynx (p=0.536; Kruskal Wallis test). Tumor HPV status was determined using real-time PCR.
Figure 11A:
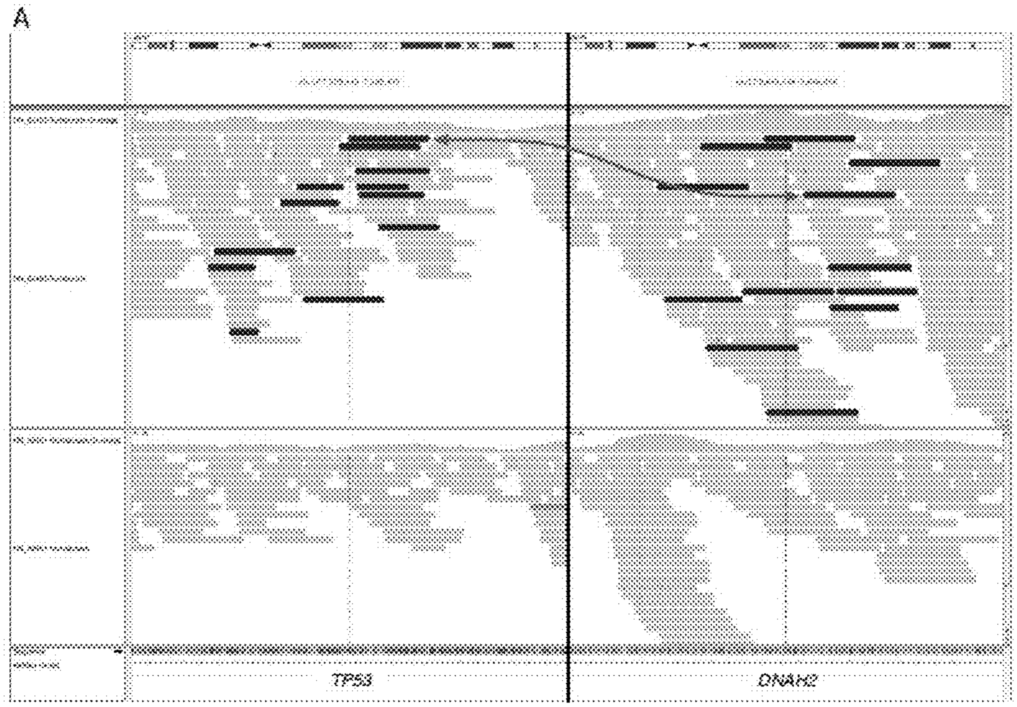
FIG. 11 shows TP53 intra-chromosomal deletion detected by whole genome sequencing. A. IGV screenshots of a rearrangement in TP53. Each horizontal gray bar indicates a single paired-end sequencing read. Maroon reads in the tumor represent paired-end reads that are discordant with the reference genome and therefore designate the rearrangement. The purple arrow denotes two reads belonging to the same pair, as an example. Left: TP53 locus. Right: DNAH2 locus. B. IGV screenshot of copy-number profiles derived from SNP array data. The tumor that harbored a rearrangement detected using dRanger (HN_62469) also shows a DNA copy-number loss spanning the same segment detectable by SNP arrays (purple arrowhead).
Figure 11B:
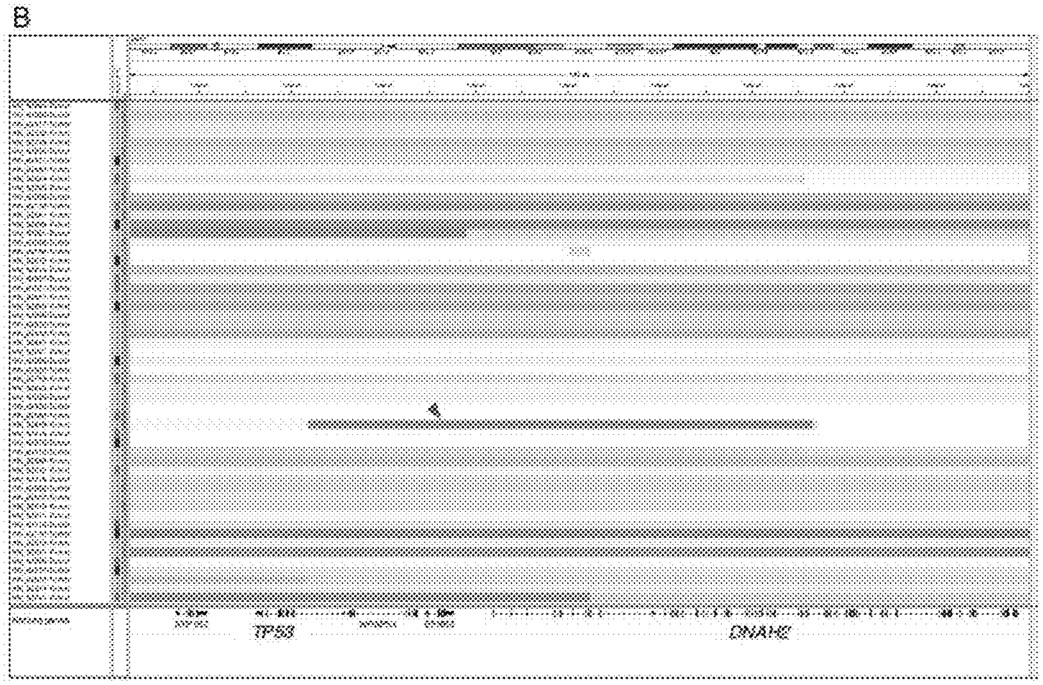

To explore the biological basis of HNSCC in an unbiased manner, Applicants used the MutSig algorithm (7) to identify genes harboring more mutations than expected by chance, given the total number of mutations detected. This analysis revealed 39 genes with high statistical significance (False discovery rate $q<0.1$; FIG. 9). Compared to recent cancer genome projects such as ovarian cancer and multiple myeloma (7, 8), Applicants' analysis of HNSCC revealed a larger number of significantly mutated genes. However, the majority of mutated genes did not reach statistical significance (FIG. 22A-B), suggesting that many may contain passenger events. Thus, Applicants hypothesized that the MutSig algorithm identified an enriched set of genes that likely underwent positive selection during tumorigenesis. Toward this end, numerous significant genes had previously been implicated in HNSCC, including TP53, CDKN2A, HRAS, PTEN, and PIK3CA (4) ($q<0.1$) providing support for the validity of the approach. TP53, the most commonly mutated gene in HNSCC, was also disrupted by a 100 kb deletion detected by whole genome sequencing, and validated with a focal copy number change detected by SNP array (FIG. 11). However, most significantly mutated genes had not previously been implicated in HNSCC.

Figure 2:
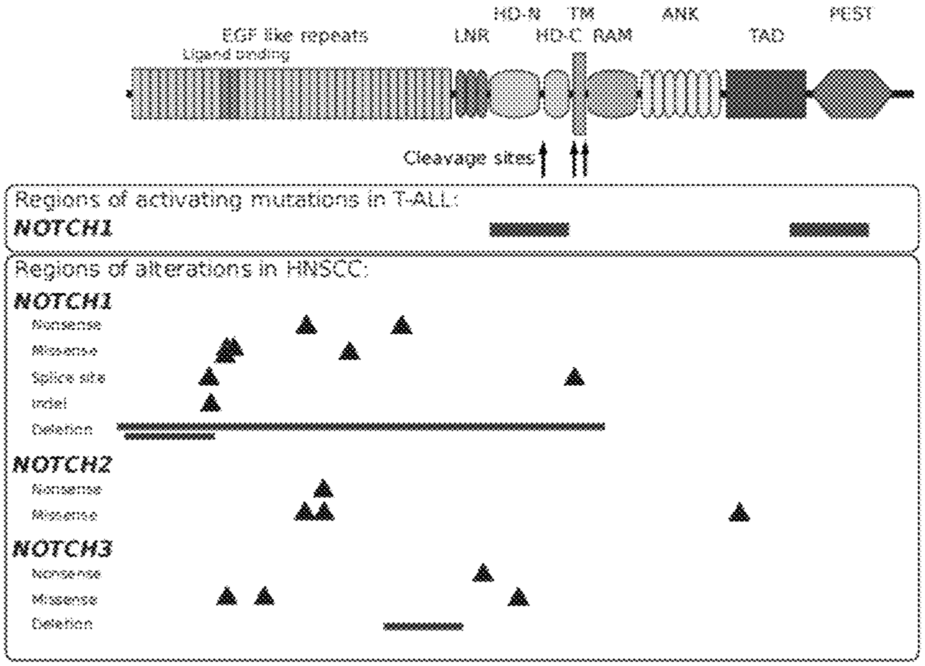
FIG. 2 shows NOTCH gene mutations identified in head and neck cancer. A schematic diagram of the domain structure of NOTCH1 is shown. (The domain structures of NOTCH2 and NOTCH3 are similar.) All nonsense mutations occur upstream of the TAD domain, which is required for transactivation of target genes. Arrows: S1, S2, and S3 proteolytic cleavage sites. Each arrowhead represents a single point mutation in an individual tumor, of the class indicated to the left. LNR: Lin12/Notch repeat. HD-N: N-terminal heterodimerization domain. HD-C: C-terminal heterodimerization domain. TM: Transmembrane domain. RAM: Ram23 domain. ANK: Ankyrin repeats. TAD: Transactivation domain. PEST: Proline, Glutamine, Serine, and Threonine rich domain.
Figure 3:
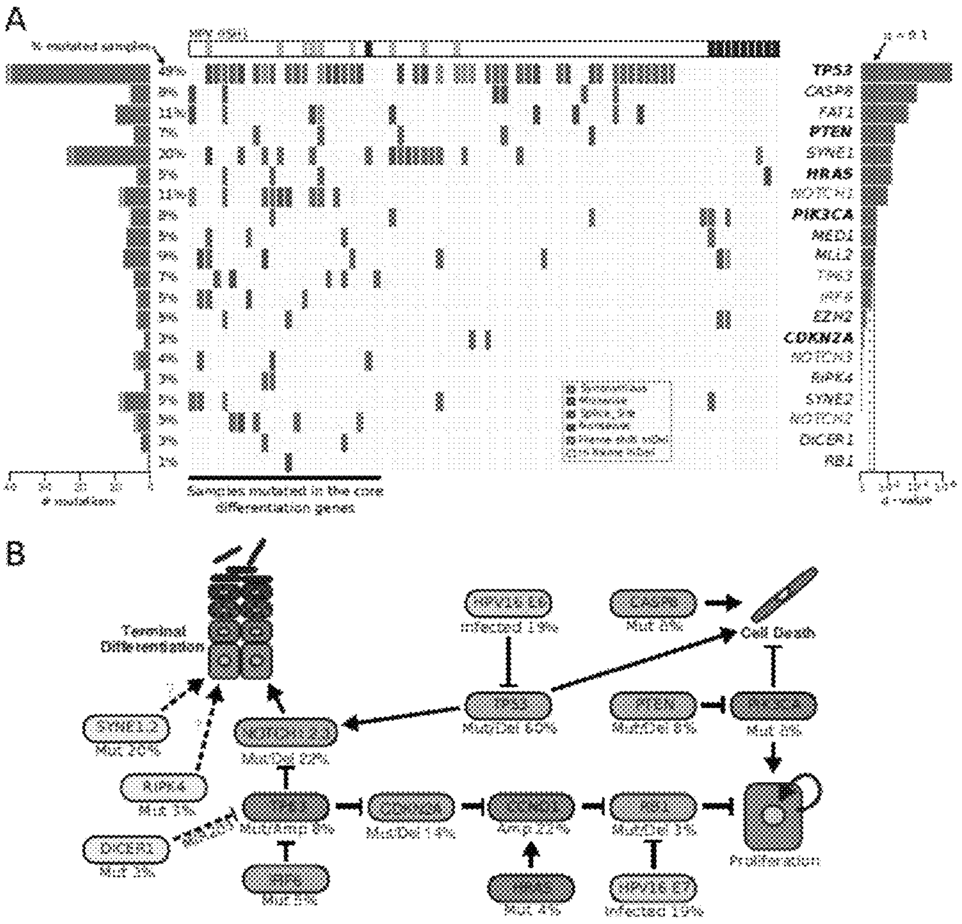
FIG. 3 shows the genetic disruption of a squamous differentiation program in head and neck cancers. A. Heatmap representation of individual mutations present in a series of 74 sequenced and analyzed tumors. Each column in the horizontal axis represents a single tumor. Top: HPV status by tumor Middle: matrix of mutations in individual genes by type of mutation and tumor. Left: number of mutations in each gene in the population of 74 sequenced and analyzed tumors. Percentages represent the fraction of tumors harboring at least one mutation in the specified gene. Right: selected recurrently mutated genes ranked by q-value. Genes that define the core differentiation cluster are listed in red. B. Proposed partial wiring diagram of the molecular circuitry of HNSCC. Blue indicates loss of function, red indicates gain of function. Numbers listed beneath each protein represent the fraction of tumors harboring mutations, amplifications, or deletions in the corresponding genes as indicated in the figure.
Figure 4A:
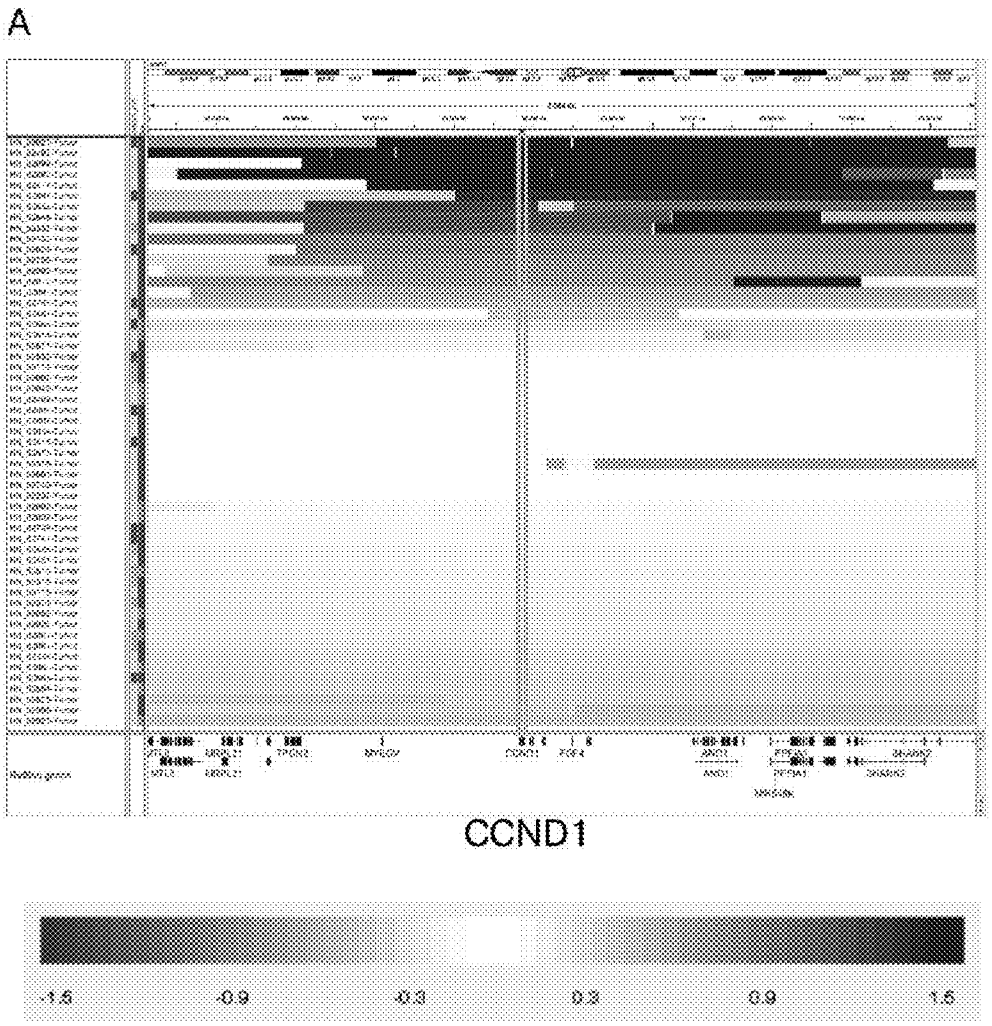
FIG. 4 shows exemplary focal copy number changes detected by SNP arrays. Integrated Genome Viewer (49) outputs are shown. Each row contains a single sample. The horizontal axis shows a linear segment of a single chromosome. Red represents copy gain, blue represents copy loss. Color intensity correlates with increased magnitude of gain or loss. A. CCND1. B. CCNE1. C. EGFR. D. ERBB2. E. MYC. F. YAP1. G. CDKN2A.
Figure 4B:
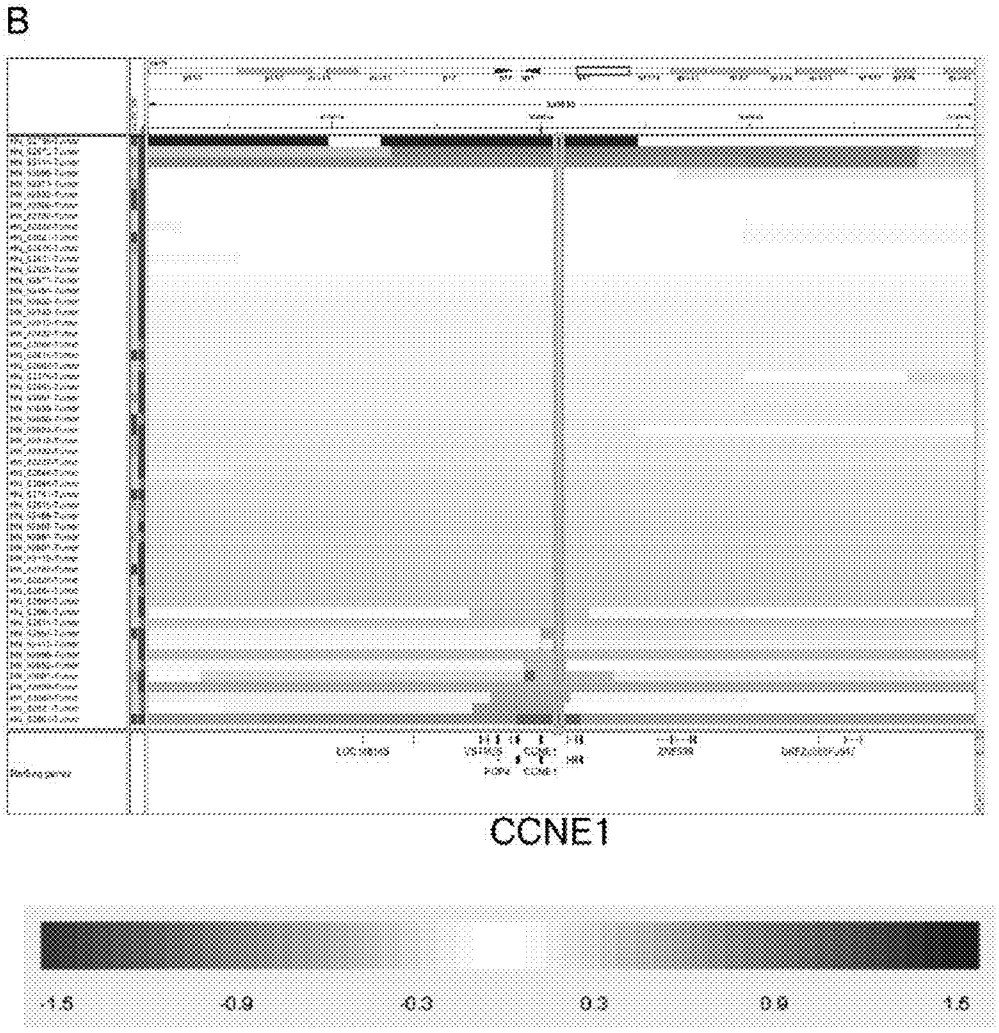
Figure 4C:
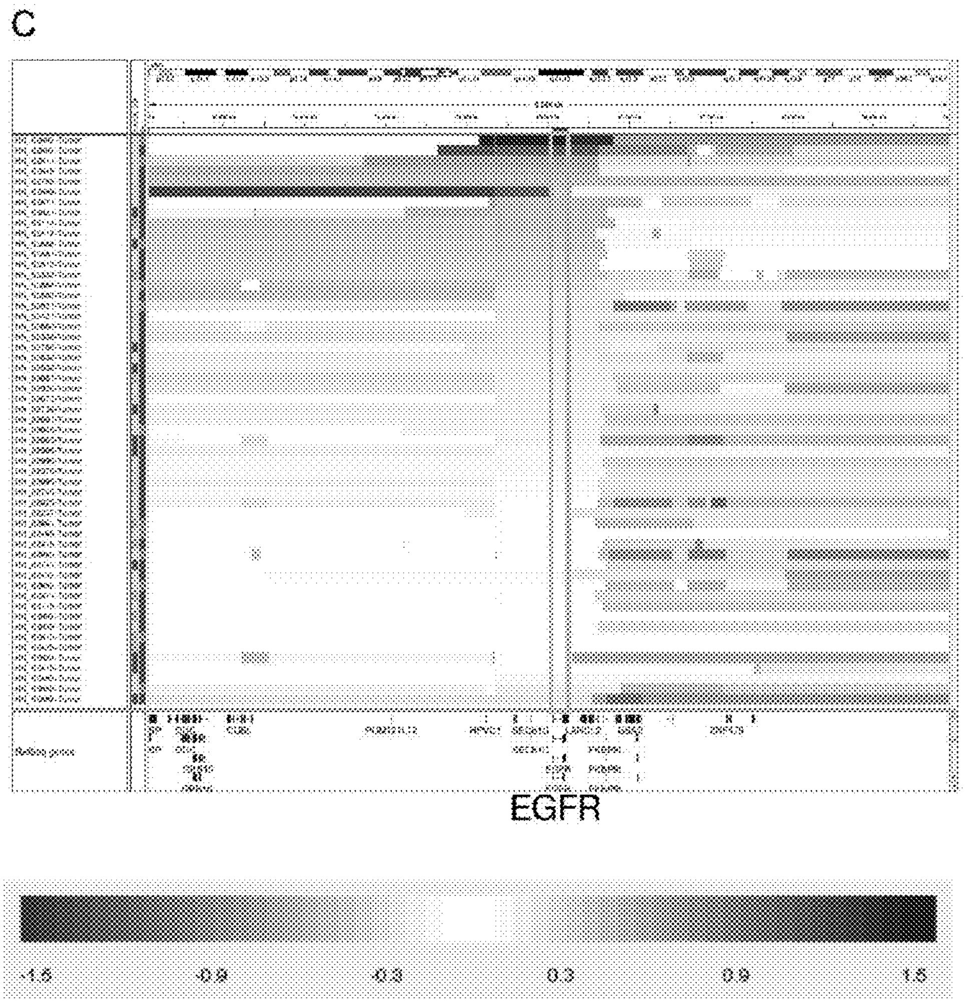
Figure 4D:
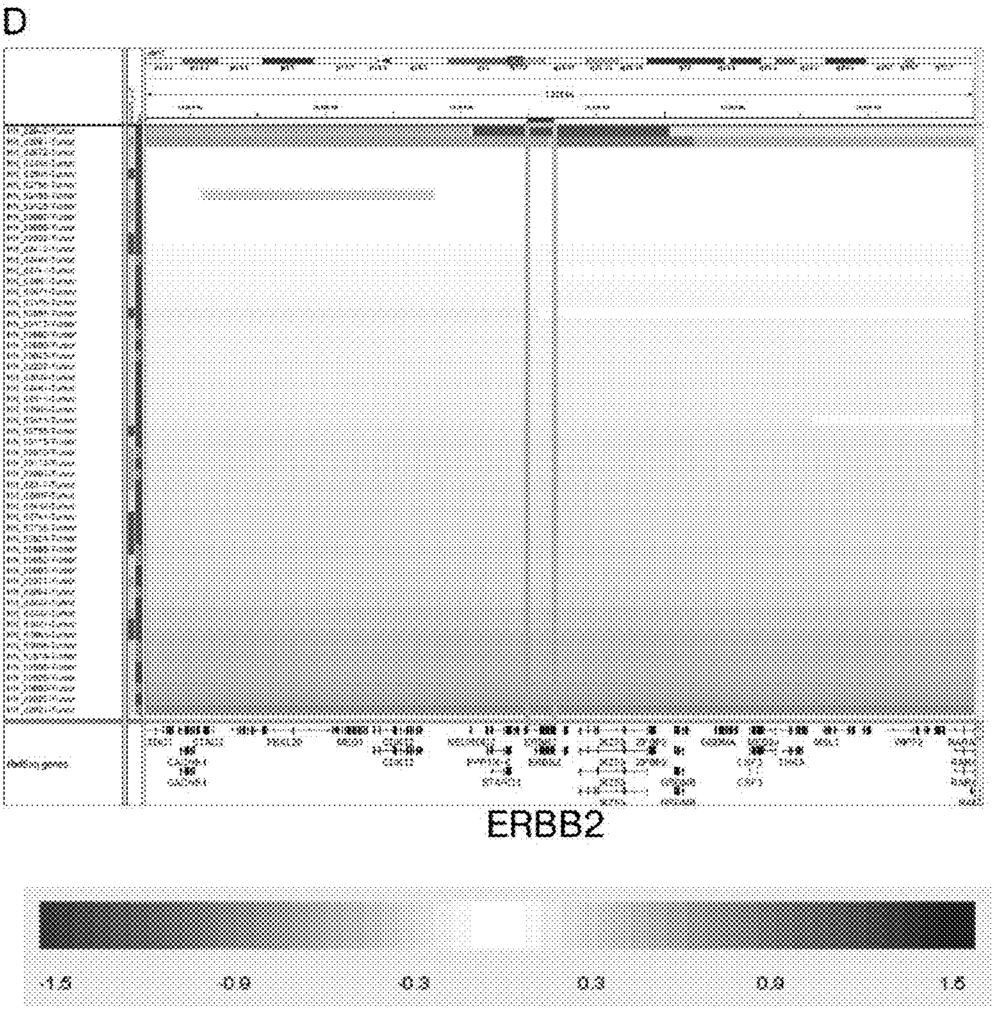
Figure 4E:
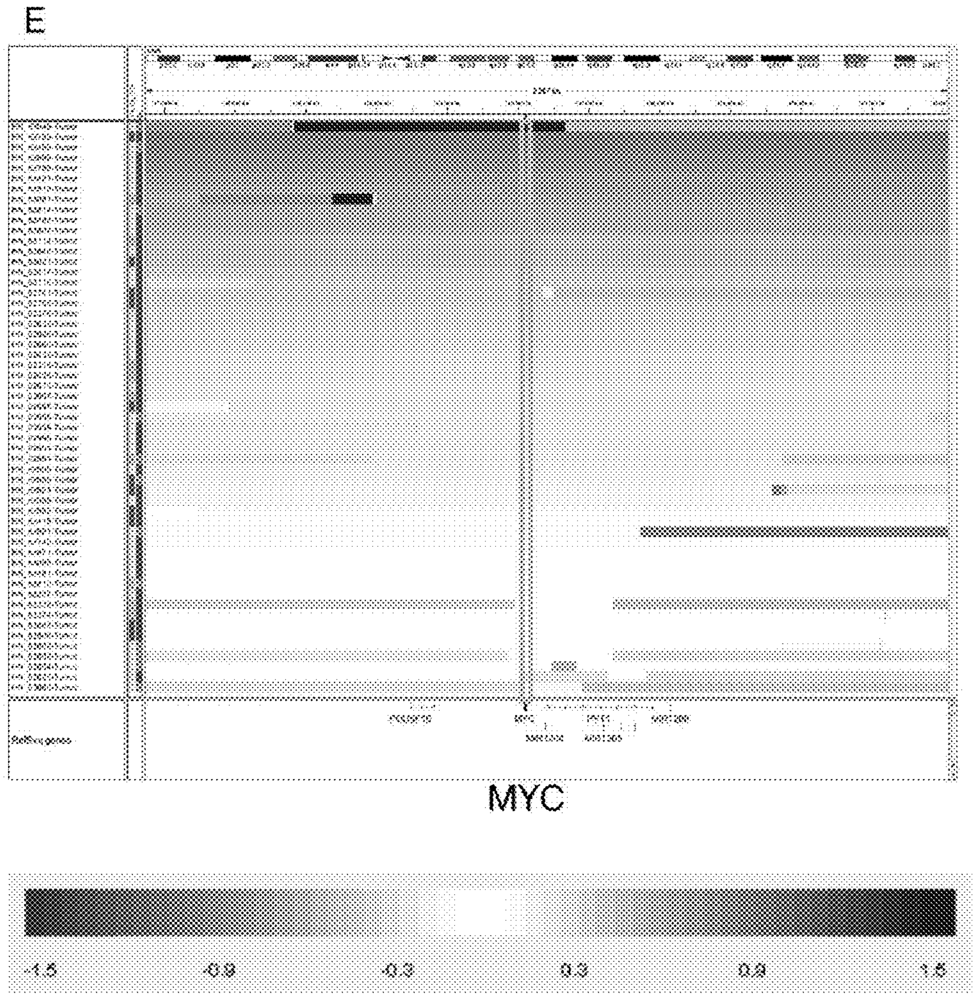
Figure 4F:
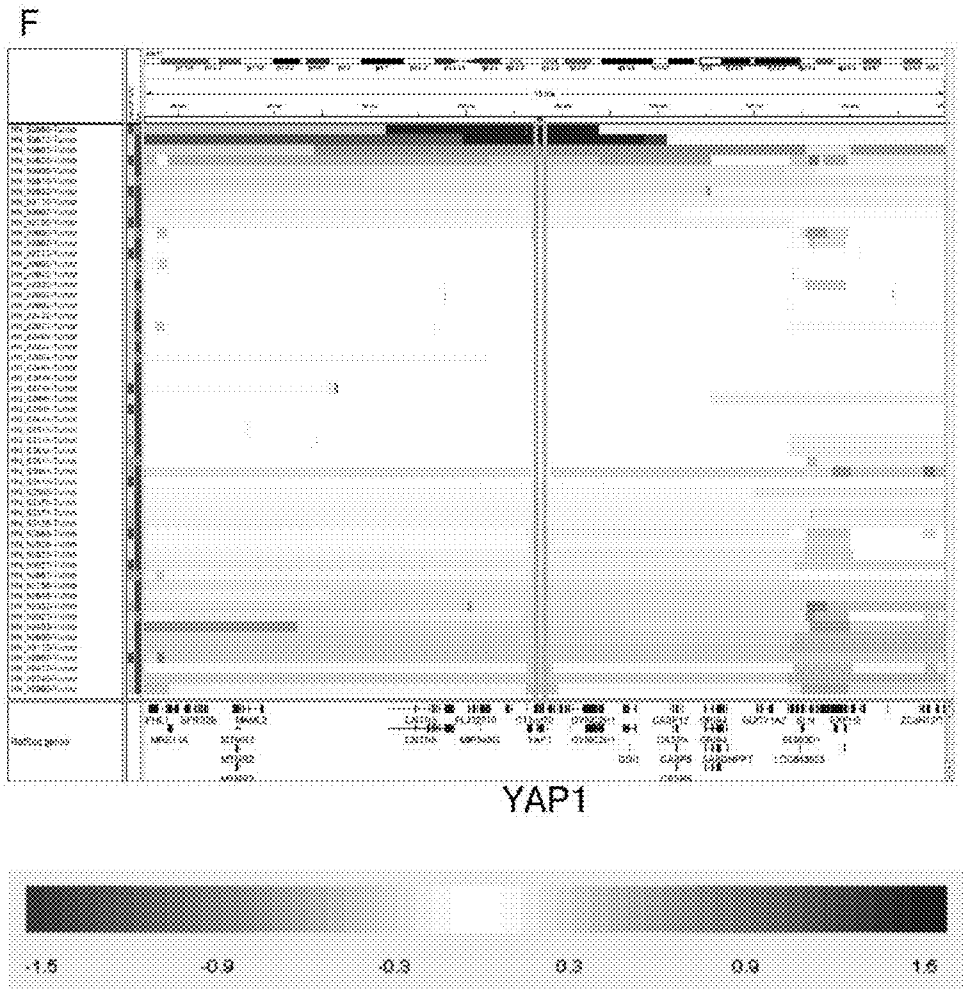
Figure 4G:
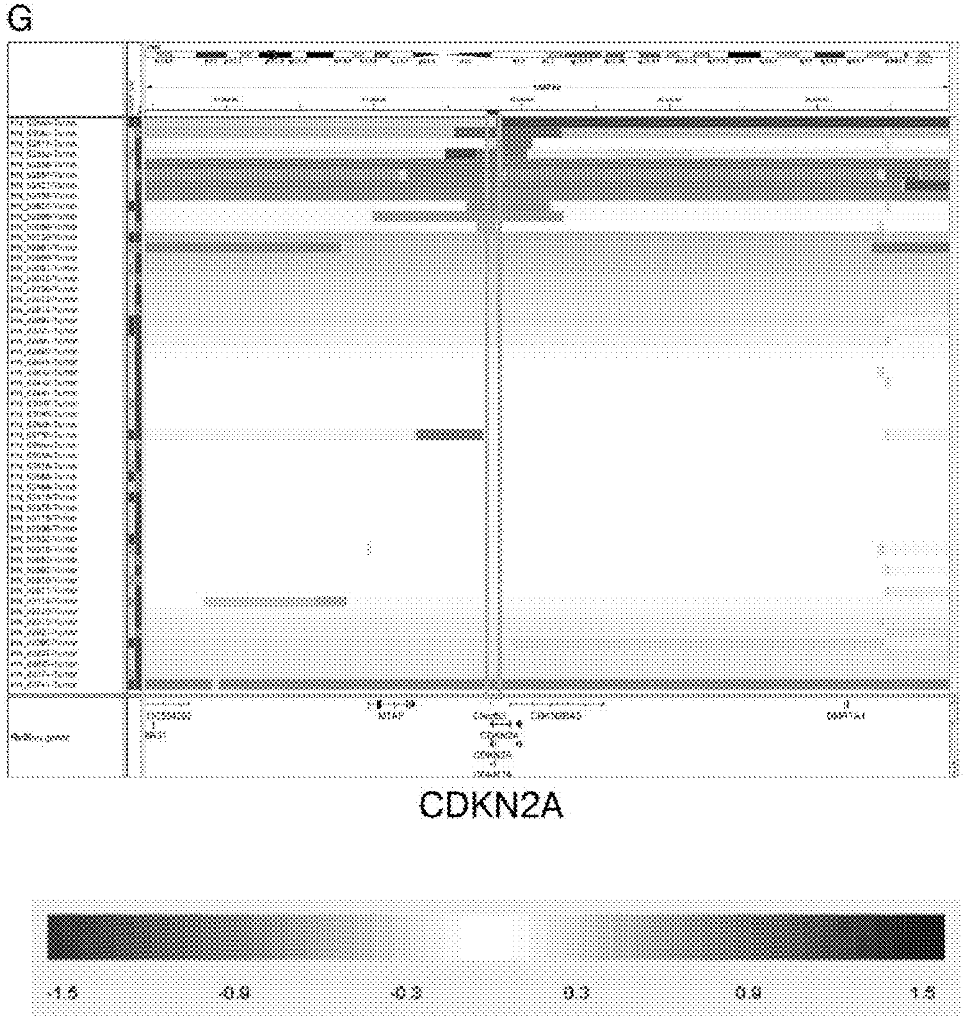

To explore their biological significance, Applicants first considered mutated HNSCC genes that also undergo frequent genetic alterations in other cancers. NOTCH1 was particularly noteworthy: point mutations affecting this gene occurred in 11% of the HNSCC tumors (FIG. 2-3 and FIG. 22A-B), and focal deletions were seen in two additional tumors (FIG. 2). Previous evidence from animal models had implicated Notch dysregulation in cutaneous squamous cell carcinoma (9) but somatic NOTCH1 mutations had not previously been identified in squamous malignancies. In addition, Applicants found non-synonymous point mutations in NOTCH2 or NOTCH3 in 11% of the samples (FIGS. 2, 3 and 22A-B) and a focal deletion of NOTCH3 in one additional case (FIG. 2). Whereas NOTCH1 contains activating mutations in T-cell acute lymphoblastic leukemia and chronic lymphocytic leukemia (10, 11) and NOTCH2 contains activating mutations in diffuse large B-cell lymphoma (12), the mutations in HNSCC appeared to be loss-of-function mutations, consistent with those recently described for myeloid leukemia (13).

Several NOTCH1 nonsense mutations in HNSCC are predicted to generate truncated proteins that lack the C-terminal ankyrin repeat domain, a region critical for transactivation of target genes (14) (FIG. 2). Five additional mutations (four missense and one in-frame deletion) cluster in highly conserved residues situated within or nearby the extracellular ligand binding domain (FIG. 2). Two others are splice-site mutations that may generate truncated proteins or delete critical functional residues (e.g., ligand binding or activation by proteolytic cleavage; FIG. 2). Together, these findings suggested that NOTCH dysregulation—and more generally mechanisms governed by NOTCH signaling—contribute to the genesis or progression of HNSCC.

To further interpret the mutations identified in HNSCC, Applicants looked for functionally related 'gene sets' harboring an excess of mutations. For this purpose, Applicants considered an expanded list of 76 genes ($q<0.25$;) and looked for enrichment in functional gene sets. The highest-scoring gene set contained genes related to epidermal development The significantly mutated genes ($q<0.25$) in this gene set included NOTCH1, IRF6, and TP63. These genes are all clearly related to squamous differentiation. The most abundant TP63 protein product in squamous epithelia, known as ΔNp63, promotes renewal of basal keratinocytes by a mechanism that requires down regulation of NOTCH1 and CDKN2A (15-17). IRF6, in turn, has been implicated in the proteasomal degradation of ΔNp63 (18). Furthermore, terminal differentiation in squamous epithelia is induced in response to genotoxic stress by a mechanism involving p53-dependent transactivation of NOTCH1—an activity antagonized by ΔNp63 (19). Because HNSCC involves transformation of the squamous epithelial lineage, which is histologically similar to the epidermis, these findings led us to hypothesize that mutations in such genes disrupt a stratified squamous development/differentiation program in precursor cells of this malignancy.

Further inspection of recurrent mutations identified eleven additional genes carrying disruptive mutations that function in the squamous differentiation program. The evidence includes mouse knockouts with defects in squamous epithelial differentiation (Notch1, Notch2, Irf6, Tp63, Ripk4, Cdh1, Ezh2, and Dicer1) (FIG. 3A) (20-25); human germline mutations causing orofacial clefting syndromes (IRF6, TP63, CDH1, and MLL2) (26) and knockdown or deregulated expression leading to a differentiation block and increased proliferation in cultured human keratinocytes (TP63, NOTCH1, IRF6, MED1) (15, 27). Thus, many mutated genes in HNSCC may govern squamous differentiation. These mutations may promote an immature and more proliferative basal-like phenotype, consistent with known stages of progression and markers of differentiation in HNSCC (FIG. 3B).

Applicants also found recurrent mutations in less well-characterized genes. For example, mutations in SYNE1 and SYNE2 were observed in 20% and 8% of HNSCC samples, respectively (FIGS. 9 and 22A-B). These genes have been implicated in the regulation of nuclear polarity (28), a process that operates upstream of NOTCH1 in squamous epithelia (29) (FIG. 3B). RIMS2 and PCLO mutations were seen in 11% and 12% of cases, respectively; the corresponding proteins mediate calcium sensing (30), another crucial process for terminal squamous differentiation (20).

Beyond the genes directly involved in squamous differentiation, Applicants found mutations involving two apoptosis-related genes: CASP8 (8%) and DDX3X (4%) (FIG. 9). Thus, suppression of apoptosis may also contribute to HNSCC pathogenesis, perhaps in concert with disrupted squamous maturation (FIG. 3B). The histone methyltransferases PRDM9 (11%) and EZH2 (6%) also show highly significant mutation rates.

Viral infection by HPV figures prominently into the etiology of a subset of HNSCC, and is most frequently detected by in situ hybridization (ISH) or p16 immunohistochemistry. Applicants reasoned that HNSCC genome sequencing might also offer a robust HPV detection method. Applicants therefore utilized the PathSeq algorithm (31) and a viral sequence database to identify HNSCC sequencing reads that aligned to HPV genomes. Applicants observed HPV-16 sequence reads in 14 tumors (19%) (range: 1-40,000 reads), 11 of which were also positive by HPV-16 PCR ($p<0.0001$, Kappa test;). The three tumors that were HPV-negative by PCR had very low HPV-16 sequence read counts (FIG. 12); this may reflect reduced HPV dosage or technical contamination. Applicants observed an inverse correlation between HPV status (determined by sequencing) and TP53 mutation, as shown previously (32) ($p=0.001$, Fisher's exact test). These data underscore the potential utility of massively parallel sequencing to detect both human and non-human etiologic agents in tumor specimens.

Given that NOTCH pathway inhibitors have entered clinical trials, the discovery of loss-of-function NOTCH1 mutations in HNSCC may have important therapeutic implications. A recent clinical trial of a gamma secretase inhibitor (which inhibits NOTCH) was halted in part due to an increased frequency of skin cancers in the treatment arm (33). This clinical observation is consistent with those from mouse models, in which cutaneous knockout of NOTCH1 promotes skin tumor formation (24). Applicants' results suggest that patients taking gamma secretase inhibitors may require monitoring for the development of both cutaneous and head/neck squamous malignancies.

Despite the anatomical distinctions that dominate current clinical management of HNSCC, Applicants' results point to several unifying features at the molecular level. For example, TP53 inactivation—either through somatic mutation or HPV infection—appears nearly universal in this malignancy. The present invention suggests that disruption of the squamous differentiation program may represent an additional overarching feature that occurs by numerous genetic mechanisms across tumors from multiple anatomic sites. Thus, HNSCC pathogenesis may involve a maturation arrest or a lineage dependency similar to that seen in other cancer types (34). However, HNSCC appears to be unusual in that the mutational etiology is diverse, in contrast to leukemia and prostate cancer where developmental pathologies appear to be caused by lesions in only a few target genes. Rational therapeutic avenues targeting this block in squamous differentiation may require synthetic lethal approaches to identify specific cellular dependencies arising from NOTCH inactivation, TP63 alteration, or other events that deregulate the program.

A "transcriptional activator" may be a DNA-binding protein that regulates one or more genes by increasing the rate of transcription. The activator may increase transcription by virtue of a connected domain which assists in the formation of the RNA polymerase holoenzyme, or may operate through a coactivator. A coactivator binds the DNA-binding activator and contains the domain assisting holoenzyme formation. A particular activator may bind one or more specific coactivators.

A "nuclease" may be an enzyme capable of cleaving the phosphodiester bonds between the nucleotide subunits of nucleic acids.

A "tumor cell", also known as a "cell with a proliferative disorder", may refer to a cell which proliferates at an abnormally high rate. A new growth which may comprise tumor cells is a tumor, also known as cancer. A tumor is an abnormal tissue growth, generally forming a distinct mass, that grows by cellular proliferation more rapidly than normal tissue growth. A tumor may show partial or total lack of structural organization and functional coordination with normal tissue. As used herein, a tumor is intended to encompass hematopoietic tumors as well as solid tumors.

A tumor may be benign (benign tumor) or malignant (malignant tumor or cancer). Malignant tumors can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias and lymphomas.

A "proliferative disorder" may be a disease or condition caused by cells which grow more quickly than normal cells, i.e., tumor cells. Proliferative disorders may include benign tumors and malignant tumors. When classified by structure of the tumor, proliferative disorders include solid tumors and hematopoietic tumors.

A "chemotherapeutic agent" or "chemotherapeutic drug" may be any chemical compound used in the treatment of a proliferative disorder. "Treating a proliferative disorder" means alleviating or eliminating the symptoms of a proliferative disorder, or slowing down the progress of a proliferative disorder.

A "metastatic tumor" may be a tumor that has metastasized from a tumor located at another place in the same animal.

An "effective amount" may be an amount of a chemotherapeutic agent which is sufficient to result in the intended effect. For a chemotherapeutic agent used to treat a disease, an efficient amount is an amount sufficient to alleviate or eliminate the symptoms of the disease, or to slow down the progress of the disease.

The invention provides a method for treating head and neck squamous cell carcinoma (HNSCC), or its associated premalignant lesions in a subject. Therapeutic compounds are administered prophylactically or therapeutically to subject suffering from at risk of (or susceptible to) developing HNSCC. Such subjects are identified using standard clinical methods or by detecting the mutations described herein.

The therapeutic method includes decreasing the expression, or function, or both, of one or more gene products of genes whose expression is aberrantly increased ("overexpressed gene") in expression is inhibited in any of several ways known in the art. For example, expression is inhibited by administering to the subject a nucleic acid that inhibits, or antagonizes, the expression of the overexpressed gene or genes, e.g., an antisense oligonucleotide which disrupts expression of the overexpressed gene or genes. Alternatively, function of one or more gene products of the overexpressed genes is inhibited by administering a compound that binds to or otherwise inhibits the function of the gene products. For example, the compound is an antibody which binds to the overexpressed gene product, e.g., a cell surface protein or gene products and inhibits an activity of function of the gene product, e.g., binding to a cognate receptor. In a preferred embodiment, the compound is a transcriptional activator-like effector (TALE) nuclease that specifically targets one of the genes overexpressed in HNSCC. The design and construction of the TALE is known in the art. For example as described in Zhang et al. *Nature Biotechnology* 29, 149-153 (2011), and Miller et al. *Nature Biotechnology* 29, 143-143 (2011) the contents of which are incorporated by reference in their entireties. Administration of non-naturally occurring compositions or compounds that comprise TALE polypeptides that may alter gene expression of a specific genomic locus of interest may counter the effects of aberrantly-overexpressed gene or genes in the subjects and improves the clinical condition of the subject.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context.

As used herein the term "wild type" is a term of the art understood by skilled persons and means the typical form of an organism, strain, gene or characteristic as it occurs in nature as distinguished from mutant or variant forms. Certain aspects of methods of the invention relate to the delivery of a wild type copy of a mutant gene to a cell, a tissue or an organism.

As used herein, the term "domain" or "protein domain" refers to a part of a protein sequence that may exist and function independently of the rest of the protein chain.

In advantageous embodiments of the invention, the methods provided herein use isolated, non-naturally occurring, recombinant or engineered DNA binding proteins that comprise Transcription activator-like receptor (TALE) monomers or variant TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. A general representation of a TALE monomer which is comprised within the DNA binding domain is $X_{1-11}$-$(X_{12}X_{13})$-$X_{14-33\ or\ 34\ or\ 35}$, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as $(X_{1-11}$-$(X_{12}X_{13})$-$X_{14-33\ or\ 34\ or\ 35})_z$, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), monomers with an RVD of NG preferentially bind to thymine (T), monomers with an RVD of HD preferentially bind to cytosine (C) and monomers with an RVD of NN preferentially bind to both adenine (A) and guanine (G). In yet another embodiment of the invention, monomers with an RVD of IG preferentially bind to T. Thus, the number and order of the polypeptide monomer repeats in the nucleic acid binding domain of a TALE determines its nucleic acid target specificity. In still further embodiments of the invention, monomers with an RVD of NS recognize all four base pairs and may bind to A, T, G or C. The structure and function of TALEs is further described in, for example, Moscou et al., *Science* 326:1501 (2009); Boch et al., *Science* 326:1509-1512 (2009); and Zhang et al., *Nature Biotechnology* 29:149-153 (2011), each of which is incorporated by reference in its entirety.

The polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, monomers having RVDs of H*, HA, KA, N*, NA, NC, NS, RA, and S* bind to adenine, guanine, cytosine and thymine with comparable affinity.

Figure 13A:
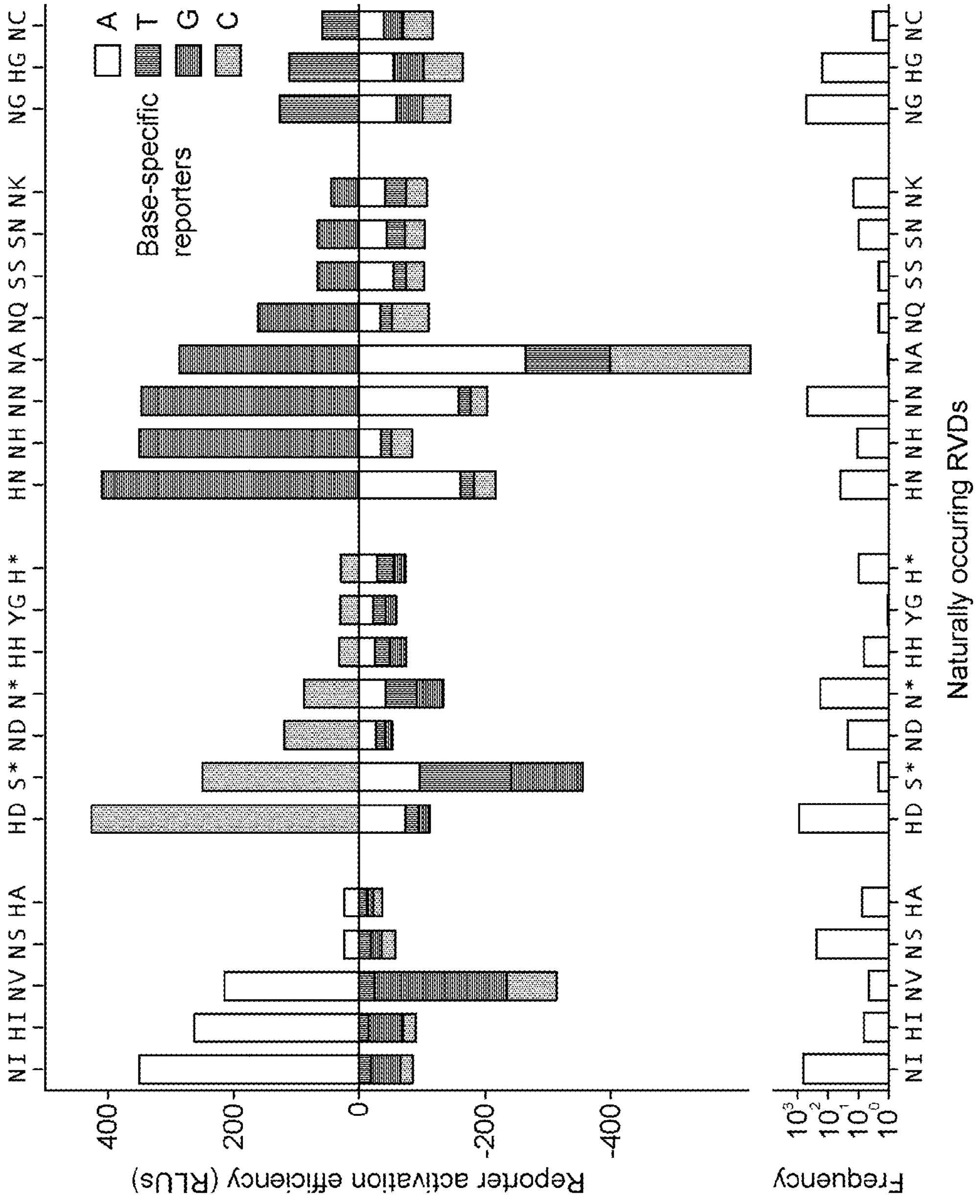
FIG. 13A shows the base-preference of various RVDs as determined using the Applicants' RVD screening system.
Figure 13B:
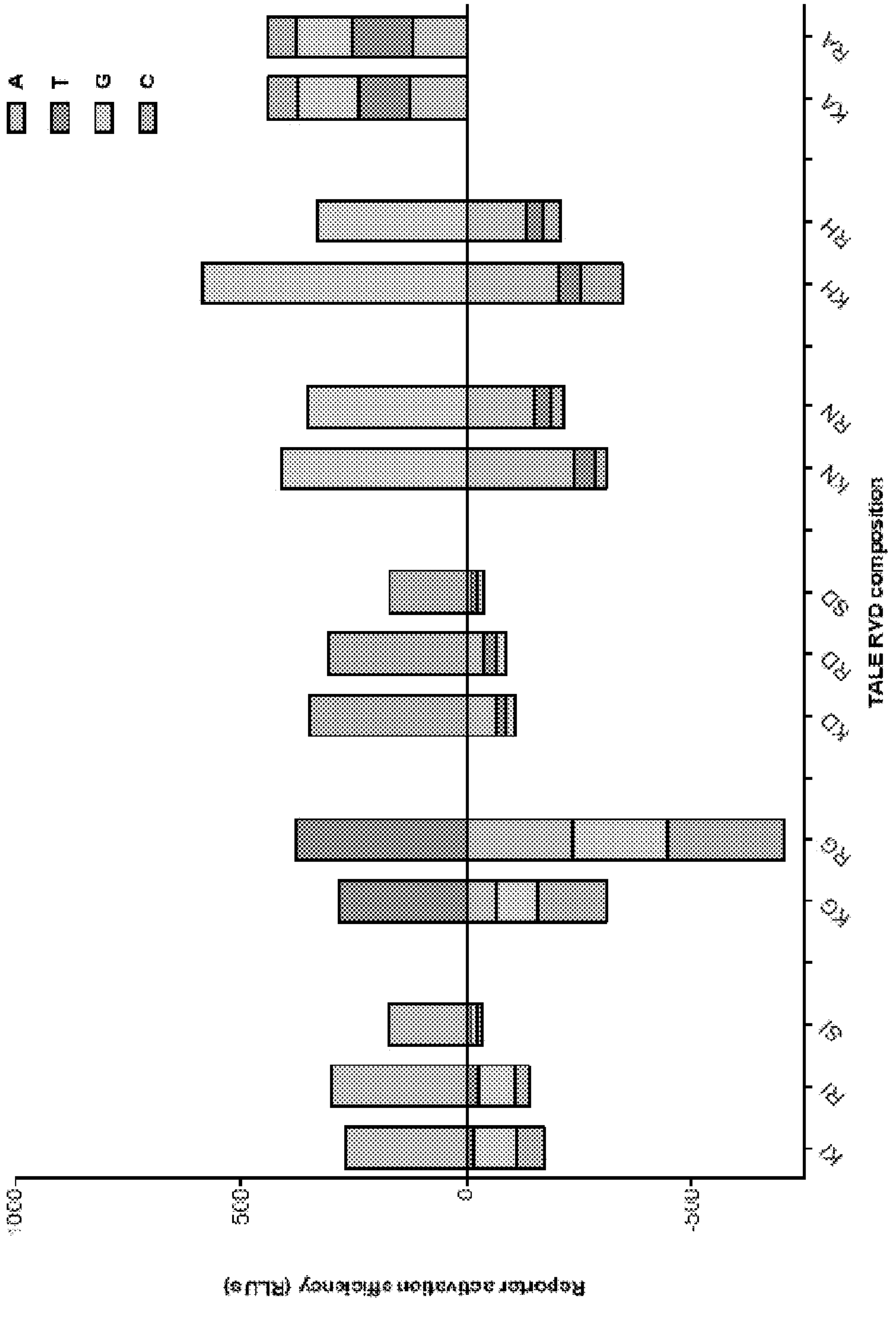
FIG. 13B shows the base-preference of additional RVDs as determined using the Applicants' RVD screening system.

In even more advantageous embodiments of the invention the RVDs that have a specificity for adenine are NI, RI, KI, HI, and SI. In more preferred embodiments of the invention, the RVDs that have a specificity for adenine are HN, SI and RI, most preferably the RVD for adenine specificity is SI. In even more preferred embodiments of the invention the RVDs that have a specificity for thymine are NG, HG, RG and KG. In further advantageous embodiments of the invention, the RVDs that have a specificity for thymine are KG, HG and RG, most preferably the RVD for thymine specificity is KG or RG. In even more preferred embodiments of the invention the RVDs that have a specificity for cytosine are HD, ND, KD, RD, HH, YG and SD. In a further advantageous embodiment of the invention, the RVDs that have a specificity for cytosine are SD and RD. Refer to FIG. 13B for representative RVDs and the nucleotides they target to be incorporated into the most preferred embodiments of the invention. In a further advantageous embodiment the variant TALE monomers may comprise any of the RVDs that exhibit specificity for a nucleotide as depicted in FIG. 13A. All such TALE monomers allow for the generation of degenerative TALE polypeptides able to bind to a repertoire of related, but not identical, target nucleic acid sequences. In still further embodiments of the invention, the RVD NT may bind to G and A. In yet further embodiments of the invention, the RVD NP may bind to A, T and C. In more advantageous embodiments of the invention, at least one selected RVD may be NI, HD, NG, NN, KN, RN, NH, NQ, SS, SN, NK, KH, RH, HH, KI, HI, R1, SI, KG, HG, RG, SD, ND, KD, RD, YG, HN, NV, NS, HA, S*, N*, KA, H*, RA, NA or NC.

Figure 14:
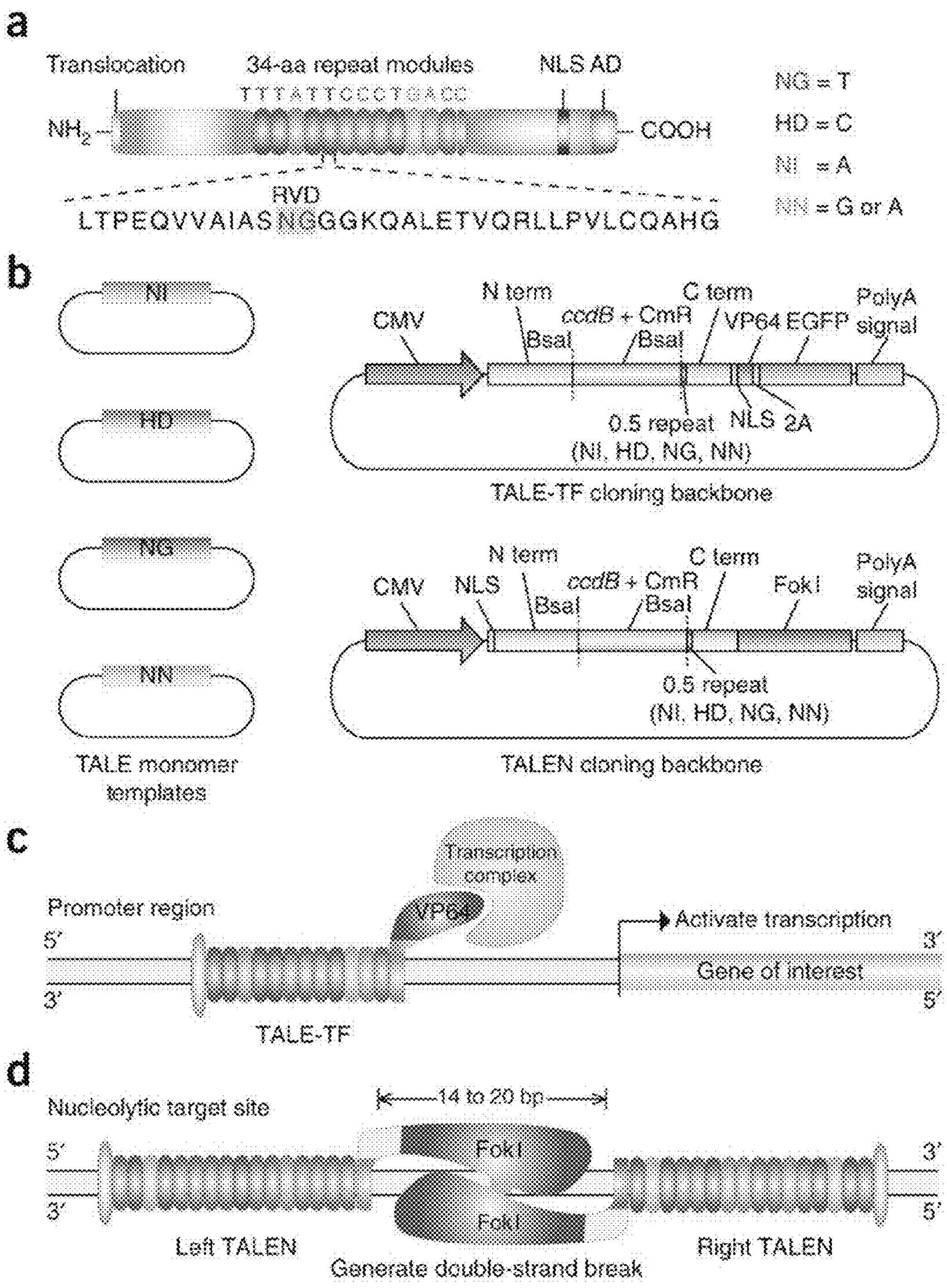
FIG. 14 shows in (a) Natural structure of TALEs derived from *Xanthomonas* sp. Each DNA-binding module consists of 34 amino acids, where the RVDs in the 12th and 13th amino acid positions of each repeat specify the DNA base being targeted according to the cipher NG=T, HD=C, NI=A, and NN=G or A. The DNA-binding modules are flanked by nonrepetitive N and C termini, which carry the translocation, nuclear localization (NLS) and transcription activation (AD) domains. A cryptic signal within the N terminus specifies a thymine as the first base of the target site. Figure discloses SEQ ID NOS 35-36, respectively, in order of appearance. (b) The TALE toolbox allows rapid and inexpensive construction of custom TALE-TFs and TALENs. The kit consists of 12 plasmids in total: four monomer plasmids to be used as templates for PCR amplification, four TALE-TF and four TALEN cloning backbones corresponding to four different bases targeted by the 0.5 repeat. CMV, cytomegalovirus promoter; N term, nonrepetitive N terminus from the Hax3 TALE; C term, nonrepetitive C terminus from the Hax3 TALE; BsaI, type IIs restriction sites used for the insertion of custom TALE DNA-binding domains; ccdB+CmR, negative selection cassette containing the ccdB negative selection gene and chloramphenicol resistance gene; NLS, nuclear localization signal; VP64, synthetic transcriptional activator derived from VP16 protein of herpes simplex virus; 2A, 2A self-cleavage linker; EGFP, enhanced green fluorescent protein; polyA signal, polyadenylation signal; FokI, catalytic domain from the FokI endonuclease. (c) TALEs can be used to generate custom TALE-TFs and modulate the transcription of endogenous genes from the genome. The TALE DNA-binding domain is fused to the synthetic VP64 transcriptional activator, which recruits RNA polymerase and other factors needed to initiate transcription. (d) TALENs can be used to generate site-specific double-strand breaks to facilitate genome editing through nonhomologous repair or homology directed repair. Two TALENs target a pair of binding sites flanking a 16-bp spacer. The left and right TALENs recognize the top and bottom strands of the target sites, respectively. Each TALE DNA-binding domain is fused to the catalytic domain of FokI endonuclease; when FokI dimerizes, it cuts the DNA in the region between the left and right TALEN-binding sites.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 14). Therefore, it follows that the length of the nucleic acid or DNA being targeted is equal to the number of full monomers plus two.

For example, nucleic acid binding domains can be engineered to contain 5, 6, 7, 8, 9, 10, 11, 12, 13, 14, 15, 16, 17, 18, 19, 20, 21, 22, 23, 24, 25, or more polypeptide monomers arranged in a N-terminal to C-terminal direction to bind to a predetermined 5, 6, 7, 8, 9, 10, 11, 12, 13, 14, 15, 16, 17, 18, 19, 20, 21, 22, 23, 24, 25 nucleotide length nucleic acid sequence. In more advantageous embodiments of the invention, nucleic acid binding domains can be engineered to contain 5, 6, 7, 8, 9, 10, 11, 12, 13, 14, 15, 16, 17, 18, 19, 20, 21, 22, 23, 24, 25, 26 or more full length polypeptide monomers that are specifically ordered or arranged to target nucleic acid sequences of length 7, 8, 9, 10, 11, 12, 13, 14, 15, 16, 17, 18, 19, 20, 21, 22, 23, 24, 25, 26, 27 and 28 nucleotides, respectively. In certain embodiments the polypeptide monomers are contiguous. In some embodiments, half-monomers can be used in the place of one or more monomers, particularly if they are present at the C-terminus of the TALE polypeptide.

Figure 16:
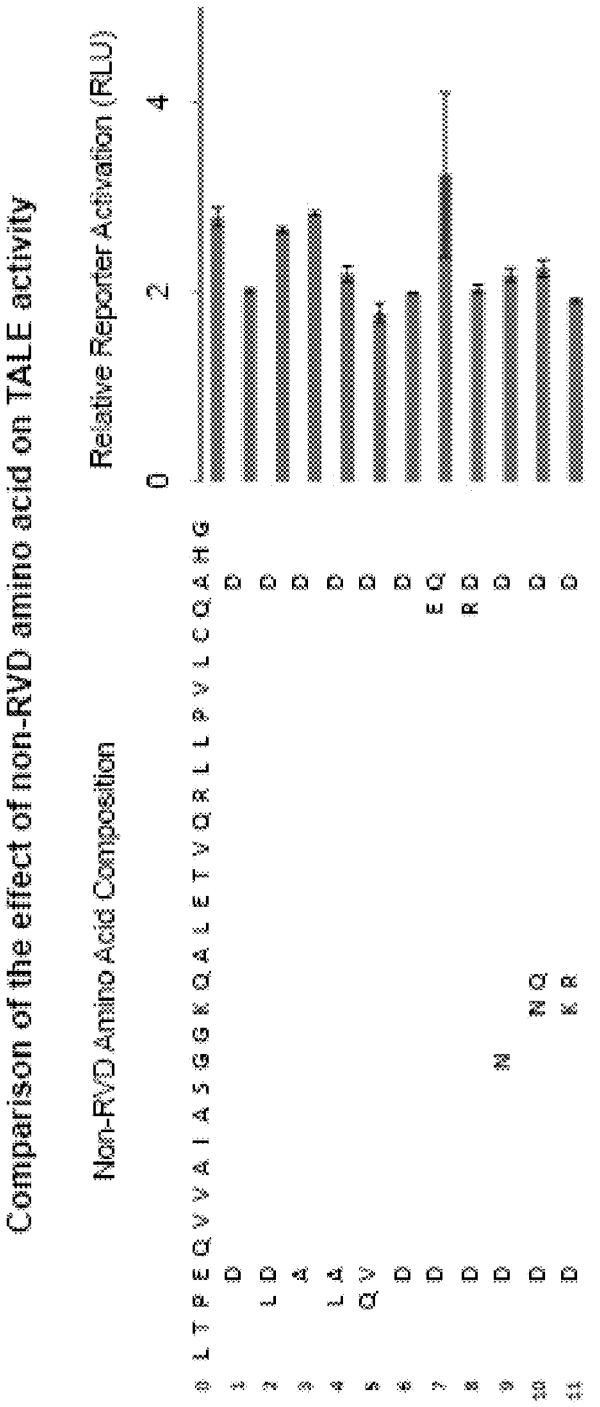
FIG. 16 shows the comparison of the effect of non-RVD amino acid on TALE activity. Figure discloses SEQ ID NOS 38, 37, 44, 41, 67, 268, 37, 42, 157, 269, 74 and 270, respectively, in order of appearance.

Polypeptide monomers are generally 33, 34 or 35 amino acids in length. With the exception of the RVD, the amino acid sequences of polypeptide monomers are highly conserved or as described herein, the amino acids in a polypeptide monomer, with the exception of the RVD, exhibit patterns that effect TALE activity, the identification of which may be used in preferred embodiments of the invention. Representative combinations of amino acids in the monomer sequence, excluding the RVD, are shown by the Applicants to have an effect on TALE activity (FIG. 16). In more preferred embodiments of the invention, when the DNA binding domain comprises $(X_{1-11}\text{-}X_{12}X_{13}\text{-}X_{14-33\ or\ 34\ or\ 35})_z$, wherein $X_{1-11}$ is a chain of 11 contiguous amino acids, wherein $X_{12}X_{13}$ is a repeat variable diresidue (RVD), wherein $X_{14-33\ or\ 34\ or\ 35}$ is a chain of 21, 22 or 23 contiguous amino acids, wherein z is at least 5 to 26, then the preferred combinations of amino acids are [LTLD] (SEQ ID NO: 1) or [LTLA] (SEQ ID NO: 2) or [LTQV] (SEQ ID NO: 3) at $X_{14}$, or [EQHG] (SEQ ID NO: 4) or [RDHG] (SEQ ID NO: 5) at positions $X_{30-33}$ or $X_{31-34}$ or $X_{32-35}$. Furthermore, other amino acid combinations of interest in the monomers are [LTPD] (SEQ ID NO: 6) at $X_{1-4}$ and [NQALE] (SEQ ID NO: 7) at $X_{16-20}$ and [DHG] at $X_{32-34}$ when the monomer is 34 amino acids in length. When the monomer is 33 or 35 amino acids long, then the corresponding shift occurs in the positions of the contiguous amino acids [NQALE] (SEQ ID NO: 7) and [DHG]; preferably, embodiments of the invention may have [NQALE] (SEQ ID NO: 7) at $X_{15-19}$ or $X_{17-21}$ and [DHG] at $X_{31-33}$ or $X_{33-35}$.

In still further embodiments of the invention, amino acid combinations of interest in the monomers, are [LTPD] (SEQ ID NO: 6) at $X_{1-4}$ and [KRALE] (SEQ ID NO: 9) at $X_{16-20}$ and [AHG] at $X_{32-34}$ or [LTPE] (SEQ ID NO: 10) at $X_{1-4}$ and [KRALE] (SEQ ID NO: 9) at $X_{16-20}$ and [DHG] at $X_{32-34}$ when the monomer is 34 amino acids in length. When the monomer is 33 or 35 amino acids long, then the corresponding shift occurs in the positions of the contiguous amino acids [KRALE] (SEQ ID NO: 9), [AHG] and [DHG]. In preferred embodiments, the positions of the contiguous amino acids may be ([LTPD] (SEQ ID NO: 6) at $X_{1-4}$ and [KRALE] (SEQ ID NO: 9) at $X_{15-19}$ and [AHG] at $X_{31-33}$) or ([LTPE] (SEQ ID NO: 10) at $X_{1-4}$ and [KRALE] (SEQ ID NO: 9) at $X_{15-19}$ and [DHG] at $X_{31-33}$) or ([LTPD] (SEQ ID NO: 6) at $X_{1-4}$ and [KRALE] (SEQ ID NO: 9) at $X_{17-21}$ and [AHG] at $X_{33-35}$) or ([LTPE] (SEQ ID NO: 10) at $X_{1-4}$ and [KRALE] (SEQ ID NO: 9) at $X_{17-21}$ and [DHG] at $X_{33-35}$) In still further embodiments of the invention, contiguous amino acids [NGKQALE] (SEQ ID NO: 11) are present at positions $X_{14-20}$ or $X_{13-19}$ or $X_{15-21}$. These representative positions put forward various embodiments of the invention and provide guidance to identify additional amino acids of interest or combinations of amino acids of interest in all the TALE monomers described herein (FIGS. 15A-F and 16).

Provided below are exemplary amino acid sequences of conserved portions of polypeptide monomers (SEQ ID NOS 12-24, respectively, in order of appearance). The position of the RVD in each sequence is represented by XX or by X* (wherein (*) indicates that the RVD is a single amino acid and residue 13 ($X_{13}$) is absent).

L T P A Q V V A I A S X X G G K Q A L E T V Q R L L P V L C Q D H G

L T P A Q V V A I A S X * G G K Q A L E T V Q R L L P V L C Q D H G

L T P D Q V V A I A N X X G G K Q A L A T V Q R L L P V L C Q D H G

L T P D Q V V A I A N X X G G K Q A L E T L Q R L L P V L C Q D H G

L T P D Q V V A I A N X X G G K Q A L E T V Q R L L P V L C Q D H G

L T P D Q V V A I A S X X G G K Q A L A T V Q R L L P V L C Q D H G

L T P D Q V V A I A S X X G G K Q A L E T V Q R L L P V L C Q D H G

L T P D Q V V A I A S X X G G K Q A L E T V Q R V L P V L C Q D H G

L T P E Q V V A I A S X X G G K Q A L E T V Q R L L P V L C Q A H G

L T P Y Q V V A I A S X X G S K Q A L E T V Q R L L P V L C Q D H G

-continued

L T R E Q V V A I A S X X G G K Q A L E T V Q R L L P V L C Q D H G

L S T A Q V V A I A S X X G G K Q A L E G I G E Q L L K L R T A P Y G

L S T A Q V V A V A S X X G G K P A L E A V R A Q L L A L R A A P Y G

A further listing of TALE monomers excluding the RVDs which may be denoted in a sequence ($X_{1-11}$-$X_{14-34}$ or $X_{1-11}$-$X_{14-35}$), wherein X is any amino acid and the subscript is the amino acid position is provided in FIG. 15A-F. The frequency with which each monomer occurs is also indicated.

As described in Zhang et al., *Nature Biotechnology* 29:149-153 (2011), TALE polypeptide binding efficiency can be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

M D P I R S R T P S P A R E L L S G P Q P D G V Q P T A D R G V S P

P A G G P L D G L P A R R T M S R T R L P S P P A P S P A F S A D S

F S D L L R Q F D P S L F N T S L F D S L P P F G A H H T E A A T G

E W D E V Q S G L R A A D A P P P T M R V A V T A A R P P R A K P A

P R R R A A Q P S D A S P A A Q V D L R T L G Y S Q Q Q Q E K I K P

K V R S T V A Q H H E A L V G H G F T H A H I V A L S Q H P A A L G

T V A V K Y Q D M I A A L P E A T H E A I V G V G K Q W S G A R A L

E A L L T V A G E L R G P P L Q L D T G Q L L K I A K R G G V T A V

E A V H A W R N A L T G A P L N (SEQ ID NO: 25)

An exemplary amino acid sequence of a C-terminal capping region is:

R P A L E S I V A Q L S R P D P A L A A L T N D H L V A L A C L G

G R P A L D A V K K G L P H A P A L I K R T N R R I P E R T S H R

V A D H A Q V V R V L G F F Q C H S H P A Q A F D D A M T Q F G M

S R H G L L Q L F R R V G V T E L E A R S G T L P P A S Q R W D R

I L Q A S G M K R A K P S P T S T Q T P D Q A S L H A F A D S L E

R D L D A P S P M H E G D Q T R A S (SEQ ID MO: 26)

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., *Nature Biotechnology* 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., *Nature Biotechnology* 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons can be conducted by eye, or more usually, with the aid of readily available sequence comparison programs. These commercially available computer programs can calculate percent (%) homology between two or more sequences and can also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention can be used to target the one or more functions or activities mediated by the effector domain to a particular target DNA sequence to which the nucleic acid binding domain specifically binds.

Figure 17:
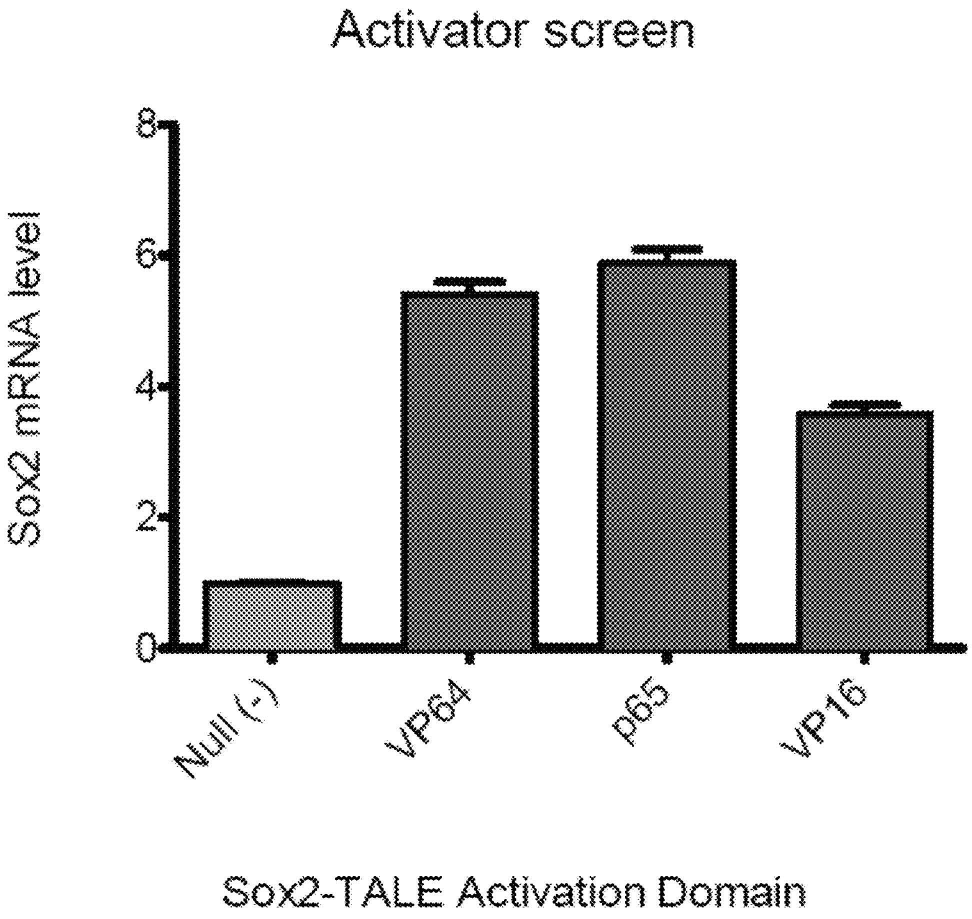
FIG. 17 shows an activator screen comparing levels of activation between VP64, p65 and VP16.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Krüppel-associated box (KRAB) or fragments of the KRAB domain. In some embodiments the effector domain is an enhancer of transcription (i.e. an activation domain), such as the VP16, VP64 or p65 activation domain. A graphical comparison of the effect these different activation domains have on Sox2 mRNA level is provided in FIG. 17.

As used herein, VP16 is a herpesvirus protein. It is a very strong transcriptional activator that specifically activates viral immediate early gene expression. The VP16 activation domain is rich in acidic residues and has been regarded as a classic acidic activation domain (AAD). As used herein, VP64 activation domain is a tetrameric repeat of VP16's minimal activation domain. As used herein, p65 is one of two proteins that the NF-kappa B transcription factor complex is composed of. The other protein is p50. The p65 activation domain is a part of the p65 subunit is a potent transcriptional activator even in the absence of p50. In certain embodiments, the effector domain is a mammalian protein or biologically active fragment thereof. Such effector domains are referred to as "mammalian effector domains."

In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

As described in Zhang et al., *Nature Biotechnology* 29:149-153 (2011), a TALE polypeptide having a nucleic acid binding domain and an effector domain can be used to target the effector domain's activity to a genomic position having a predetermined nucleic acid sequence recognized by the nucleic acid binding domain. In some embodiments of the invention described herein, TALE polypeptides are designed and used for targeting gene regulatory activity, such as transcriptional or translational modifier activity, to a regulatory, coding, and/or intergenic region, such as enhancer and/or repressor activity, that can affect transcription upstream and downstream of coding regions, and can be used to enhance or repress gene expression. For example, TALEs polypeptide can comprise effector domains having DNA-binding domains from transcription factors, effector domains from transcription factors (activators, repressors, co-activators, co-repressors), silencers, nuclear hormone receptors, and/or chromatin associated proteins and their modifiers (e.g., methylases, kinases, phosphatases, acetylases and deacetylases). In a preferred embodiment, the TALE polypeptide may comprise a nuclease domain. In a more preferred embodiment the nuclease domain is a non-specific FokI endonucleases catalytic domain.

In a further embodiment, useful domains for regulating gene expression may also be obtained from the gene products of oncogenes. In yet further advantageous embodiments of the invention, effector domains having integrase or transposase activity may be used to promote integration of exogenous nucleic acid sequence into specific nucleic acid sequence regions, eliminate (knock-out) specific endogenous nucleic acid sequence, and/or modify epigenetic signals and consequent gene regulation, such as by promoting DNA methyltransferase, DNA demethylase, histone acetylase and histone deacetylase activity. In other embodiments, effector domains having nuclease activity can be used to alter genome structure by nicking or digesting target sequences to which the polypeptides of the invention specifically bind, and can allow introduction of exogenous genes at those sites. In still further embodiments, effector domains having invertase activity can be used to alter genome structure by swapping the orientation of a DNA fragment.

In particularly advantageous embodiments, the polypeptides used in the methods of the invention may be used to target transcriptional activity. As used herein, the term "transcription factor" refers to a protein or polypeptide that binds specific DNA sequences associated with a genomic locus or gene of interest to control transcription. Transcription factors may promote (as an activator) or block (as a repressor) the recruitment of RNA polymerase to a gene of interest. Transcription factors may perform their function alone or as a part of a larger protein complex. Mechanisms of gene regulation used by transcription factors include but are not limited to a) stabilization or destabilization of RNA polymerase binding, b) acetylation or deacetylation of histone proteins and c) recruitment of co-activator or co-repressor proteins. Furthermore, transcription factors play roles in biological activities that include but are not limited to basal transcription, enhancement of transcription, development, response to intercellular signaling, response to environmental cues, cell-cycle control and pathogenesis. With regards to information on transcriptional factors, mention is made of Latchman and DS (1997) *Int. J. Biochem. Cell Biol.* 29 (12): 1305-12; Lee T I, Young R A (2000) *Annu. Rev. Genet.* 34: 77-137 and Mitchell P J, Tjian R (1989) *Science* 245 (4916): 371-8, herein incorporated by reference in their entirety.

HNSCC, like other forms of cancer, is associated with uncontrolled cell growth of abnormal cells. Uncontrolled cell growth may result from the overexpression of genes that are stimulate cell growth or by the underexpression of genes that normally curb cell growth. In one aspect, the growth of cells may be inhibited, e.g. reduced by contacting a cell with a composition containing a TALE nuclease that specifically targets one of the genes overexpressed in HNSCC. By inhibition of cell growth is meant the cell proliferates at a lower rate or has decreased viability compared to a cell not exposed to the composition. Cell growth may be measured by methods know in the art such as, the MTT cell proliferation assay or measurement of total GFP from GFP expressing cell lines.

Embodiments of the invention may include diagnostic methods wherein the specific mutations in HNSCC-associated genes are identified and then specifically targeted to alter gene expression to return expressed gene levels to a normal range. These diagnostic methods may comprise sequencing techniques. In another advantageous embodiment of the invention, the diagnostic information about these mutations may be used to select appropriate modes of therapy, e.g., the use of the mutational information can serve as a guide for selection of surgery, radiation, or delivery of a chemotherapeutic agent, an immunomodulatory agent or an agent that alleviates disease symptoms. The methods may be useful to alleviate the symptoms of a variety of cancers. Any cancer containing a HNSCC mutation as described herein may be amendable to treatment by the methods of the invention.

In further advantageous embodiments, methods of the invention may further comprise the administration of an immunomodulatory agent or a symptom alleviating agent. Immunomodulatory agents may include but are not limited to anti-inflammatory compounds, immunosuppresent drugs (e.g., antiproliferative or cytotoxic compounds, calcineurin inhibitors, glucocorticoids, antibodies etc.), Immunostimulant drugs (e.g., recombinant cytokines, Thalidomide. Levamisole etc.) and Tolerogens (e.g., soluble HLA, donor cell chimeras, costimulatory blockade etc.). Symptoms of conditions associated with cancer include but are not limited to nausea, pain, tiredness, breathlessness and lack of appetite. In preferred embodiments of the invention, the therapeutic methods may further comprise the delivery of an agent that mitigates nausea, pain, tiredness, breathlessness and lack of appetite. In a highly advantageous embodiment of the invention, the symptom alleviating agent may be an antiemetic or an analgesic.

In preferred embodiments, therapeutic methods of the invention may involve targeting the mutation itself: e.g., TALE nucleases or other genome editing technology (like zinc-finger proteins etc.) may be used to replace the mutation with a non-pathogenic base. These methods may be adopted for either loss or gain of function mutations. Preferably the mutations are associated with HNSCC-associated genes. In other preferred embodiments, particular genes or nucleic acid sequences may be delivered to reverse activity of the mutation. In certain embodiments of the invention, a non-pathogenic copy of the gene or nucleic acid sequence may be inserted into another locus of the genome a to counteract or replace the function of a loss of function mutation (i.e. insertion of a wild type copy of p53 or NOTCH into a tumor that lacks these genes). In yet more preferred embodiments of the invention, a sequence encoding either RNAi or a protein that reverses the activity of an aberrant gain of function mutation at a different locus may be delivered (i.e. engineered transcription factors or proteins which may bind and target aberrant protein products for degradation).

The therapeutic methods of the invention include increasing the expression, or function, or both of one or more gene products of genes whose function is decreased, either as a consequence of decreased abundance of protein, or as a consequence of aberrantly dysfunctional protein due to sequence or structural changes. ("gain of function" or "loss of function") ("underexpressed genes" or "repressed genes") in a HNSCC cell relative to normal cells of the same tissue type from which the HNSCC cells are derived. In these methods, the subject is treated with a therapeutically effective amount of a composition or compound, which increases the amount of one of more of the under expressed/repressed genes in the subject. Administration can be systemic or local. Therapeutic compositions or compounds include a polypeptide product of an underexpressed gene, or a biologically active fragment thereof a nucleic acid encoding an underexpressed gene and having expression control elements permitting expression in specific cells; for example an agent which increases the level of expression of such gene endogenous to the cells (i.e., which up-regulates expression of the underexpressed gene or genes). In a preferred embodiment, the composition or compound may include a TALE transcription factor that specifically targets one of the genes underexpressed in HNSCC. The design and construction of the TALE polypeptide is known in the art. For example as described in Zhang et al. *Nature Biotechnology* 29, 149-153 (2011), and Miller et al. *Nature Biotechnology* 29, 143-143 (2011) the contents of which are incorporated by reference in their entireties. Administration of such compounds counter the effects of aberrantly-under expressed of the gene or genes in the subjects and improves the clinical condition of the subject.

These modulatory methods may be performed ex vivo or in vitro (e.g., by culturing the cell with the agent) or, alternatively, in vivo (e.g., by administering the agent to a subject). The method involves administering a protein or combination of proteins or a nucleic acid molecule or combination of nucleic acid, molecules as therapy to counteract aberrant expression or activity of the differentially expressed genes.

Increased or decreased levels may be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of a gene whose expression is altered). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., northern assays, dot blots, in situ hybridization, etc.).

Prophylactic administration occurs prior to the manifestation of overt clinical symptoms of disease, such that a disease or disorder is prevented or, alternatively, delayed in its progression.

Therapeutic methods may include contacting a cell with an agent that modulates one or more of the activities of the gene products of HNSCC associated genes. An agent that modulates protein activity includes a nucleic acid or a protein, a naturally-occurring cognate ligand of these proteins, a peptide, a peptidomimetic, or other small molecule. For example, the agent stimulates one or more protein activities of one or more of a differentially underexpressed gene.

The chemotherapeutic agent may be an alkylating agent, anti-angiogenesis agent, anti-hormone (such as an anti-androgen), anti-metabolite, cell cycle inhibitor, growth factor inhibitor, intercalating antibiotic, mitotic inhibitor or topoisomerase inhibitor. If the chemotherapeutic agent is an alkylating agent, the alkylating agent may be an alkyl sulfonate (such as busulfan), a nitrogen mustard (such as chlorambucil, cyclophosphamide, mechlorethamine, melphalan or uracil mustard), a nitrosourea (such as carmustine, dacarbazine, lomustine, semustine or streptozocin). If the chemotherapeutic agent is an antimetabolite agent, the antimetabolite may be a folic acid analog (such as methotrexate), a purine analog (such as mercaptopurine or thioguanine) or a pyrimidine analog (such as 5-FU or cytarabine). If the chemotherapeutic agent is an anti-hormone, the anti-hormone may be diethylstilbestrol, ethinyl estradiol, fluoxymesterone, hydroxyprogesterone caproate, medroxyprogesterone acetate, magestrol acetate, prednisone, tamoxifen or testerone proprionate.

In other embodiments, the chemotherapeutic agent may be Adriamycin, Alkeran, Ara-C, Bevacizumab, BiCNU, Busulfan, CCNU, Calcitriol, Carboplatinum, Cetuximab (Erbitux™), Cisplatin, Cisplatinum, Cytoxan, Daunorubicin, DTIC, Erlotinib, 5-FU, Fludarabine, Gemcitabine (Gemzar), Herceptin, Hydrea, Idarubicin, Ifosfamide, Irinotecan (Camptosar, CPT-11), Leustatin, Methotrexate, Mithramycin, Mitomycin, Mitoxantrone, Navelbine, Nitrogen Mustard, Rituxan STI-571, Taxol (or other taxanes, such as docetaxel), Topotecan (Hycamtin), Taxotere, Velban, Vincristine, VP-16, Xeloda (Capecitabine) or Zevelin.

Treatment is efficacious if the treatment leads to clinical benefit such as, a decrease in size, prevalence, or metastatic potential of the tumor in the subject. When treatment is applied prophylactically, "efficacious" means that the treatment retards or prevents tumors from forming or prevents or alleviates a symptom of clinical symptom of the tumor. Efficaciousness is determined in association with any known method for diagnosing or treating the particular tumor type Pharmaceutical formulations include those suitable for oral, rectal, nasal, topical (including buccal and sub-lingual), vaginal or parenteral (including intramuscular, sub-cutaneous and intravenous) administration, or for administration by inhalation or insufflation. The formulations are optionally packaged in discrete dosage units Pharmaceutical formulations suitable for oral administration include capsules, cachets or tablets, each containing a predetermined amount of the active ingredient. Formulations also include powders, granules or solutions, suspensions or emulsions. The active ingredient is optionally administered as a bolus electuary or paste. Tablets and capsules for oral administration may contain conventional excipients such as binding agents, fillers, lubricants, disintegrant or wetting agents. A tablet may be made by compression or molding, optionally with one or more formulational ingredients. Compressed tablets may be prepared by compressing in a suitable machine the active ingredients in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. The tablets may optionally be formulated so as to provide slow or controlled release of the active ingredient therein. A package of tablets may contain one tablet to be taken on each of the month. The formulation or does of medicament varies with respect to the phase (probe or sucretary) of the menstrual cycle.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations for rectal administration may include suppositories with standard carriers such as cocoa butter or polyethylene glycol. Formulations for topical administration in the mouth, for example buccally or sublingually, include lozenges, which contain the active ingredient in a flavored base such as sucrose and acacia or tragacanth, and pastilles which may comprise the active ingredient in a base such as gelatin and glycerin or sucrose and acacia. For intra-nasal administration the compounds of the invention may be used as a liquid spray or dispersible powder or in the form of drops. Drops may be formulated with an aqueous or non-aqueous base also which may comprise one or more dispersing agents, solubilizing agents or suspending agents.

For administration by inhalation the compounds may be conveniently delivered from an insufflator, nebulizer, pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflators.

Other formulations include implantable devices and adhesive patches; which release a therapeutic agent.

When desired, the above described formulations, adapted to give sustained release of the active ingredient, may be employed. The pharmaceutical compositions may also contain other active ingredients such as antimicrobial agents, immunosuppressants or preservatives.

It should be understood that in addition to the ingredients particularly mentioned above, the formulations of this invention may include other agents conventional in the art having regard to the type of formulation in question, for example, those suitable for oral administration may include flavoring agents.

Preferred unit dosage formulations are those containing an effective dose, as recited below, or an appropriate fraction thereof, of the active ingredient.

For each of the aforementioned conditions, the compositions, e.g., polypeptides and organic compounds are administered orally or via injection at a dose of from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg. Nucleic acids, e.g., DNA constructs, are administered at a dose in the range of 0.005-50 mg/kg of body weight. Alternatively, an intravenous dose is in the range of 106-1022 copies if the nucleic acid molecule.

The dose employed will depend upon a number of factors, including the age and sex of the subject, the precise disorder or symptoms being treated, and its severity. Also the route of administration may vary depending upon the condition and its severity.

The present invention also relates to methods of identifying an agent for inhibiting cell growth of a HNSCC or its related premalignant lesions, which may comprise administering the agent to a cell culture expressing a HNSCC-associated gene is selected from FIG. 22A-B and determining if the agent decreases the function of the HNSCC-associated gene with aberrant gain-of-function or increases the function of the HNSCC-associated gene with aberrant loss-of-function. The aberrant gain-of-function HNSCC gene may be TP63, CCND1, CCNE1, MYC, YAP1, HRAS, PIK3CA or PIK3CG. The HNSCC-associated gene with aberrant loss-of-function may be NOTCH1, NOTCH 2, NOTCH 3, IRF6, CDKN2A, TP53, CASP8, PTEN, FAT1, RIPK4, EZH1, EZH2, MED1, MLL2, CDH1, FBXW7, PCLO, RIMS2 or RB1.

The agent for inhibiting cell growth of a head and neck cell carcinoma (HNSCC) or its related premalignant lesions may be an antibody, an antisense compound, a polynucleotide, a polypeptide or a small molecule. Advantageously, an antisense or polynucleotide may be a short hairpin RNA (shRNA) or a small interfering RNA (siRNA). The small molecule may be a molecule with a molecular weight of about 100 to about 1000 Daltons capable of inhibiting activity of a HNSCC-associated gene.

In advantageous embodiments of the invention, the agent for inhibiting cell growth may be small molecules or proteins which directly inhibit or alter the activity of protein products of mutant genes. In other advantageous embodiments, the agent may be small molecules or proteins which directly inhibit or alter the activity of interactors within complexes affected by mutant genes (e.g., CDK inhibitors for Retinoblastoma protein (RB) mutant tumors). In still further advantageous embodiments, the agent may be small molecules or proteins which exhibit synthetic lethality when used in the context conditional of a known mutation. (i.e. compound X might kill only tumor cells with a NOTCH mutation, via a mechanism not listed above).

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Materials and Methods

Clinical, Pathologic and Risk Exposure Information

Patient data that included tumor histology, type (primary versus recurrent), anatomical site/grade, tumor/nodal disease stage, and treatment history (e.g., prior radiotherapy or chemoradiotherapy) were obtained through the University of Pittsburgh Head and Neck SPORE neoplasm virtual repository (35), a database curated and maintained by the University of Pittsburgh Head and Neck Cancer Registrar. Patient tobacco and alcohol use histories and data were obtained through administered questionnaire or clinical chart review.

Samples.

Samples and clinical information were collected from consented patients and processed using protocols approved by the Institutional Review Boards of the University of Pittsburgh and the Broad Institute of MIT and Harvard. Patients diagnosed with pathologically confirmed squamous cell carcinoma of the oral cavity, oropharynx, hypopharynx, nasopharynx, nasal cavity and paranasal sinuses (sinonasal) or larynx (HNSCC) were considered for inclusion in this invention if at least 50 mg of fresh-frozen tumor tissue and 400 μL of frozen whole blood were available for study through the University of Pittsburgh Head and Neck tissue bank. Tumors with estimated 70% or greater tumor purity based upon cytologic smears sampled from one surface of the tumor by scraping (scrape prep) were considered for inclusion. DNA was isolated from tumors and whole blood using the DNeasy Blood and Tissue Kit (Qiagen). DNA quantity and quality were assessed by Pico Green assay and gel electrophoresis to assess for DNA degradation. DNA from 93 paired tumor/blood samples was deemed of adequate quantity and quality for sequence analysis. Of these 93 tumor/blood pairs, 92 were successfully sequenced (one pair was dropped due to insufficient coverage of the blood sample) and 74 were subsequently included in the whole exome sequencing analyses (see Sequence Data Processing below). A summary of subject clinical, pathologic and tobacco/alcohol use data are provided in Table 1.

Detecting Human Papilloma Virus (HPV) by In Situ Hybridization (ISH).

Formalin-fixed paraffin-embedded tissue blocks with evaluable tumor tissue were available for 65 of the 74 analyzed tumors. HPV status was assessed using an HPV pan-specific DNA probe (Dako, Wide Spectrum HPV DNA Probe Cocktail, Biotinylated), which recognizes HPV subtypes 6, 11, 16, 18, 31, 33, 35, 45, 51 and 52, and bright field in situ hybridization. Tumors with punctuate nuclear staining were scored as HPV-positive.

Identification of Virus-Derived Sequences Using PathSeq.

The PathSeq algorithm was applied to BAM files from whole exome sequencing data as described (36). Briefly, all sequencing reads that did not align to the human genome were aligned to a virus reference sequence database that was downloaded from NCBI Nucleotide (see the website of NCBI under the section Nucleotide) Here, the search term "'viruses' [porgn;_txid10239]" (on 2010-10-28) was used with the MAQ aligner (Release 0.5.0, default settings) (39). To minimize alignment artifacts, all aligned reads were subjected to a second-pass alignment using MegaBlast (Blast Tools version 2.2.23, cutoff expect value $10^{-29}$, word size 16).

Human Papilloma Virus Detection by Taqman PCR.

Figure 12:
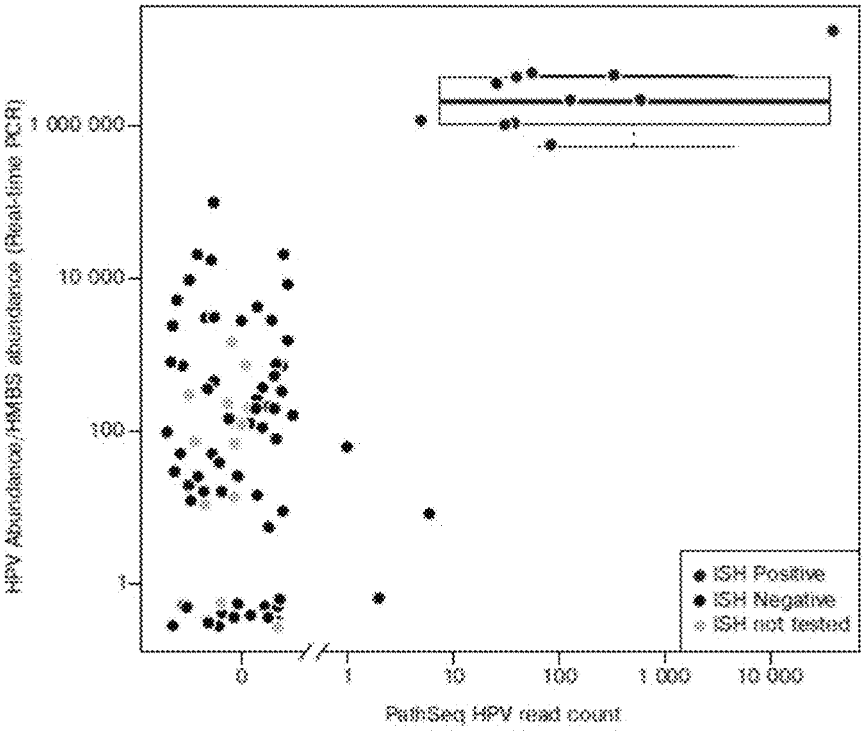
FIG. 12 shows HPV detection by real-time PCR. Results from three HPV detection methods are shown for 90 tumors. The results of HPV detection by in situ hybridization are indicated (red=positive; blue=negative). The x-axis shows on a log scale the number of reads that could be aligned to the HPV genome using PathSeq, from 0 (values artificially scattered), to 38,999. The y-axis shows the abundance of HPV sequences relative to a control gene present in the human genome, HMBS, as assessed by real-time PCR. The boxplot shows the distribution of real-time PCR values from the samples that were both positive by ISH and PathSeq. As a consequence, all values significantly differing from that distribution were confirmed as HPV negative. Of note, the one sample tested as negative by ISH, but positive by real-time PCR also tested positive by p16 immunohistochemistry and lacked a TP53 mutation, consistent with that tumor being infected with HPV.

The same DNA samples used for whole exome sequencing were also assessed for presence of HPV-16 E7 using primers based upon a validated quantitative real-time PCR based assay (37). The following primers and probes (Integrated DNA Technologies, San Diego, Calif., USA) were used: HPV16E7 Forward: 5'-AGC TCA GAG GAG GAG GAT GAA (SEQ ID NO: 27), HPV16E7 Reverse: 5'-GGT TAC AAT ATT GTA ATG GGC TC (SEQ ID NO: 28), HPV16E7 fluorescent probe: 5'-/56-FAM/CC AGC TGG A/ZEN/C AAG CAG AAC CGG/3IABkFQ (SEQ ID NOS 29-30, respectively). As a control, the following primers and a probe complementary to HMBS were used in independent reactions with the same DNA analyzed: HMBS Forward 5'-GCC TGC AGT TTG AAA TCA GTG (SEQ ID NO: 31), HMBS Reverse: 5'-CGG GAC GGG CTT TAG CTA (SEQ ID NO: 32), HMBS fluorescent probe: 5'-/56-FAM/TG GAA GCT A/ZEN/A TGG GAA GCC CAG TAC C/3IABkFQ (SEQ ID NOS 33-34, respectively). The real time PCR reactions were run using an ABI-7300 Real Time PCR machine (Applied Biosystems, Carlsbad, Calif., USA). Reactions were set up in 96-well plates using 25 μL volume, with each reaction consisting of 12.5 μL of 2× Taqman Gene Expression Master Mix (Applied Biosystems, Carlsbad, Calif., USA), 25 pmol each of the forward and reverse primer, and 5 pmol of the fluorescent probe. One μL of 20 ng/genomic DNA was used in each reaction. An initial hold step of 10 minutes at 95° C. was followed by 43 cycles of 15 seconds at 95° C. and 60 seconds at 59° C. Ct thresholds were determined using the sequence detection system software (Applied Biosystems, Carlsbad, Calif., USA). A threshold Ct of positivity was set based upon known HPV-positive tumors (ISH+, p16+, and Pathseq+) (FIG. 12). Immunohistochemical (IHC) staining for P16 was performed on deparaffinized TMA sections after antigen retrieval (P16INK4 mAb G175-405, BD Pharmingen; 1:200). Tumor HPV status by ISH and PCR demonstrated 98.7% agreement for the 77 sequenced tumors evaluated using both techniques, with one sample being negative by ISH, but positive by PCR, p16 staining, and Pathseq. Tumor HPV status was therefore defined by HPV-16 PCR status (n=90) or by HPV ISH status for tumors with insufficient DNA for HPV-16 PCR assessment (n=2).

Mutation Rate and G-)T Transversion Frequency by HPV Status and Tumor Site.

Differences in total (synonymous and non synonymous) mutation rates and G-)T transversion frequencies between previously treated versus untreated HNSCC and HNSCC tumors that were either positive or negative for HPV were tested using separate rank sum tests. HPV tumor status was defined by HPV-16 PCR status. To determine whether mutation rates or G-)T transversion frequencies among tumors that were HPV-negative (n=63) differed for any of the tumor sites (oral cavity, oropharynx, hypopharynx, sinonasal or larynx), the Kruskal Wallis (KW) test was used. If the overall KW test indicated a statistically significant difference (P<0.05), differences between tumor sites were further explored. Those tumor sites that did not differ by the KW test were grouped, and a rank sum test was used to evaluate differences in rates/frequencies between the final two groups (larynx versus other sites).

Example 2

Sequence Data Generation

Quality Assessment of DNA and Tumor Purity

Concentrations of tumor and normal DNA were measured using PicoGreen® dsDNA Quantitation Reagent (Invitrogen, Carlsbad, Calif.). Applicants required a minimum DNA concentration of 60 ng/μL for sequencing. DNA sample quality was assessed by gel electrophoresis. Applicants prepared reserve stocks of each sample using whole genome amplification (WGA) for use in subsequent validation efforts, though the Illumina sequencing libraries were created with the native DNA. The identities of all tumor and normal DNA samples (native and WGA product) were confirmed by mass spectrometric fingerprint genotyping of 24 common SNPs (Sequenom, San Diego, Calif.). Finally, a subset of the tumor DNAs were hybridized to genome-wide human SNP microarrays (Affymetrix SNP Array 6.0) and analyzed as described previously (38). Samples having favorable expected statistical power for the detection of somatic point mutations were selected for WGS sequencing. These determinations were made using the estimated tumor purity and ploidy in the cancer clone by consideration of allelic copy information as reported by Affymetrix SNP6.0 analysis of tumor DNA. The two tumor samples selected for WGS had an estimated purity/ploidy of 0.78/2.1 (HN_62469) and 0.53/3.72 (HN_62699). The expected power to detect mutations at 30× coverage was calculated to be 0.9999 and 0.923 respectively.

Whole Genome Shotgun (WGS) Library Construction

Applicants sheared 1-3 μg of genomic DNA to a range of 100-700 bp using the Covaris E210 instrument. DNA fragments were end-repaired and phosphorylated, followed by adenylation of 3' ends. Standard paired end adaptors were ligated according to the manufacturer's protocol (Illumina). Applicants performed Qiagen min elute column based cleanups between all enzymatic steps. Adapter ligated fragments were purified with preparatory gel electrophoresis (4% agarose, 85 V, 3 hours) and two bands were excised (500-520 bp and 520-540 bp) resulting in two libraries per sample with inserts averaging 380 bp and 400 bp respectively. DNA was extracted from gel bands using Qiagen mini-elution columns. The entire volume of final purified fragments was enriched via PCR with Phusion polymerase for 10 cycles.

Each of the resulting WGS libraries was sequenced on an average of 16 lanes of an Illumina GAIT instrument. 101 bp paired-end reads were generated, with the aim of reaching 30× average genomic coverage of distinct molecules per sample. The actual mean coverage achieved was 34× in the tumors and 29× in the normals Whole Exome (WE) Capture Library Construction (Standard Procedure)

Applicants followed the procedure described in (39), adapted for production-scale exome capture library construction. Exome targets were generated based on CCDS+RefSeq genes (see the website of NCBI under the section Projects and under the sub-section CCDS as well as under the section RefSeq) representing 188,260 exons from −18,560 genes (93% of known, non-repetitive protein coding genes) and spanning −1% of the genome (32.7 Mb). DNA oligonucleotides were amplified by PCR and subjected to in vitro transcription in the presence of biotinylated UTP to generate single-stranded RNA "baits". Genomic DNA from primary tumor and patient-matched blood normal was sheared, ligated to Illumina sequencing adapters, and selected for lengths between 200-350 bp. This "pond" of DNA was hybridized with an excess of bait in solution. The "catch" was pulled down by magnetic beads coated with streptavidin and eluted as described previously (39, 40). The resulting exome-enriched libraries were sequenced on one or two lanes of an Illumina GAII or Illumina HiSeq instrument.

Whole Exome Capture Library Construction—(Multiplexed Procedure)

Over the course of this sequencing effort the Illumina sequencing yields increased enough such that this project and others utilized sample indexing and multiplexing for whole exome sequencing. Similar to the above library process, Applicants followed the procedure described in (39), adapted for production-scale exome capture library construction. Exome targets were generated based on the same genes as above and DNA oligonucleotides were amplified as described above. Genomic DNA from primary tumor and matched blood normal was sheared and ligated to Illumina sequencing adapters including 8 bp indexes. Adaptor ligated DNA ("pond") was then size-selected for lengths between 200-350 bp and hybridized with an excess of bait in solution phase, as described previously (39, 40). The "catch" was pulled down by streptavidin beads and eluted as described above.

Barcoded exon capture libraries were then pooled into batches of 96 samples and sequenced on Illumina HiSeq instrument (76 bp paired-end reads)(39) such that each sample received approximately 0.77 lane of sequencing capacity. The 8 bp index was read by the instrument at the beginning of read 2 and used to distribute sequencing reads to sample in the downstream data aggregation pipeline.

The mean coverage achieved across all exome samples in the data set was 149× in the tumors and 152× in the normals.

Massively Parallel Sequencing

Sequencing libraries were quantified using a SYBR Green qPCR protocol with specific probes complementary to adapter sequence. The qPCR assay measures the quantity of fragments, properly "adapter-ligated", that are appropriate for sequencing. Based on the qPCR quantification, libraries were normalized to 2 nM and then denatured using 0.1 N NaOH. Cluster amplification of denatured templates was performed according to manufacturer's protocol (Illumina) using V2 Chemistry and V2 Flowcells (1.4 mm channel width). SYBR Green dye was added to all flowcell lanes to provide a quality control checkpoint after cluster amplification and to ensure optimal cluster densities on the flowcells.

Paired-end sequencing (2×101 bp for WGS and 2×76 bp for WE) was carried out using Genome Analyzer II or HiSeq sequencing instruments; the resulting data was analyzed with the current Illumina pipeline. Standard quality control metrics—including error rates, % passing filter reads, and total Gb produced—were used to characterize process performance prior to downstream analysis. The Illumina pipeline generates data files (BAM files) that contain the reads together with quality parameters.

Example 3

Sequence Data Processing

Massively parallel sequencing data were processed using two consecutive pipelines. The sequencing data processing pipeline, called "Picard", developed by the Sequencing Platform at the Broad Institute, starts with the reads and qualities produced by the Illumina software for all lanes and libraries generated for a single sample (either tumor or normal) and produces, at the end of the pipeline, a single BAM file (available as a pdf file titled SAM1 on the website of samtools at a sourceforge dot net extension) representing the sample. The final BAM file stores all reads with well-calibrated qualities together with their alignments to the genome (only for reads that were successfully aligned).

The Broad Cancer Genome Analysis pipeline, also known as "Firehose", starts with the BAM files for the tumor and matched normal samples and performs various analyses, including quality control, local realignment, mutation calling, small insertion and deletion identification, rearrangement detection, coverage calculations and others (see details below).

Several of the tools used in these pipelines were developed jointly by the Broad Institute Sequencing Platform, Medical and Population Genetics Program and the Cancer Program. Additional details regarding parts of the pipeline focused on germline events (typically employed for medical and population genetics studies) are described elsewhere (41).

The Sequencing Data-Processing Pipeline ("Picard Pipeline")

Applicants generated a BAM file for each sample using the sequencing data processing pipeline known as "Picard" (see the website of picard at a sourceforge dot net extension). Picard consists of four steps, described in detail in (42), but with the following modifications in the "Alignment to the genome" step: Alignment was performed using BWA (43) (see the website of bio-bwa at a sourceforge dot net extension) to the NCBI Human Reference Genome GRCh37.

The reads in the BAM file were sorted according to their chromosomal position. Unaligned reads were also stored in the BAM file such that all reads that passed the Illumina quality filter (PF reads) were kept in the BAM.

BAM files produced by the Picard pipeline are available in dbGaP under accession # phs000370.v1.p1. Applicants have made available 4 files representing 2 WGS tumor/normal pairs and an additional 184 files representing 92 WE tumor/normal pairs.

The Cancer Genome Analysis Pipeline ("Firehose")

The Cancer Genome Analysis pipeline consists of a set of tools for analyzing massively parallel sequencing data representing tumor DNA samples and their matched normal DNA samples. Firehose is a pipeline infrastructure that manages the input files, analysis tools and the output files; and keeps track of data file locations, analysis "jobs" awaiting execution, priority of analytical tasks, and analyses in progress. The pipeline also coordinates versioning and logging of the specific analytical parameters that generated a given result. Firehose uses GenePattern (44) as its execution engine, which executes pipelines and modules based on specific parameters and inputs files specified by Firehose. The pipeline contains the following steps (described in detail in (42)):

Quality Control.

Figure 7:
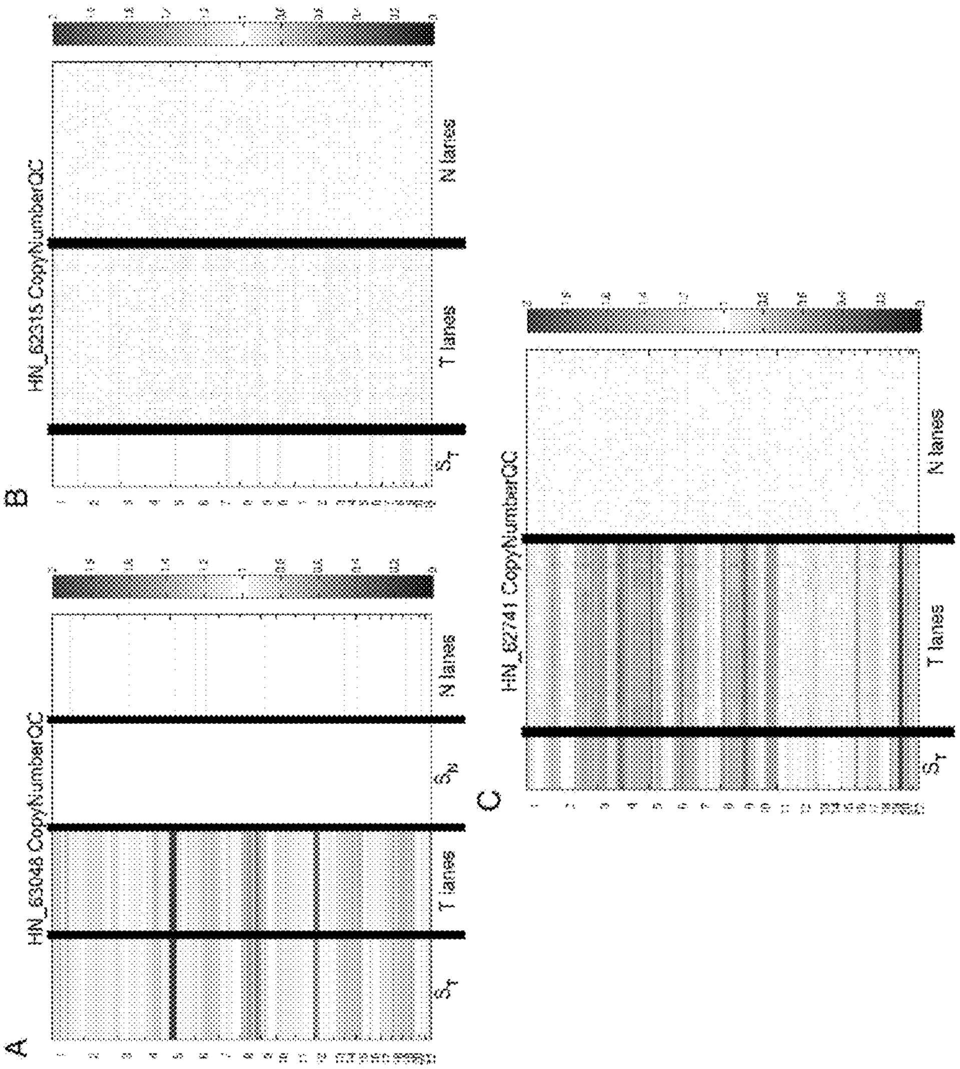
FIG. 7 shows the Quality Control for Stromal Admixture. Sequencing results and SNP array-based copy number data (where available) were assessed in tumor/normal pairs for evidence of copy number changes. Red indicates copy number gain, blue indicates copy number loss. The Y-axis represents chromosome location. ST: copy number inferred from SNP array hybridization from tumor DNA. T lanes: copy number inferred from exome sequencing coverage from tumor DNA. S N: copy number inferred from SNP array hybridization from matched non-tumor DNA. N lanes: copy number inferred from exome sequencing coverage from matched non-tumor DNA. A. Example of a tumor/normal pair that was included in final analysis. Recurrent copy number changes are visible in the tumor DNA, which are absent in the non-tumor DNA. B. Example of a tumor/normal pair excluded from final analysis as a consequence of high levels of stromal admixture. This sample shows a lack of copy number changes in tumor DNA, measured by both SNP arrays and whole exome sequencing. Each column in T lanes and N lanes corresponds to barcoded sequencing data obtained from a different sequencing lane. C. Example of a barcoded sample passing copy-number QC.

Applicants ensured that all data matched their corresponding patient and that there were no mix-ups between tumor and normal data for the same individual. When available, DNA copy-number profiles as well as genotypic information collected from SNP arrays were also included in Firehose. Genotypes derived from the sequencing data and/or SNP arrays were compared between samples from a same individual (tumor/normal) to ensure identity. Genotypes from the SNP arrays also allowed estimating low-levels of cross-contamination between samples from different individuals. By studying the copy number profile of the tumor lanes, Applicants were able to detect samples with various levels of DNA copy-number alterations or a noisy coverage (FIG. 7).

Local Realignment.

Sequence reads corresponding to genomic regions that may harbor small insertions or deletions (indels) were jointly realigned to improve detection of indels and to decrease the number of false positive single nucleotide variations caused by misaligned reads, particularly at the 3' end (41). In order to improve the efficiency of this step, Applicants performed a joint local-realignment of all samples from a same individual ("co-cleaning"). Briefly, all sites potentially harboring small insertions or deletions in either the tumor or the matched normal were realigned in all samples.

Identification of Somatic Single Nucleotide Variations (SSNVs).

Candidate SSNVs were detected using a statistical analysis of the bases and qualities in the tumor and normal BAMs that mapped to the genomic locus being examined. For WGS data Applicants interrogated every position along the genome, and for WE data, Applicants searched for mutations in the neighborhood of the targeted exons (where the majority of reads are located). Applicants also indicated for every analyzed base whether it was sufficiently covered for confident identification of point mutations (42). In brief, the SSNV detection consists of three steps:

(i) Preprocessing of the aligned reads in the tumor and normal sequencing data. In this step Applicants ignore reads with too many mismatches or very low quality scores since they are likely to introduce artifacts.

(ii) A statistical analysis that identifies sites that are likely to carry somatic mutations with high confidence. The statistical analysis predicts a somatic mutation by using two Bayesian classifiers—the first aims to detect whether the tumor is non-reference at a given site and, for those sites that are found as non-reference, the second classifier makes sure the normal does not carry the variant allele. In practice the classification is performed by calculating a LOD score (log odds) and comparing it to a cutoff determined by the log ratio of prior probabilities of the considered events. For the tumors Applicants calculate $$LODT = \log 10 \frac{P(\text{observed data in tumor} \mid \text{site is mutated})}{P(\text{observed data in tumor} \mid \text{site is reference})}$$

and for the normal $$LODN = \log 10 \frac{P(\text{observed data in normal} \mid \text{site is reference})}{P(\text{observed data in normal} \mid \text{site is mutated})}$$

Thresholds were chosen for each statistic such that Applicants' false positive rate is sufficiently low.

(iii) Post-processing of candidate somatic mutations to eliminate artifacts of next-generation sequencing, short read alignment and hybrid capture. For example, sequence context can cause hallucinated alternate alleles but often only in a single direction. Therefore, Applicants test that the alternate alleles supporting the mutations are observed in both directions.

Identification of Somatic Small Insertions and Deletions (Indels).

Indels were detected by first identifying putative events within the tumor BAM file (with high sensitivity but also a high false positive rate). Afterwards, noisy events and potential germline events were filtered out using the corresponding normal data (45).

Identification of Inter-Chromosomal and Intra-Chromosomal Structural Rearrangements.

Candidate rearrangements were identified as groups of paired-end reads which connected genomic regions with an unexpected orientation and/or distance on the same chromosome or from different chromosomes (46). Next, Applicants applied filters to remove germline and false positive calls based on mapping quality, existence of discordant pairs in the vicinity and variability of the starting point of the supporting reads. The validation rate of rearrangements called by these criteria and with at least 4 supporting read pairs is >80% (46).

Determination of Mutation Rates.

Applicants calculated base mutation rates using both the mutations detected (SSNVs and indels) and the coverage statistics. Mutations (and bases) were further partitioned into mutation categories such as mutations in (i) Cs in CpG dinucleotides mutated to a T (transition), (ii) Cs in CpG dinucleotides mutated to a C or an A (transversion), (iii) other Cs mutated to an A (non-CpG G-)T transversion), (iv) other Cs mutated to T or G (and following or not following a T) (v) As or Ts and (vi) mutations that disrupt the genes such as frameshift indels and non sense mutations.

Identification of Significantly Mutated Genes.

Genes that harbored more mutations than expected by chance were identified by comparing the observed number of mutations (from each category described above) across the samples to the expected number based on the background mutation rates and the covered bases in all samples (42). Covered bases were defined as bases with more than 14 reads in the tumor and 8 reads in the normal. For each gene, Applicants calculated the probability of seeing the observed constellation of mutations or a more extreme one, given the background mutation rates calculated across the dataset. This is done by convoluting a set of binomial distributions, as described previously (47). This p-value is then adjusted for multiple hypotheses according to the Benjamini Hochberg procedure for controlling False Discovery Rate (FDR) (48), obtaining a q-value. Two investigators (N.S. and A.D.T.) manually reviewed all mutations and indels identified by this automated methodology by viewing the aligned reads corresponding to each individual mutation call using the Integrated Genomic Viewer (49).

Mutation annotation.

Point mutations and indels identified as described above were also annotated using publicly available databases. In brief, a local database of human genome build h g19-derived annotations compiled from multiple different public resources was used to map genomic variants to specific genes, transcripts, and other relevant features. The same data was used to predict the functional consequence (if any) a variant might have on the corresponding protein product. The set of 73,671 reference transcripts used were derived from transcripts from the UCSC Genome Browser's UCSC Genes track (50) and microRNAs from miRBase release 15 (51) as provided in the TCGA General Annotation Files (GAF) 1.0 library (see the website for wiki on the NCI/NIH website under the section Display, subsection TCGA with the combination entry RNASeq+Data+Format+Specification). Variants were also annotated with data from the following resources: dbSNP build 132 (52), UCSC Genome Browser's ORegAnno track (50, 53), UniProt release 2011_03 (54), PolyPhen-2 (55), COSMIC v51 (56), significant results from published MutSig analyses (38, 42, 45, 46, 57) significant regions from Tumorscape (58) and cancer cell line genotypes from the Broad-Novartis Cancer Cell Line Encyclopedia (see the website of the Broad Institute under the section Cancer Cell Line Encyclopedia (ccle)).

Exclusion of Sequencing Data from Downstream Analysis

Tumor samples (18 in total) for which the copy-number profile showed no evidence of chromosomal copy number alterations (FIG. 7B)—suggesting high stromal contamination, were subjected to additional analyses. In particular, all such samples coincidentally had abnormally low numbers of mutations and a maximal allelic fraction across all mutations that was <~20%, consistent with extensive stromal admixture. The maximal allelic fraction in sample i was defined as number of alternate reads in tumor i,j $AFmax_i$=max, where N is the number of total number of reads in tumor i,j j=1, . . . , N mutations in sample i, with total number of reads in $tumor_i$, 20. Comparison of mutation rates and maximal allelic fraction of the mutations found in each sample (at sites with more than 20 reads in the tumor) allowed us to determine the correlation between both values (r=0.74, p<1e-15, Pearson Correlation). A threshold of 10 mutations per sample (-4e-7 mutations/Mb) corresponded on average to a maximal allelic fraction that is less than 20% (<40% purity) and was chosen as a sample exclusion criteria.

Example 4

Functional Classification of Significantly Mutated Genes

To identify functional gene annotations enriched for significantly mutated genes in HNSCC, Applicants used the Ingenuity Pathway Analysis software (Ingenuity Systems). Applicants uploaded the gene symbols for 76 genes that had a q-value of less than 0.25 (FIG. 22A-B) and queried for enrichment of physiological system development and function networks. The results are presented in FIG. 23 and show the different biological processes enriched in the list by order of significance, corrected for multiple hypothesis testing by the method of Benjamini-Hochberg (48).

Example 5

Experimental Validation of Somatic Mutations by Mass Spectrometric Genotyping To assess the specificity of Applicants' algorithm for calling somatic mutations in the HNSCC data set, Applicants obtained independent validation data for 321 candidate mutations using mass spectrometric genotyping (Sequenom) of tumor and normal DNA. The genomic DNA used for these experiments was first subjected to whole genome amplification by a strand displacement protocol, as described previously (59). Mutations interrogated by mass spectrometric genotyping included 59 candidate protein-coding mutations in genes significantly mutated in the Illumina data with q-value<0.1. The genotyping data confirmed 89.7% of mutations found in the Illumina data; however, Sequenom false negative results may account for some of the discordances. One mechanism by which this may arise is through loss of mutant alleles during whole genome amplification. Additionally, Applicants have observed that mass spectrometric genotyping may exhibit an elevated false negative rate for mutations with an allelic fraction<20% (52). Using the Clopper-Pearson method to calculate 95% confidence intervals, Applicants inferred that Applicants' overall accuracy rates for mutations calls were 89.7% (CI: 86%-93%) and 95.7% (CI: 92-98%) for mutations whose allelic fraction was >20% of total DNA.

Example 6

Mutation Rates of Previously Treated HNSCC Tumors

Mutation rates and G-) T transversion frequencies for previously treated HNSCC tumors did not differ from previously untreated primary tumors (p=0.79 and p=0.20, respectively). The exclusion of these tumors from the dataset did not influence significantly the reported results.

Example 7

Sinonasal Squamous Cell Carcinoma

Applicants included in Applicants' analysis two samples of sinonasal squamous cell carcinoma. There is some evidence that this disease process may be associated with distinct risk factors from squamous cell carcinoma occurring elsewhere in the upper aerodigestive tract (63). However, the molecular characteristics of these samples argue for a common pathogenesis, despite their sinonasal origin. One of the tumors is HPV-positive and harbors mutations in NOTCH3 and SYNE1; the other tumor harbors a TP53 mutation. These features are characteristic of the other HNSCC tumors included in this invention.

Example 8

Tumors with Elevated Point Mutation Rates

The two HNSCC tumors with the highest mutation rates occurred in non-smokers and had complete clinical responses to surgery followed by adjuvant chemoradiotherapy (not shown). They contained heterozygous mutations in one or more DNA repair genes, including both FANCM and APLF. FANCM is a member of the Fanconi anemia complementation group; its protein product is thought to mediate DNA repair at stalled replication forks (64), and individuals with Fanconi anemia have 500-fold increased risk of developing HNSCC (65). APLF is involved in the cellular response to single- and double-stranded DNA breaks (66).

REFERENCES

1. J. Ferlay et al., Estimates of worldwide burden of cancer in 2008: GLOBOCAN 2008. *Int J Cancer* 127, 2893 (Dec. 15, 2010).
2. A. Argiris, M. V. Karamouzis, D. Raben, R. L. Ferris, Head and neck cancer. *Lancet* 371, 1695 (May 17, 2008).
3. S. Gupta, W. Kong, Y. Peng, Q. Miao, W. J. Mackillop, Temporal trends in the incidence and survival of cancers of the upper aerodigestive tract in Ontario and the United States. *Int J Cancer* 125, 2159 (Nov. 1, 2009).
4. C. R. Leemans, B. J. Braakhuis, R. H. Brakenhoff, The molecular biology of head and neck cancer. *Nat Rev Cancer* 11, 9 (January, 2011).
5. W. Lee et al., The mutation spectrum revealed by paired genome sequences from a lung cancer patient. *Nature* 465, 473 (May 27, 2010).
6. E. D. Pleasance et al., A small-cell lung cancer genome with complex signatures of tobacco exposure. *Nature* 463, 184 (Jan. 14, 2010).

7. M. A. Chapman et al., Initial genome sequencing and analysis of multiple myeloma. *Nature* 471, 467 (Mar. 24, 2011).
8. The Cancer Genome Atlas Research Network, Integrated Genomic Analyses of Ovarian Carcinoma *Nature*, (2011).
9. U. Koch, F. Radtke, Notch signaling in solid tumors. *Current topics in developmental biology* 92, 411 (2010).
10. X. S. Puente et al., Whole-genome sequencing identifies recurrent mutations in chronic lymphocytic leukaemia. *Nature*, (Jun. 5, 2011).
11. A. P. Weng et al., Activating mutations of NOTCH1 in human T cell acute lymphoblastic leukemia. *Science* 306, 269 (Oct. 8, 2004).
12. S. Y. Lee et al., Gain-of-function mutations and copy number increases of Notch2 in diffuse large B-cell lymphoma. *Cancer Sci* 100, 920 (May, 2009).
13. A. Klinakis et al., A novel tumour-suppressor function for the Notch pathway in myeloid leukaemia. *Nature* 473, 230 (May 12, 2011).
14. R. A. Kovall, S. C. Blacklow, Mechanistic insights into Notch receptor signaling from structural and biochemical studies. *Curr Top Dev Biol* 92, 31 (2010).
15. B. C. Nguyen et al., Cross-regulation between Notch and p63 in keratinocyte commitment to differentiation. *Genes Dev* 20, 1028 (Apr. 15, 2006).
16. R. Okuyama et al., p53 homologue, p51/p63, maintains the immaturity of keratinocyte stem cells by inhibiting NOTCH1 activity. *Oncogene* 26, 4478 (Jul. 5, 2007).
17. X. Su et al., Rescue of key features of the p63-null epithelial phenotype by inactivation of Ink4a and Arf. *EMBO J.* 28, 1904 (Jul. 8, 2009).
18. F. Moretti et al., A regulatory feedback loop involving p63 and IRF6 links the pathogenesis of 2 genetically different human ectodermal dysplasias. *J Clin Invest* 120, 1570 (May 3, 2010).
19. T. Yugawa et al., DeltaNp63alpha repression of the NOTCH1 gene supports the proliferative capacity of normal human keratinocytes and cervical cancer cells. *Cancer Res* 70, 4034 (May 15, 2010).
20. C. Blanpain, E. Fuchs, Epidermal homeostasis: a balancing act of stem cells in the skin. *Nat Rev Mol Cell Biol* 10, 207 (March, 2009).
21. M. Chidgey et al., Mice lacking desmocollin 1 show epidermal fragility accompanied by barrier defects and abnormal differentiation. *J Cell Biol* 155, 821 (Nov. 26, 2001).
22. A. Dumortier et al., Atopic dermatitis-like disease and associated lethal myeloproliferative disorder arise from loss of Notch signaling in the murine skin. *PLoS One* 5, e9258 (2010).
23. E. Ezhkova et al., EZH1 and EZH2 cogovern histone H3K27 trimethylation and are essential for hair follicle homeostasis and wound repair. *Genes Dev* 25, 485 (Mar. 1, 2011).
24. M. Nicolas et al., NOTCH1 functions as a tumor suppressor in mouse skin. *Nat Genet.* 33, 416 (March, 2003).
25. C. L. Tinkle, T. Lechler, H. A. Pasolli, E. Fuchs, Conditional targeting of E-cadherin in skin: insights into hyperproliferative and degenerative responses. *Proc Natl Acad Sci USA* 101, 552 (Jan. 13, 2004).
26. Online Mendelian Inheritance in Man (OMIM™). (McKusick-Nathans Institute of Genetic Medicine, Johns Hopkins University (Baltimore, Md.) and National Center for Biotechnology Information, National Library of Medicine (Bethesda, Md.), 2011).
27. C. L. Tu, W. Chang, Z. Xie, D. D. Bikle, Inactivation of the calcium sensing receptor inhibits E-cadherin-mediated cell-cell adhesion and calcium-induced differentiation in human epidermal keratinocytes. *J Biol Chem* 283, 3519 (Feb. 8, 2008).
28. Y. Luke et al., Nesprin-2 Giant (NUANCE) maintains nuclear envelope architecture and composition in skin. *J Cell Sci* 121, 1887 (Jun. 1, 2008).
29. S. E. Williams, S. Beronja, H. A. Pasolli, E. Fuchs, Asymmetric cell divisions promote Notch-dependent epidermal differentiation. *Nature* 470, 353 (Feb. 17, 2011).
30. K. Fujimoto et al., Piccolo, a Ca2+ sensor in pancreatic beta-cells. Involvement of cAMP-GEFII.Rim2. Piccolo complex in cAMP-dependent exocytosis. *J Biol Chem* 277, 50497 (Dec. 27, 2002).
31. A. D. Kostic et al., PathSeq: software to identify or discover microbes by deep sequencing of human tissue. *Nat Biotechnol* 29, 393 (May, 2011).
32. W. H. Westra et al., Inverse relationship between human papillomavirus-16 infection and disruptive p53 gene mutations in squamous cell carcinoma of the head and neck. *Clin Cancer Res* 14, 366 (Jan. 15, 2008).
33. A. Extance, Alzheimer's failure raises questions about disease-modifying strategies. *Nat Rev Drug Discov* 9, 749 (October, 2010).
34. L. A. Garraway, W. R. Sellers, Lineage dependency and lineage-survival oncogenes in human cancer. *Nat Rev Cancer* 6, 593 (August, 2006).
35. W. Amin et al., An informatics supported web-based data annotation and query tool to expedite translational research for head and neck malignancies. *BMC Cancer* 9, 396 (2009).
36. A. D. Kostic et al., PathSeq: software to identify or discover microbes by deep sequencing of human tissue. *Nat Biotechnol* 29, 393 (May, 2011).
37. M. Moberg, I. Gustaysson, U. Gyllensten, Real-time PCR-based system for simultaneous quantification of human papillomavirus types associated with high risk of cervical cancer. *J Clin Microbiol* 41, 3221 (July, 2003).
38. The Cancer Genome Atlas Research Network, Comprehensive genomic characterization defines human glioblastoma genes and core pathways. *Nature* 455, 1061 (Oct. 23, 2008).
39. A. Gnirke et al., Solution hybrid selection with ultra-long oligonucleotides for massively parallel targeted sequencing. *Nat Biotechnol* 27, 182 (February, 2009).
40. S. Fisher et al., A scalable, fully automated process for construction of sequence-ready human exome targeted capture libraries. *Genome biology* 12, R1 (Jan. 4, 2011).
41. M. A. Depristo et al., A framework for variation discovery and genotyping using next-generation DNA sequencing data. Nat Genet. 43, 491 (May, 2011).
42. M. A. Chapman et al., Initial genome sequencing and analysis of multiple myeloma. *Nature* 471, 467 (Mar. 24, 2011).
43. H. L1, R. Durbin, Fast and accurate long-read alignment with Burrows-Wheeler transform. *Bioinformatics* 26, 589 (Mar. 1, 2010).
44. M. Reich et al., GenePattern 2.0. *Nat Genet.* 38, 500 (May, 2006).
45. The Cancer Genome Atlas Research Network, Integrated Genomic Analyses of Ovarian Carcinoma *Nature* 474, 541 (June, 2011).
46. M. F. Berger et al., The genomic complexity of primary human prostate cancer. *Nature* 470, 214 (Feb. 10, 2011).
47. G. Getz et al., Comment on "The consensus coding sequences of human breast and colorectal cancers". *Science* 317, 1500 (Sep. 14, 2007).

48. Y. Benjamini, Y. Hochberg, Controlling the false discovery rate: a practical and powerful approach to multiple testing. *Journal of the Royal Statistical Society* Series B (Methodological) 57 (1), 11 (1995).
49. J. T. Robinson et al., Integrative genomics viewer. *Nat Biotechnol* 29, 24 (January, 2011).
50. P. A. Fujita et al., The UCSC Genome Browser database: update 2011. *Nucleic Acids Res* 39, D876 (January, 2011).
51. A. Kozomara, S. Griffiths-Jones, miRBase: integrating microRNA annotation and deep-sequencing data. *Nucleic acids research* 39, D152 (January, 2011).
52. S. T. Sherry et al., dbSNP: the NCBI database of genetic variation. *Nucleic Acids Res* 29, 308 (Jan. 1, 2001).
53. O. L. Griffith et al., ORegAnno: an open-access community-driven resource for regulatory annotation. *Nucleic Acids Res* 36, D107 (January, 2008).
54. UniProt Consortium, Ongoing and future developments at the Universal Protein Resource. *Nucleic Acids Res* 39, D214 (January, 2011).
55.1. A. Adzhubei et al., A method and server for predicting damaging missense mutations. *Nat Methods* 7, 248 (April, 2010).
56. S. A. Forbes et al., COSMIC: mining complete cancer genomes in the Catalogue of Somatic Mutations in Cancer. *Nucleic Acids Res* 39, D945 (January, 2011).
57. L. Ding et al., Somatic mutations affect key pathways in lung adenocarcinoma. *Nature* 455, 1069 (Oct. 23, 2008).
58. R. Beroukhim et al., The landscape of somatic copy-number alteration across human cancers. *Nature* 463, 899 (Feb. 18, 2010).
59. J. G. Paez et al., Genome coverage and sequence fidelity of phi29 polymerase-based multiple strand displacement whole genome amplification. *Nucleic acids research* 32, e71 (2004).
60. A. A. Mills, p63: oncogene or tumor suppressor? *Curr Opin Genet Dev* 16, 38 (February, 2006).
61. A. J. Wong et al., Structural alterations of the epidermal growth factor receptor gene in human gliomas. *Proceedings of the National Academy of Sciences of the United States of America* 89, 2965 (Apr. 1, 1992).
62. J. C. Sok et al., Mutant epidermal growth factor receptor (EGFRvIII) contributes to head and neck cancer growth and resistance to EGFR targeting. *Clin Cancer Res* 12, 5064 (Sep. 1, 2006).
63. F. Lopez et al., Genomic profiling of sinonasal squamous cell carcinoma. *Head & neck* 33, 145 (February, 2011).
64. Y. Kee, A. D. D'Andrea, Expanded roles of the Fanconi anemia pathway in preserving genomic stability. *Genes Dev* 24, 1680 (Aug. 15, 2010).
65. D. I. Kutler et al., High incidence of head and neck squamous cell carcinoma in patients with Fanconi anemia. *Arch Otolaryngol Head Neck Surg* 129, 106 (January, 2003).
66. Ahel et al., Poly(ADP-ribose)-binding zinc finger motifs in DNA repair/checkpoint proteins. *Nature* 451, 81 (Jan. 3, 2008).

Example 9

Development of Mammalian TALE Transcriptional Repressors

Figure 18:
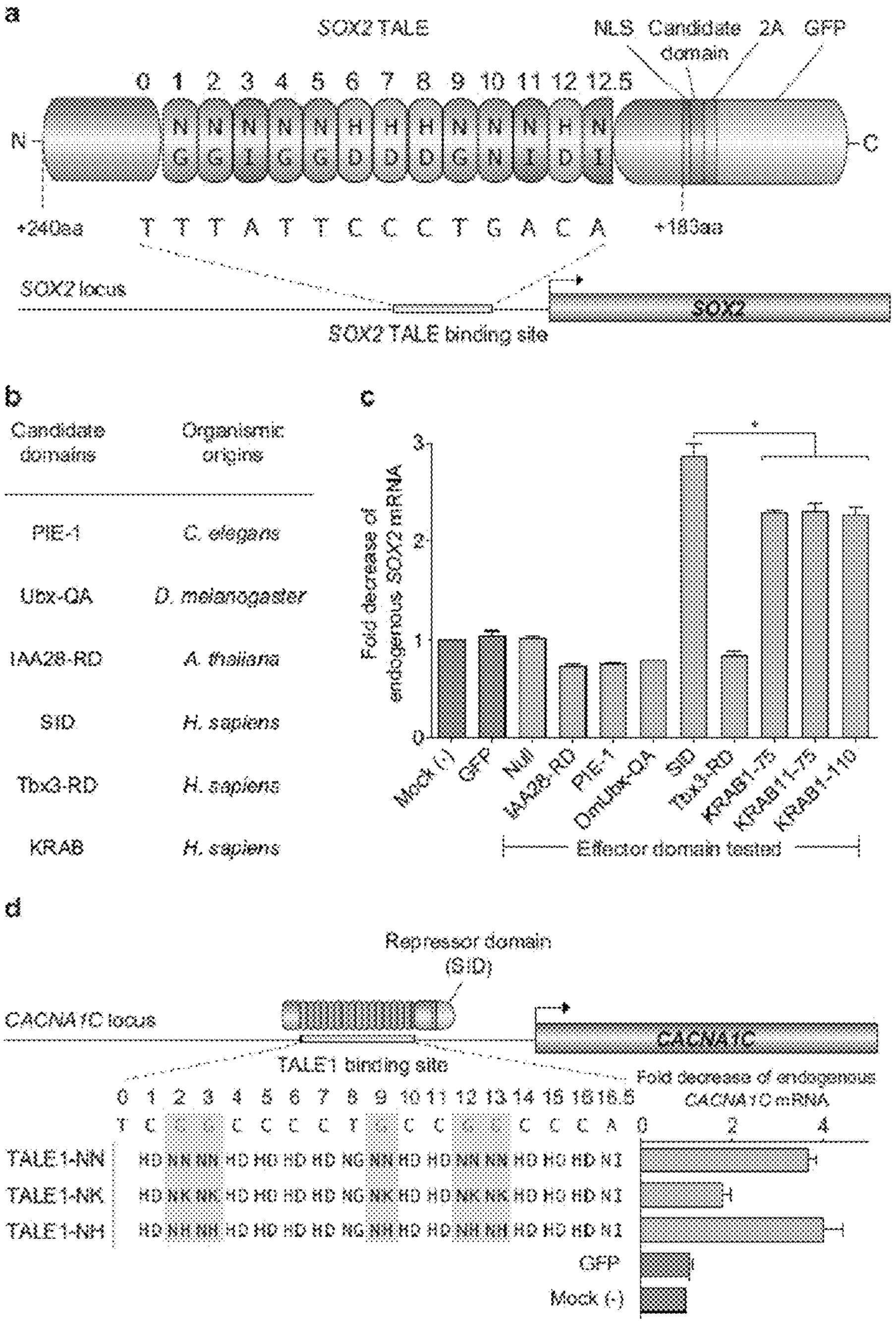
FIG. 18 shows the development of a TALE transcriptional repressor architecture. (a) Design of SOX2 TALE for TALE repressor screening. A TALE targeting a 14 bp sequence within the SOX2 locus of the human genome was synthesized. Figure discloses SEQ ID NO: 271. (b) List of all repressors screened and their host origin (left). Eight different candidate repressor domains were fused to the C-term of the SOX2 TALE. (c) The fold decrease of endogenous SOX2 mRNA is measured using qRTPCR by dividing the SOX2 mRNA levels in mock transfected cells by SOX2 mRNA levels in cells transfected with each candidate TALE repressor. (d) Transcriptional repression of endogenous CACNA1C. TALEs using NN, NK, and NH as the G-targeting RVD were constructed to target a 18 bp target site within the human CACNA1C locus. Each TALE is fused to the SID repression domain. NLS, nuclear localization signal; KRAB, Krüppel-associated box; SID, mSin interaction domain. All results are collected from three independent experiments in HEK 293FT cells. Error bars indicate s.e.m.; n=3. * $p<0.05$, Student's t test. Figure discloses SEQ ID NO: 272.

Applicants developed mammalian TALE repressor architectures to enable researchers to suppress transcription of endogenous genes. TALE repressors have the potential to suppress the expression of genes as well as non-coding transcripts such as microRNAs, rendering them a highly desirable tool for testing the causal role of specific genetic elements. In order to identify a suitable repression domain for use with TALEs in mammalian cells, a TALE targeting the promoter of the human SOX2 gene was used to evaluate the transcriptional repression activity of a collection of candidate repression domains (FIG. 18*a*). Repression domains across a range of eukaryotic host species were selected to increase the chance of finding a potent synthetic repressor, including the PIE-1 repression domain (PIE-1) (2) from *Caenorhabditis elegans*, the QA domain within the Ubx gene (Ubx-QA) (3) from *Drosophila melanogaster*, the IAA28 repression domain (IAA28-RD)(4) from *Arabidopsis thaliana*, the mSin interaction domain (SID) (1), Tbx3 repression domain (Tbx3-RD), and the Krüppel-associated box (KRAB) (5) repression domain from *Homo Sapiens*. Since different truncations of KRAB have been known to exhibit varying levels of transcriptional repression (5), three different truncations of KRAB were tested (FIG. 18*c*). These candidate TALE repressors were expressed in HEK 293FTcells and it was found that TALEs carrying two widely used mammalian transcriptional repression domains, the SID (1) and KRAB (5) domains, were able to repress endogenous SOX2 expression, while the other domains had little effect on transcriptional activity (FIG. 18*c*). To control for potential perturbation of SOX2 transcription due to TALE binding, expression of the SOX2-targeting TALE DNA binding domain alone without any effector domain had no effect (similar to mock or expression of GFP) on the transcriptional activity of SOX2 (FIG. 18*c*, Null condition). Since the SID domain was able to achieve 26% more transcriptional repression of the endogenous SOX2 locus than the KRAB domain (FIG. 18*c*), it was decided to use the SID domain for subsequent studies.

To further test the effectiveness of the SID repressor domain for down regulating endogenous transcription, SID was combined with CACNA1C-target TALEs from the previous experiment (FIG. 18*d*). Using qRT-PCR, it was found that replacement of the VP64 domain on CACNA1C-targeting TALEs with SID was able to repress CACNA1C transcription. The NH-containing TALE repressor was able to achieve a similar level of transcriptional repression as the NN-containing TALE (~4 fold repression), while the TALE repressor using NK was significantly less active (~2 fold repression) (FIG. 18*d*). These data demonstrate that SID is indeed a suitable repression domain, while also further supporting NH as a more suitable G-targeting RVD than NK.

TALEs can be easily customized to recognize specific sequences on the endogenous genome. Here, a series of screens were conducted to address two important limitations of the TALE toolbox. Together, the identification of a more stringent G-specific RVD with uncompromised activity strength as well as a robust TALE repressor architecture further expands the utility of TALEs for probing mammalian transcription and genome function.

Figure 19:
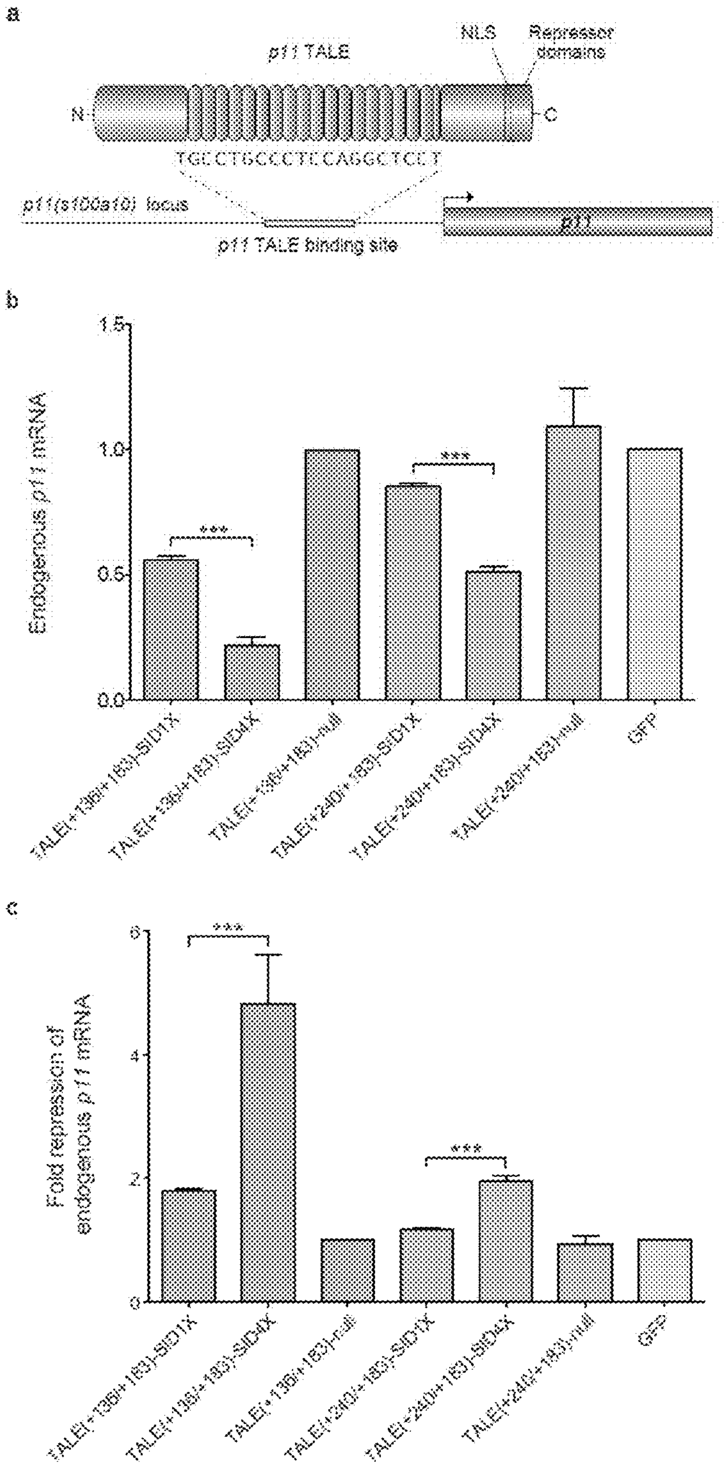
FIG. 19 shows the optimization of TALE transcriptional repressor architecture using SID and SID4X. (a) Design of p11 TALE for testing of TALE repressor architecture. A TALE targeting a 20 bp sequence (p11 TALE binding site) within the p11 (s100a10) locus of the mouse (*Mus musculus*) genome was synthesized. Figure discloses SEQ ID NO: 273. (b) Transcriptional repression of endogenous mouse p11 mRNA. TALEs targeting the mouse p11 locus harboring two different truncations of the wild type TALE architecture were fused to different repressor domains as indicated on the x-axis. The value in the bracket indicate the number of amino acids at the N- and C-termini of the TALE DNA binding domain flanking the DNA binding repeats, followed by the repressor domain used in the construct. The endogenous p11 mRNA levels were measured using qRT-PCR and normalized to the level in the negative control cells transfected with a GFP-encoding construct. (c) Fold of transcriptional repression of endogenous mouse p11. The fold decrease of endogenous p11 mRNA is measured using qRT-PCR through dividing the p11 mRNA levels in cells transfected with a negative control GFP construct by p11 mRNA levels in cells transfected with each candidate TALE repressors. The labeling of the constructs along the x-axis is the same as previous panel. NLS, nuclear localization signal; SID, mSin interaction domain; SID4X, an optimized four-time tandem repeats of SID domain linked by short peptide linkers. All results are collected from three independent experiments in Neuro2A cells. Error bars indicate s.e.m.

After identifying SID (mSin interaction domain) as a robust novel repressor domain to be used with TALEs, more active repression domain architecture based on SID domain for use with TALEs in mammalian cells were further designed and verified. This domain is called SID4X, which is a tandem repeat of four SID domains linked by short peptide linkers. For testing different TALE repressor architectures, a TALE targeting the promoter of the mouse (*Mus musculus*) p11 (s100a10) gene was used to evaluate the transcriptional repression activity of a series of candidate TALE repressor architectures (FIG. 19*a*). Since different truncations of TALE are known to exhibit varying levels of transcriptional activation activity, two different truncations of TALE fused to SID or SID4X domain were tested, one version with 136 and 183 amino acids at N- and C-termini flanking the DNA binding tandem repeats, with another one retaining 240 and 183 amino acids at N- and C-termini (FIG. 19*b, c*). The candidate TALE repressors were expressed in mouse Neuro2A cells and it was found that TALEs carrying both SID and SID4X domains were able to repress endogenous p11 expression up to 4.8 folds, while the GFP-encoding negative control construct had no effect on transcriptional of target gene (FIG. 19*b, c*). To control for potential perturbation of p11 transcription due to TALE binding, expression of the p11-targeting TALE DNA binding domain (with the same N- and C-termini truncations as the tested constructs) without any effector domain had no effect on the transcriptional activity of endogenous p11 (FIG. 19*b, c*, null constructs).

Because the constructs harboring SID4X domain were able to achieve 167% and 66% more transcriptional repression of the endogenous p11 locus than the SID domain depending on the truncations of TALE DNA binding domain (FIG. 19*c*), it was concluded that a truncated TALE DNA binding domain, bearing 136 and 183 amino acids at N- and C-termini respectively, fused to the SID4X domain is a potent TALE repressor architecture that enables down-regulation of target gene expression and is more active than the previous design employing SID domain. The mSin interaction domain (SID) and SID4X domain were codon optimized for mammalian expression and synthesized with flanking NheI and XbaI restriction sites (Genscript). Truncation variants of the TALE DNA binding domains are PCR amplified and fused to the SID or the SID4X domain using NheI and XbaI restriction sites. To control for any effect on transcription resulting from TALE binding, expression vectors carrying the TALE DNA binding domain alone using PCR cloning were constructed. The coding regions of all constructs were completely verified using Sanger sequencing. A comparison of two different types of TALE architecture is seen in FIG. 20.

REFERENCES

1. Ayer, D. E., Laherty, C. D., Lawrence, Q. A., Armstrong, A. P. & Eisenman, R. N. Mad proteins contain a dominant transcription repression domain. *Mol. Cell. Biol.* 16, 5772-5781 (1996).
2. Batchelder, C. et al. Transcriptional repression by the *Caenorhabditis elegans* germ-line protein PIE-1. *Genes Dev.* 13, 202-212 (1999).
3. Tour, E., Hittinger, C. T. & McGinnis, W. Evolutionarily conserved domains required for activation and repression functions of the *Drosophila* Hox protein Ultrabithorax. *Development* 132, 5271-5281 (2005).
4. Tiwari, S. B., Hagen, G. & Guilfoyle, T. J. Aux/IAA proteins contain a potent transcriptional repression domain. *Plant Cell* 16, 533-543 (2004).
5. Margolin, J. F. et al. Kruppel-associated boxes are potent transcriptional repression domains. *Proc. Natl. Acad. Sci. USA* 91, 4509-4513 (1994).

Example 10

Development of Mammalian TALE Transcriptional Activators and Nucleases

Customized TALEs can be used for a wide variety of genome engineering applications, including transcriptional modulation and genome editing. Here, Applicants describe a toolbox for rapid construction of custom TALE transcription factors (TALE-TFs) and nucleases (TALENs) using a hierarchical ligation procedure. This toolbox facilitates affordable and rapid construction of custom TALE-TFs and TALENs within 1 week and can be easily scaled up to construct TALEs for multiple targets in parallel. Applicants also provide details for testing the activity in mammalian cells of custom TALE-TFs and TALENs using quantitative reverse-transcription PCR and Surveyor nuclease, respectively. The TALE toolbox will enable a broad range of biological applications.

TALEs are natural bacterial effector proteins used by *Xanthomonas* sp. to modulate gene transcription in host plants to facilitate bacterial colonization (7, 8). The central region of the protein contains tandem repeats of 34-aa sequences (termed monomers) that are required for DNA recognition and binding (9, 10, 11, 12) (FIG. 14). Naturally occurring TALEs have been found to have a variable number of monomers, ranging from 1.5 to 33.5 (7). Although the sequence of each monomer is highly conserved, they differ primarily in two positions termed the repeat variable diresidues (RVDs, 12th and 13th positions). Recent reports have found that the identity of these two residues determines the nucleotide-binding specificity of each TALE repeat and that a simple cipher specifies the target base of each RVD (NI=A, HD=C, NG=T, NN=G or A) (1, 2). Thus, each monomer targets one nucleotide and the linear sequence of monomers in a TALE specifies the target DNA sequence in the 5' to 3' orientation. The natural TALE-binding sites within plant genomes always begin with a thymine (1, 2), which is presumably specified by a cryptic signal within the nonrepetitive N terminus of TALEs. The tandem repeat DNA-binding domain always ends with a half-length repeat (0.5 repeat, FIG. 14). Therefore, the length of the DNA sequence being targeted is equal to the number of full repeat monomers plus two.

Applicants have further improved the TALE assembly system with a few optimizations, including maximizing the dissimilarity of ligation adaptors to minimize misligations and combining separate digest and ligation steps into single Golden Gate (13, 14, 15) reactions. Briefly, each nucleotide-specific monomer sequence is amplified with ligation adaptors that uniquely specify the monomer position within the TALE tandem repeats. Once this monomer library is produced, it can conveniently be reused for the assembly of many TALEs. For each TALE desired, the appropriate monomers are first ligated into hexamers, which are then amplified via PCR. Then, a second Golden Gate digestion-ligation with the appropriate TALE cloning backbone (FIG. 14) yields a fully assembled, sequence-specific TALE. The backbone contains a ccdB negative selection cassette flanked by the TALE N and C termini, which is replaced by the tandem repeat DNA-binding domain when the TALE has been successfully constructed. ccdB selects against cells transformed with an empty backbone, thereby yielding clones with tandem repeats inserted (5).

Assemblies of monomeric DNA-binding domains can be inserted into the appropriate TALE-TF or TALEN cloning backbones to construct customized TALE-TFs and TALENs. TALE-TFs are constructed by replacing the natural activation domain within the TALE C terminus with the synthetic transcription activation domain VP64 (3; FIG. 14). By targeting a binding site upstream of the transcription start site, TALE-TFs recruit the transcription complex in a site-specific manner and initiate gene transcription. TALENs are constructed by fusing a C-terminal truncation (+63 aa) of the TALE DNA-binding domain (4) with the nonspecific FokI endonuclease catalytic domain (FIG. 14). The +63-aa C-terminal truncation has also been shown to function as the minimal C terminus sufficient for transcriptional modulation (3). TALENs form dimers through binding to two target sequences separated by ~17 bases. Between the pair of binding sites, the FokI catalytic domains dimerize and function as molecular scissors by introducing double-strand breaks (DSBs; FIG. 14). Normally, DSBs are repaired by the nonhomologous end-joining (16) pathway (NHEJ), resulting in small deletions and functional gene knockout. Alternatively, TALEN-mediated DSBs can stimulate homologous recombination, enabling site-specific insertion of an exogenous donor DNA template (4, 6).

Along with the TALE-TFs being constructed with the VP64 activation domain, other embodiments of the invention relate to TALE polypeptides being constructed with the VP16 and p65 activation domains. A graphical comparison of the effect these different activation domains have on Sox2 mRNA level is provided in FIG. 17.

REFERENCES

1. Boch, J. et al. Breaking the code of DNA binding specificity of TAL-type III effectors. *Science* 326, 1509-1512 (2009).
2. Moscou, M. J. & Bogdanove, A. J. A simple cipher governs DNA recognition by TAL effectors. *Science* 326, 1501 (2009).
3. Zhang, F. et al. Efficient construction of sequence-specific TAL effectors for modulating mammalian transcription. *Nat. Biotechnol.* 29, 149-153 (2011).
4. Miller, J. C. et al. A TALE nuclease architecture for efficient genome editing. *Nat. Biotechnol.* 29, 143-148 (2011).
5. Cermak, T. et al. Efficient design and assembly of custom TALEN and other TAL effector-based constructs for DNA targeting. *Nucleic Acids Res.* 39, e82 (2011).
6. Hockemeyer, D. et al. Genetic engineering of human pluripotent cells using TALE nucleases. *Nat. Biotechnol.* 29, 731-734 (2011).
7. Boch, J. & Bonas, U. *Xanthomonas* AvrBs3 family-type III effectors: discovery and function. *Annu. Rev. Phytopathol.* 48, 419-436 (2010).
8. Bogdanove, A. J., Schornack, S. & Lahaye, T. TAL effectors: finding plant genes for disease and defense. *Curr. Opin. Plant Biol.* 13, 394-401 (2010).
9. Romer, P. et al. Plant pathogen recognition mediated by promoter activation of the pepper Bs3 resistance gene. *Science* 318, 645-648 (2007).
10. Kay, S., Hahn, S., Marois, E., Hause, G. & Bonas, U. A bacterial effector acts as a plant transcription factor and induces a cell size regulator. *Science* 318, 648-651 (2007).
11. Kay, S., Hahn, S., Marois, E., Wieduwild, R. & Bonas, U. Detailed analysis of the DNA recognition motifs of the *Xanthomonas* type III effectors AvrBs3 and AvrBs3Deltarep16. *Plant J.* 59, 859-871 (2009).
12. Romer, P. et al. Recognition of AvrBs3-like proteins is mediated by specific binding to promoters of matching pepper Bs3 alleles. *Plant Physiol.* 150, 1697-1712 (2009).
13. Engler, C., Kandzia, R. & Marillonnet, S. A one pot, one step, precision cloning method with high throughput capability. *PLoS ONE* 3, e3647 (2008).
14. Engler, C., Gruetzner, R., Kandzia, R. & Marillonnet, S. Golden gate shuffling: a one-pot DNA shuffling method based on type IIs restriction enzymes. *PLoS ONE* 4, e5553 (2009).
15. Weber, E., Engler, C., Gruetzner, R., Werner, S. & Marillonnet, S. A modular cloning system for standardized assembly of multigene constructs. *PLoS ONE* 6, e16765 (2011).
16. Huertas, P. DNA resection in eukaryotes: deciding how to fix the break. *Nat. Struct. Mol. Biol.* 17, 11-16 (2010).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of altering expression of a genomic locus of interest in a mammalian cell, comprising contacting the genomic locus with a non-naturally occurring or engineered composition comprising a deoxyribonucleic acid (DNA) binding polypeptide comprising:

(a) a N-terminal capping region (b) a DNA binding domain comprising at least five or more TALE monomers and at least one or more half-monomers specifically ordered to target the genomic locus of interest, and (c) a C-terminal capping region wherein (a), (b) and (c) are arranged in a predetermined N-terminus to C-terminus orientation, wherein the polypeptide includes at least one or more effector domains, and wherein the polypeptide is encoded by and translated from a codon optimized nucleic acid molecule so that the polypeptide preferentially binds to DNA of the genomic locus; and wherein the genomic locus of interest is associated with TP63, CCND1, CCNE1, YAP1, HRAS, PIK3CA, PIK3CG, NOTCH1, NOTCH 2, NOTCH 3, IRF6, CDKN2A, TP53, CASP8, PTEN, FAT1, RIPK4, EZH1, EZH2, MED1, MLL2, CDH1, FBXW7, PCLO, RIMS2, RB1, NSD1 or NFE2L2.

2. The method according to claim 1, wherein the at least one or more effector domains is selected from the group consisting of: transposase domain, integrase domain, recombinase domain, resolvase domain, invertase domain, protease domain, DNA methyltransferase domain, DNA demethylase domain, histone acetylase domain, histone deacetylases domain, nuclease domain, repressor domain, activator domain, nuclear-localization signal domains, transcription-protein recruiting domain, cellular uptake activity associated domain, nucleic acid binding domain and antibody presentation domain.

3. The method according to claim 1, wherein the at least one or more effector domains is a nuclease domain.

4. The method according to claim 3, wherein the nuclease domain is a non-specific FokI endonuclease catalytic domain.

5. The method according to claim 1, wherein altering expression of a genomic locus is repressing expression of the genomic locus and wherein the at least one or more effector domains included in the polypeptide is at least one or more repressor domains.

6. The method according to claim 5, wherein the genomic locus is associated with a gene selected from the group consisting of: TP63, CCND1, CCNE1, YAP1, HRAS, PIK3CA, PIK3CG and NFE2L2.

7. The method according to claim 5, wherein the polypeptide includes at least one mSin interaction domain (SID) repressor domain.

8. The method according to claim 7, wherein the polypeptide includes at least four SID repressor domains.

9. The method according to claim 5, wherein the polypeptide includes a Krüppel-associated box (KRAB) repressor domain or a fragment thereof.

10. The method according to claim 1, wherein altering expression of a genomic locus is activating expression of the genomic locus and wherein the at least one or more effector domains included in the polypeptide is at least one or more activator domains.

11. The method according to claim 10, wherein the genomic locus is associated with a gene selected from the group consisting of: NOTCH1, NOTCH 2, NOTCH 3, IRF6, CDKN2A, TP53, CASP8, PTEN, FAT1, RIPK4, EZH1, EZH2, MED1, CDH1, FBXW7, PCLO, RIMS2, RB1 and NSD1.

12. The method according to claim 10, wherein the polypeptide includes a VP16 activator domain.

13. The method according to claim 10, wherein the polypeptide includes a VP64 activator domain.

14. The method according to claim 10, wherein the polypeptide includes a p65 activator domain.

15. The method according to claim 1 wherein the DNA binding domain comprises $(X_{1-11}\text{-}X_{12}X_{13}\text{-}X_{14\text{-}33\ or\ 34\ or\ 35})_z$, wherein $X_{1-11}$ is a chain of 11 contiguous amino acids, wherein $X_{12}X_{13}$ is a repeat variable diresidue (RVD), wherein $X_{14\text{-}33\ or\ 34\ or\ 35}$ is a chain of 21, 22 or 23 contiguous amino acids, wherein z is at least 5 to 40, and wherein at least one RVD is selected from the group consisting of NI, HD, NG, NN, KN, RN, NH, NQ, SS, SN, NK, KH, RH, HH, HI, KI, RI, SI, KG, HG, RG, SD, ND, KD, RD, YG, HN, NV, NS, HA, S*, N*, KA, H*, RA, NA, and NC, wherein (*) means that the amino acid at $X_{13}$ is absent.

16. The method according to claim 15, wherein z is at least 10 to 26.

17. The method according to claim 15, wherein at least one of $X_{1-11}$ is a sequence of 11 contiguous amino acids set forth as amino acids 1-11 in a sequence ($X_{1-11}$-$X_{14-34}$ or $X_{1-11}$-$X_{14-35}$) of FIG. 15 or at least one of $X_{14-34}$ or $X_{14-35}$ is a sequence of 21 or 22 contiguous amino acids set forth as amino acids 12-32 or 12-33 in a sequence ($X_{1-11}$-$X_{14-34}$ or $X_{1-11}$-$X_{14-35}$) of FIG. 15.

18. The method according to claim 15, wherein the at least one RVD is selected from the group consisting of (a) HH, KH, NH, NK, NQ, RH, RN, SS for recognition of guanine (G); (b) SI for recognition of adenine (A); (c) HG, KG, RG for recognition of thymine (T); (d) RD, SI) for recognition of cytosine (C); (e) NV for recognition of A or G; and (f) H*, HA, KA, N*, NC, NS, RA, S* for recognition of A or T or G or C, wherein (*) means that the amino acid at $X_{13}$ is absent.

19. The method according to claim 18, wherein the RVD for the recognition of G is RN, NH, RH or KH; or the RVD for the recognition of A is SI; or the RVD for the recognition of T is KG or RG; and the RVD for the recognition of C is SD or RD.

20. The method according to claim 15, wherein at least one of the following is present

[LTLD] (SEQ ID NO: 1) or [LTLA] (SEQ ID NO: 2) or [LTQV] (SEQ ID NO 3) at $X_{1-4}$, or

[EQHG] (SEQ ID NO: 4) or [RDHG] (SEQ ID NO: 5) at positions $X_{30-33}$ or $X_{31-34}$ or $X_{32-35}$.

21. The method according to claim 1 wherein the N-terminal capping region or fragment thereof comprises 147 contiguous amino acids of a wild type N-terminal capping region, or the C-terminal capping region or fragment thereof comprises 68 contiguous amino acids of a wild type C-terminal capping region, or the N-terminal capping region or fragment thereof comprises 136 contiguous amino acids of a wild type N-terminal capping region and the C-terminal capping region or fragment thereof comprises 183 contiguous amino acids of a wild type C-terminal capping region.

* * * * *